United States Patent
Tahan et al.

(10) Patent No.: US 10,579,075 B2
(45) Date of Patent: Mar. 3, 2020

(54) LOW FLOW DETECTION DURING PERIOD OF NO FLOW

(71) Applicant: WINT WI Ltd, Rosh-Ha'ayin (IL)

(72) Inventors: Avy Tahan, Ramat-Gan (IL); Dror Galron, Hadera (IL)

(73) Assignee: Wint WI, Ltd., Rosh-Ha'ayin (IL)

( * ) Notice: Subject to any disclaimer, the term of this patent is extended or adjusted under 35 U.S.C. 154(b) by 200 days.

(21) Appl. No.: 15/820,187

(22) Filed: Nov. 21, 2017

(65) Prior Publication Data
US 2018/0143059 A1    May 24, 2018

Related U.S. Application Data

(60) Provisional application No. 62/425,494, filed on Nov. 22, 2016.

(51) Int. Cl.
*G05D 7/00* (2006.01)
*E03B 7/02* (2006.01)
(Continued)

(52) U.S. Cl.
CPC ............ *G05D 7/00* (2013.01); *A61B 5/4088* (2013.01); *A61B 5/4255* (2013.01);
(Continued)

(58) Field of Classification Search
None
See application file for complete search history.

(56) References Cited

U.S. PATENT DOCUMENTS

| 5,056,554 A | 10/1991 | White |
| 5,740,031 A * | 4/1998 | Gagnon .............. A01G 25/167 700/16 |

(Continued)

*Primary Examiner* — Natalie Huls
*Assistant Examiner* — Jermaine L Jenkins
(74) *Attorney, Agent, or Firm* — Finnegan, Henderson, Farabow, Garrett and Dunner, LLP

(57) ABSTRACT

A system is provided for detecting abnormal consumption in a distributed water infrastructure. The system may comprise at least one processor. The system may receive from at least one sensor associated with the distributed water infrastructure indications of regular water usage, wherein the distributed water infrastructure includes a plurality of water appliances. The system may determine from the indications received over a time period, at least one recurring time period of expected diminished water usage. The system may determine for the at least one recurring time period of expected diminished water usage at least one expected diminished water usage profile. The system may receive from the at least one sensor during a current time period of expected diminished water usage, real time indications of water usage, which may constitute a current water usage profile. The system may compare the current water usage profile during the expected period of diminished water usage with the at least one expected diminished water usage profile. The system may, based on the comparison, determine that water usage in the current water usage profile materially exceeds water usage in the at least one expected water usage profile. The system may execute a remedial action when, based on the comparison, the current water usage profile materially exceeds the at least one expected water usage profile.

20 Claims, 29 Drawing Sheets

(51) Int. Cl.
| | |
|---|---|
| *G01D 4/14* | (2006.01) |
| *G01F 1/00* | (2006.01) |
| *A61B 5/00* | (2006.01) |
| *G01F 15/075* | (2006.01) |
| *G01F 15/06* | (2006.01) |
| *G01D 4/00* | (2006.01) |
| *G06Q 20/14* | (2012.01) |
| *G06Q 50/06* | (2012.01) |
| *G01F 7/00* | (2006.01) |
| *G01M 3/28* | (2006.01) |
| *E03B 7/07* | (2006.01) |
| *G05B 19/406* | (2006.01) |
| *G05D 7/06* | (2006.01) |
| *G05B 13/02* | (2006.01) |
| *E03B 7/09* | (2006.01) |
| *G01F 15/00* | (2006.01) |
| *G08B 21/18* | (2006.01) |
| *F17D 5/06* | (2006.01) |
| *H04L 12/28* | (2006.01) |
| *F16K 37/00* | (2006.01) |
| *G01M 3/00* | (2006.01) |
| *E03B 1/02* | (2006.01) |
| *E03B 1/00* | (2006.01) |
| *G01M 3/26* | (2006.01) |

(52) U.S. Cl.
CPC .......... *A61B 5/6891* (2013.01); *A61B 5/7282* (2013.01); *A61B 5/747* (2013.01); *E03B 7/02* (2013.01); *E03B 7/071* (2013.01); *E03B 7/072* (2013.01); *E03B 7/09* (2013.01); *F16K 37/0025* (2013.01); *F17D 5/06* (2013.01); *G01D 4/004* (2013.01); *G01D 4/14* (2013.01); *G01F 1/00* (2013.01); *G01F 7/00* (2013.01); *G01F 15/005* (2013.01); *G01F 15/063* (2013.01); *G01F 15/066* (2013.01); *G01F 15/068* (2013.01); *G01F 15/0755* (2013.01); *G01M 3/2807* (2013.01); *G05B 13/026* (2013.01); *G05B 19/406* (2013.01); *G05D 7/0635* (2013.01); *G05D 7/0676* (2013.01); *G06Q 20/145* (2013.01); *G06Q 50/06* (2013.01); *G08B 21/187* (2013.01); *H04L 12/2825* (2013.01); *E03B 1/00* (2013.01); *E03B 1/02* (2013.01); *G01M 3/00* (2013.01); *G01M 3/26* (2013.01); *G05B 2219/37371* (2013.01); *H04L 2012/285* (2013.01); *Y02A 20/218* (2018.01); *Y02B 90/242* (2013.01); *Y02B 90/245* (2013.01); *Y04S 20/322* (2013.01); *Y04S 20/36* (2013.01); *Y04S 20/38* (2013.01); *Y04S 20/40* (2013.01)

(56) References Cited

U.S. PATENT DOCUMENTS

| | | |
|---|---|---|
| 6,963,808 B1 | 11/2005 | Addink et al. |
| 7,930,069 B2 | 4/2011 | Savelle, Jr. et al. |
| 7,966,099 B2 * | 6/2011 | Fima .................. E03B 1/00 700/276 |
| 8,428,891 B2 | 4/2013 | Jaeger |
| 8,918,294 B2 | 12/2014 | Stevens et al. |
| 9,109,349 B1 * | 8/2015 | Minton, Jr. ............. E03B 7/071 |
| 9,297,467 B1 | 3/2016 | Goseco |
| 9,456,297 B2 * | 9/2016 | Pi-Sunyer ............. G05B 15/02 |
| 9,491,571 B2 * | 11/2016 | Karp .................... G05B 15/02 |
| 9,565,513 B1 | 2/2017 | Malek et al. |
| 2002/0033759 A1 * | 3/2002 | Morello ................. G01M 3/18 340/605 |
| 2004/0128034 A1 | 7/2004 | Lenker et al. |
| 2006/0174707 A1 | 8/2006 | Zhang |
| 2009/0206059 A1 | 8/2009 | Kiko |
| 2009/0307116 A1 | 12/2009 | Al-Harbi |
| 2010/0082174 A1 | 4/2010 | Weaver |
| 2010/0265059 A1 | 10/2010 | Melker et al. |
| 2010/0313958 A1 | 12/2010 | Patel et al. |
| 2011/0251807 A1 | 10/2011 | Rada et al. |
| 2012/0086573 A1 | 4/2012 | Bischoff et al. |
| 2012/0136593 A1 | 5/2012 | Donaldson et al. |
| 2013/0080081 A1 | 3/2013 | Dugger et al. |
| 2013/0103215 A1 | 4/2013 | Dai et al. |
| 2013/0104251 A1 | 4/2013 | More et al. |
| 2013/0110621 A1 | 5/2013 | Gupta et al. |
| 2014/0180761 A1 | 6/2014 | Yolles et al. |
| 2014/0207708 A1 | 7/2014 | Amram et al. |
| 2014/0245208 A1 | 8/2014 | Javey et al. |
| 2015/0308856 A1 | 10/2015 | Srinivasan et al. |
| 2016/0012748 A1 | 1/2016 | Donavon |
| 2016/0146648 A1 | 5/2016 | Patel et al. |
| 2016/0150298 A1 | 5/2016 | Kim |
| 2016/0161310 A1 | 6/2016 | Leaders et al. |
| 2016/0161940 A1 | 6/2016 | Max |
| 2016/0349140 A1 | 12/2016 | Teymouri |
| 2016/0350880 A1 | 12/2016 | Tyner et al. |
| 2016/0356026 A1 | 12/2016 | Engler |
| 2017/0030798 A1 | 2/2017 | DeVerse |
| 2017/0053360 A1 | 2/2017 | Loeb et al. |
| 2017/0085966 A1 | 3/2017 | Berkcan et al. |
| 2017/0089047 A1 * | 3/2017 | Kovscek ................ E03B 7/071 |
| 2017/0131174 A1 | 5/2017 | Enev et al. |
| 2017/0290941 A1 | 10/2017 | Rabin et al. |
| 2017/0322567 A1 | 11/2017 | Klein et al. |
| 2017/0370754 A1 | 12/2017 | Croteau |
| 2018/0259133 A1 | 9/2018 | Ravid et al. |

* cited by examiner

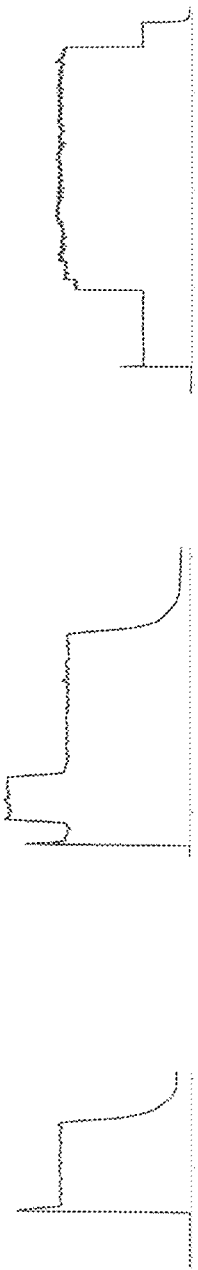
Fig. 10d
Fig. 10e
Fig. 10f
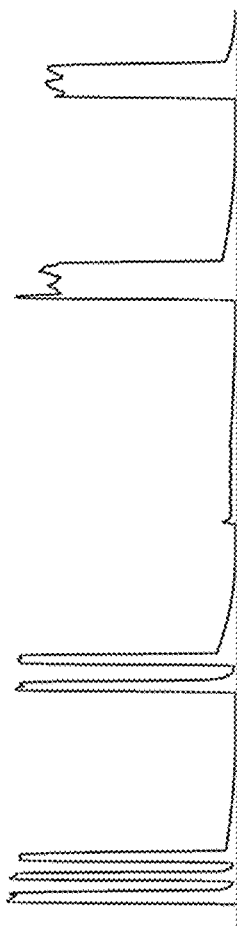
Fig. 10g

LOW FLOW DETECTION DURING PERIOD OF NO FLOW

CLAIM FOR PRIORITY

This application claims benefit of priority of U.S. Provisional Patent Application No. 62/425,494, filed Nov. 22, 2016, which is incorporated herein by reference in its entirety.

TECHNICAL FIELD

The present disclosure may be related to devices, systems, and methods for detecting the usage of liquids and initiating appropriate remedial actions. More particularly, part of the disclosure may be directed to identifying specific types of liquid usage and initiating appropriate remedial action.

BACKGROUND

A distributed water infrastructure may include any arrangement of conduits for supplying plumbing fixtures, appliances, storage devices, treatment devices, or any other device that receives water. For example, a distributed water infrastructure may include the pipes and/or other conduits of a city, a neighborhood, a complex of buildings, a building, a floor, and a room. A distributed water infrastructure may also include a collection of conduits within a room. In an industrial, commercial, or residential setting, the conduits in individual areas of a single floor might each be considered a separate distributed water infrastructure. Alternatively, multiple contiguous or non-contiguous conduits might be considered a single distributed water infrastructure.

The distributed water infrastructure may be essential to many commercial and private activities. The continued use of a distributed water infrastructure runs the risk of leaks and the unknowing waste of water. In some instances, users of a distributed water infrastructure do not realize a leak is occurring until it is too late to prevent damage to buildings and the waste of large amounts of water. In many instances, users may not know how water in a distributed water infrastructure is being used, and are unable to discern what are the sources of water waste if the leaks are slow. At times, the process of determining what appliance may be leaking may be difficult.

Because it can be difficult to know how water is being used, there remains an opportunity to track water to determine if water is stolen or wasted. As water is essential to human health, greater information on the use of water may also enable the ability to check on the health of remote persons, to see if they are alive, brushing their teeth, or doing other health-related activities. Additional detail about various water usage by employing high resolution sensors may provide solutions to these problems.

It may therefore be desirable to employ methods and systems for monitoring the use of water in a distributed water infrastructure. Such a system may enable greater control over a property's water system, may enable greater water savings by reducing unnecessary expenses, and may enable better alerts regarding any potentially damaging water situation.

SUMMARY

The present disclosure generally relates to a system for detecting flow of a fluid. While the present disclosure provides examples of detecting water flow, it should be noted that aspects of the disclosure in their broadest sense, are not limited only to systems for detecting water flow. Rather, it may be contemplated that the forgoing principles may be applied to other fluids as well, including gases and liquids other than water.

Exemplary embodiments of the present application provide for, but are not limited to, a system for detecting abnormal consumption in a distributed water infrastructure. The system may receive from at least one sensor associated with the distributed water infrastructure signals indicative of water usage in the distributed water infrastructure, and aggregate groups of signals to construct a plurality of time-based water event profiles, each water event profile containing a distribution of water usage indicators over time. The system may store a subset of the plurality of water event profiles in memory as normal water event profiles, and receive, from the at least one sensor, signals indicative of current water usage in the distributed water infrastructure. The system may construct, from the signals indicative of current water usage, at least one current water event profile, and compare the at least one current water event profile with normal water event profiles stored in the memory. The system may initiate remedial action if the at least one current water event profile does not substantially correspond to normal water event profiles stored in the memory.

Exemplary embodiments of the present application provide for, but are not limited to, an abnormal consumption detection system for a distributed water infrastructure. The system may comprise an electronically controllable valve, a remote communication transmitter, a remote communication receiver, at least one consumption sensor for measuring water flow information associated with the distributed water infrastructure, and at least one processor. The system may determine from the water flow information obtained from the at least one consumption sensor a potential abnormal consumption associated with the distributed water infrastructure. The system may automatically close a valve, without human intervention, when the potential abnormal consumption is determined. The system may transmit, via the remote communication transmitter to a remote administrator, alert information about the potential abnormal consumption to enable an administrator to decide based on the transmitted information whether to reopen the valve. The system may receive from the administrator via the remote communication receiver a control signal to reopen the valve, despite the information about the potential abnormal consumption, and reopen the valve.

Exemplary embodiments of the present application provide for, but are not limited to, a system for detecting abnormal consumption in one portion of a distributed water infrastructure while normal water usage occurs in another portion of the distributed water infrastructure. The system may comprise at least one processor. The system may receive from at least one sensor associated with the distributed water infrastructure indications of regular water usage. The system may determine, from a plurality of indications received over a time period, a plurality of baseline water usage profiles. The system may receive from the at least one sensor a current water usage profile. The system may compare the current water usage profile with the plurality of baseline water usage profiles. The system may determine an abnormal water consumption based on the comparison between the current water usage profile and the plurality of baseline water usage profiles. The system may generate an abnormal water consumption signal when abnormal water consumption is determined.

Exemplary embodiments of the present application provide for, but are not limited to, a system for detecting abnormal consumption in a distributed water infrastructure. The system may comprise at least one processor. The system may receive from at least one sensor associated with the distributed water infrastructure indications of regular water usage, wherein the distributed water infrastructure includes a plurality of water appliances. The system may determine from the indications received over a time period, at least one recurring time period of expected diminished water usage. The system may determine for the at least one recurring time period of expected diminished water usage at least one expected diminished water usage profile. The system may receive from the at least one sensor during a current time period of expected diminished water usage, real time indications of water usage, which may constitute a current water usage profile. The system may compare the current water usage profile during the expected period of diminished water usage with the at least one expected diminished water usage profile. The system may, based on the comparison, determine that water usage in the current water usage profile materially exceeds water usage in the at least one expected water usage profile. The system may execute a remedial action when, based on the comparison, the current water usage profile materially exceeds the at least one expected water usage profile.

Exemplary embodiments of the present application provide for, but are not limited to, a detection system for a distributed water infrastructure, wherein the system is configured to determine at least one of a human health or lifestyle state from water usage patterns in the distributed water infrastructure. The system may comprise at least one processor. The system may receive from at least one sensor associated with the distributed water infrastructure signals indicative of water usage in the distributed water infrastructure. The system may determine from the signals indicative of water usage a current water usage pattern. The system may access a database of a plurality of stored water usage patterns, wherein each at least one stored water usage pattern is associated with at least one human health or lifestyle state. The system may compare at least one current water usage pattern with at least some of the stored water usage patterns. The system may, based on the comparison, identify a human health or lifestyle condition reflected by the current water usage pattern. The system may institute a remedial action corresponding to the identified human health or lifestyle state.

Exemplary embodiments of the present application provide for, but are not limited to, a system for differentiating between overlapping water events in a distributed water infrastructure including a plurality of water appliances. The system may comprise at least one processor. The system may repeatedly measure at least one overall water usage indicator of the distributed water infrastructure, the at least one water usage indicator including at least one of an overall flow rate and an overall flow volume in the distributed water infrastructure. The system may detect, in the repeated measurements, a first sustained increase. The system may store in memory a first indicator of the first sustained increase. The system may attribute in memory the first sustained increase to a first water event in the distributed water infrastructure. The system may, during the first sustained increase, detect in the overall measurements a second sustained increase. The system may store in memory a second indicator of the second sustained increase. The system may attribute, in memory, the second sustained increase to a second water event in the distributed water infrastructure. The system may detect, following initiation of the first sustained increase and the second sustained increase, in the repeated measurements a decrease in the overall water usage indicator. The system may attribute to the decrease a third indicator. The system may compare the third indicator with at least one of the first indicator and the second indicator stored in memory to determine a substantial match and determine a cessation of at least one of the first water event and the second water event. The system may initiate an action based on the cessation determination.

Exemplary embodiments of the present application provide for, but are not limited to, a system for tracking usage of a plurality of water appliances in a distributed water infrastructure. The system may comprise at least one processor. The system may receive, from a location in the distributed water infrastructure upstream of the plurality of water appliances, historical water usage measurements. The system may determine from the historical water usage measurements at least one unique water usage signature associated with each of the plurality of water appliances. The system may store in memory each at least one unique water usage signature for each of the plurality of appliances. The system may receive, from the location in the distributed water infrastructure upstream of the plurality of water appliances, current water usage measurements. The system may determine from the current water usage measurements at least one current water usage signature. The system may compare the current water usage signature with at least one of the unique water usage signatures stored in memory to determine a match. The system may, based on the signature match, ascertain an identifier of a water appliance in current use.

Exemplary embodiments of the present application provide for, but are not limited to, a system for determining operational states of specific categories of water appliances using a plurality of geographically distributed water sensors. The system may comprise at least one central processor. The system may receive water appliance usage data from the plurality of geographically distributed water sensors, wherein each water sensor is located upstream of a plurality of water appliances in an associated distributed water infrastructure, and wherein each water sensor is configured to collect data from an infrastructure inlet flow reflective of operation of at least one specific category of water appliance downstream of the water sensor. The system may compare the water appliance usage data from the plurality of geographically distributed water sensors to determine trends in operation of the at least one specific category of water appliance across a population. The system may output information about the trends in operation.

Exemplary embodiments of the present application provide for, but are not limited to, a system for determining from a location upstream of a plurality of water appliances, whether a specific water appliance is malfunctioning. The system may comprise at least one processor. The system may detect, from at least one sensor in a distributed water infrastructure upstream of the plurality of water appliances, a plurality of normal water usage profiles. The system may associate at least one of the plurality of normal water usage profiles with each of the plurality of water appliances. The system may store each of the plurality of normal water usage profiles in a manner associating each of the plurality of normal water usage profiles with an associated water appliance. The system may detect at least one current water usage profile. The system may compare the at least one current water usage profile with at least one of the stored normal water usage profiles to determine a corresponding identity of an associated water usage appliance and to determine if a substantial deviation exists between the stored normal water usage profile for the identified appliance and the at least one current water usage profile. The substantial deviation may be reflective of a potential malfunction in the associated water usage appliance. The system may initiate remedial action if the substantial deviation, reflective of a potential malfunction, is determined.

Exemplary embodiments of the present application provide for, but are not limited to, a system for tracking, in a distributed water infrastructure, water usage by category. The system may comprise at least one processor. The system may receive from at least one sensor associated with the distributed water infrastructure signals indicative of water usage in the distributed water infrastructure. The system may, based on the signals indicative of water usage, construct a plurality of profiles. The system may assign each profile to one of a plurality of water usage categories. The system may collect, from the at least one sensor, signals indicative of water usage for substantially all water delivered through the distributed water infrastructure in a time period. The system may construct a plurality of water usage profiles in the aggregate, encompassing substantially all water delivered through the distributed water infrastructure in the time period. The system may assign each constructed water usage profile to one of the plurality of water usage categories. The system may output, for display, water usage for the time period for each of the plurality of water usage categories.

Exemplary embodiments of the present application provide for, but are not limited to, a system for differentiating between water usage of multiple water consumers using a common distributed water infrastructure. The system may comprise at least one processor. The system may receive from a water sensor in the distributed water infrastructure upstream of a plurality of appliances, signals indicative of water usage. The system may construct from the signals indicative of water usage a plurality of water event profile signatures. The system may, based on differences between similar water event profiles, associate at least one water event profile signature with a first water consumer and associate a second water event profile signature with a second water consumer. The system may store the water event profile signatures for the first water consumer and the second water consumer. The system may construct current water event profiles reflecting subsequent water usage in the distributed water infrastructure. The system may compare the current water event profiles with water event profile signatures stored in memory. The system may, based on the comparison, attribute a first current water event profile to the first water consumer and attribute a second current water event profile to the second water consumer. The system may output data for generating at least one report of water usage by the first water consumer.

Exemplary embodiments of the present application provide for, but are not limited to, an electronic sensing and allocation system for a distributed water infrastructure containing a plurality of differing appliances. The system may comprise at least one processor. The system may receive, from at least one sensor upstream of the plurality of differing appliances, a plurality of signals indicative of water usage within the distributed water infrastructure. The system may extract, from the plurality of signals, first information identifying a volume of water usage of at least a first appliance. The system may attribute a first volume of water to a first category. The system may extract, from the plurality of signals, second information identifying a volume of water usage of at least a second appliance. The system may attribute a second volume of water to a second category, wherein a first rate schedule is applicable to the first category, and a second rate schedule, other than the first rate schedule, is applicable to the second category. The system may output a first indication of the first volume of water together with an indicator attributing the first volume of water to the first rate schedule, and output a second indication of the second volume of water together with an indicator attributing the second volume of water to the second rate schedule. The system may enable billing of the first and second volumes of water to a consumer at differing rates based on differing uses.

Exemplary embodiments of the present application provide for, but are not limited to, a system for monitoring water usage of a plurality of appliances in a plurality of distributed locations remote from one another. The system may comprise at least one central processor. The system may receive water usage data from the plurality of distributed locations. The system may determine, from the water usage data received from the plurality of distributed locations, a common appliance used in each of the plurality of distributed locations. The system may analyze a subset of the water usage data attributable to the common appliance to determine usage patterns associated with the common appliance across the plurality of distributed locations. The system may output usage pattern analytics associated with the common appliance.

BRIEF DESCRIPTION OF THE DRAWINGS

FIGS. 10a-g illustrate exemplary water usage patterns over time, with flow rate on the y-axis and time on the x-axis.

DETAILED DESCRIPTION

Figure 1:
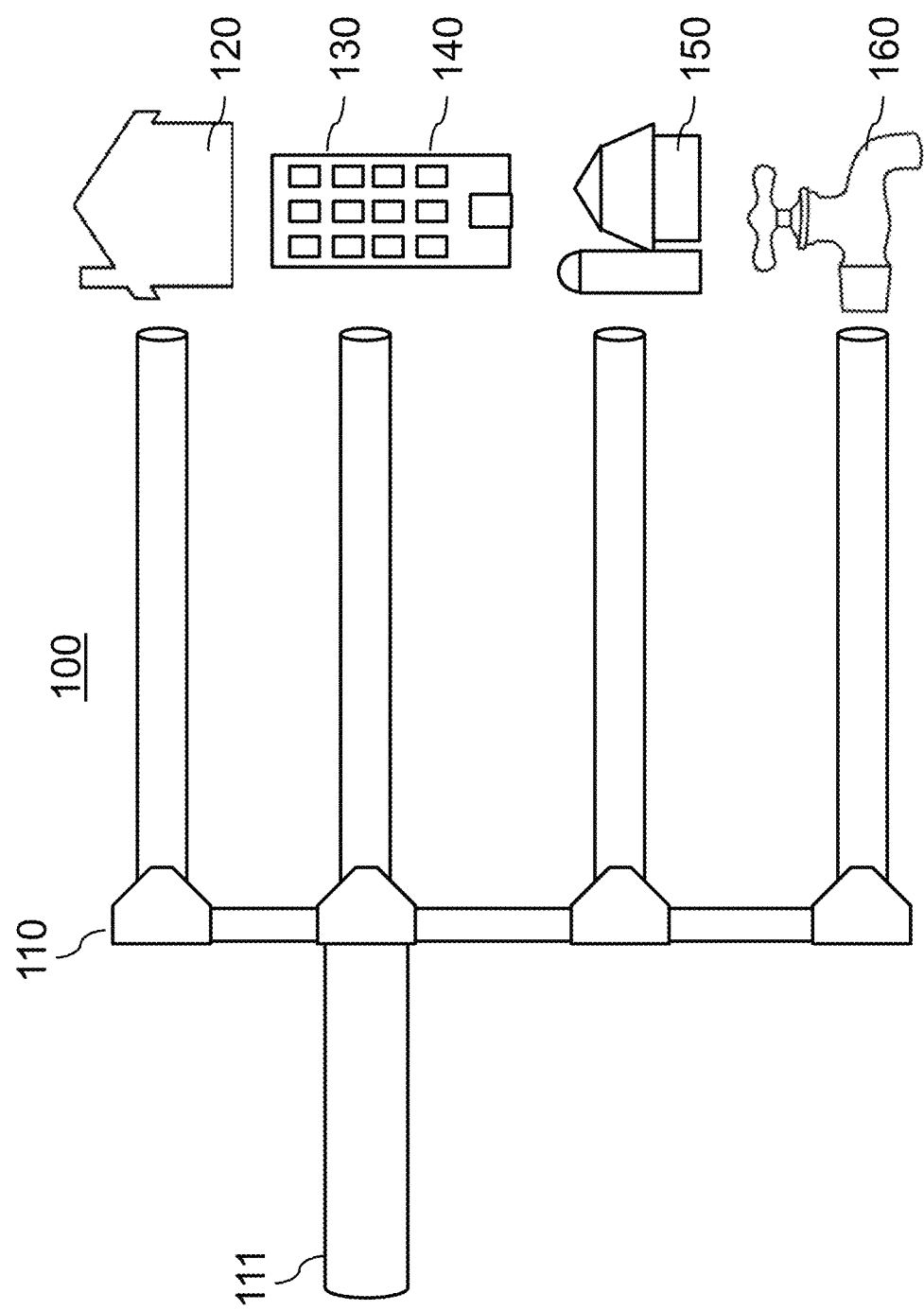
FIG. 1 illustrates an exemplary distributed water infrastructure.

Exemplary embodiments of the present application are described in further detail below.

Definition of Terms

Unless otherwise defined, all technical and scientific terms used herein have the same meaning as commonly understood by one of ordinary skill in the art. In case of conflict, the present document, including definitions, will control. Preferred methods and materials are described herein, although methods and materials similar or equivalent to those described herein can be used in practice or testing of embodiments of the present disclosure. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an," and "the" include plural references unless the context clearly dictates otherwise. The present disclosure also contemplates other embodiments "comprising," "consisting of," and "consisting essentially of" the embodiments or elements presented herein, whether explicitly set forth or not.

The conjunctive term "or" may include any and all combinations of one or more listed elements associated by the conjunctive term. For example, the phrase "an apparatus comprising a or b" may refer to an apparatus including a where b may be not present, an apparatus including b where a may be not present, or an apparatus where both a and b are present. The phrases "at least one of a, b, . . . , and n" or "at least one of" a, b, . . . , n, or combinations thereof" are defined in the broadest sense to mean one or more elements selected from the group comprising a, b, . . . , and n, that is to say, any combination of one or more of the elements a, b, . . . , or n including any one element alone or in combination with one or more of the other elements, which may also include, in combination, additional elements not listed.

The terms "first," "second," "third," and the like, as used herein, do not denote any order, quantity, or importance, but rather are used to distinguish one element from another.

The term "substantially," as used herein, represents the inherent degree of uncertainty that may be attributed to any quantitative comparison, value, measurement, or other representation. The term "substantially" may be also utilized herein to represent the degree by which a quantitative representation may vary from a stated reference without resulting in a change in the basic function of the subject matter at issue.

The term "water consumer," as used herein, represents both water appliances and people that consume water. It may also be a combination of the two. Water consumers may use water directly or indirectly.

The term "system," as used herein, may include both hardware and software that can either work in tandem or independently. The system can be located locally or in the cloud or a combination of each.

The term "sensor," as used herein, represents a device that provides an output reflective of the water usage, such as flow rate, and the water properties like temperature, pressure, etc. A sensor can be a mechanical sensor such as a multi jet sensor, positive displacement sensor, ultrasonic sensor, binary sensor (capable of detecting presence or absence of liquid, e.g. a humidity detector) or any other instrument capable of outputting a signal reflecting the presence of liquid flow. At least one sensor can be one, two, or a plurality of sensors regardless of whether they are in a common location or in various locations.

The term "signals indicative of water usage" or "water usage pattern" as used herein, represents any electronic representation of a property associated with the flow of water (or in a more general sense liquid). Such signals might include an electronic representation of flow, volume, pressure, velocity, or any combination thereof. Thus, a signal indicative of water usage may include any output of at least one sensor. An output of a flow sensor, digital signal, analog signal, and wire or wireless signal, may be any output that correlates to the liquid flow.

The term "substantial deviation" as used herein refers to a measurement of deviation from the normal expected usage for each water-using appliance. A substantial deviation from the normal expected usage can help determine proper usage and efficiency of the water-using appliance. In some embodiments, a substantial deviation may be greater than a standard deviation of at least one characteristic of normal expected usage for a water-using appliance. A substantial deviation may be greater than some preset value. A substantial deviation may be a learned value determined by a machine learning algorithm.

The term "noise" or "acoustic noise" as used herein refers to fluctuations in a signal. Noise may refer to an acoustic sound. Noise may refer to errors associated with the signal to noise ratio of a sensor. Noise may also refer to random fluctuations in a water flow rate that are associated with the flow of water through a distributed water infrastructure. Certain water consumers may generate noise of different magnitude and/or different frequencies.

Although pressure and fluid flow rate are theoretically related according to Poiseuille's law, the validity of this law may be based on assumptions that typically may not hold in real-world conditions that prevail in distributed water infrastructures. For example, Poiseuille's law assumes laminar flow of a Newtonian fluid within a cylindrical pipe of constant cross section. In real-world branched pipeline fluid distribution systems, however, fluid flow may be turbulent and experience acceleration (and deceleration). A measurement of fluid flow may therefore provide opportunities to have superior resolution over a measurement of pressure.

Inventive concepts may include one or more of the following, either alone or in combination with other disclosed embodiments. Moreover, it is contemplated that the components of each of the following embodiments can be combined with one or more components of other disclosed embodiments, and therefore, the specific combinations discussed herein are not to be considered restrictive or exclusive.

Exemplary Embodiments of Event-Based Leak Detection

The present application provides for leak detection during normal water usage. A potential benefit of some embodiments of the present disclosure include their ability to detect abnormal consumption, even during times of normal water usage. Systems and methods of the present disclosure may be enabled to do so by determining a baseline of existing usage, and then ascertaining a non-expected deviation from the baseline. In addition or in the alternative, systems and methods may be able to identify the use of water at a granular level, such that normal water usage may be categorized into discrete events, and the addition of a new unrecognized event may indicate a leak.

An aspect of some embodiments may include a system for detecting abnormal consumption of water in a distributed water infrastructure. FIG. 1 illustrates an exemplary distributed water infrastructure 100. Distributed water infrastructure 100 may include any arrangement of conduits 110 for supplying plumbing fixtures, appliances, storage devices, treatment devices, or any other device that receives water.

A distributed water infrastructure may have a single inlet, indicated by inlet 111. A distributed water infrastructure may include a single household, indicated by water consumer 120. A distributed water infrastructure may include an entire building with several floors, indicated by water consumer 130. A distributed water infrastructure may include a single floor within a building, indicated by water consumer 140. A distributed water infrastructure may service different types of water users. A distributed water infrastructure may service agricultural users, such as for irrigation, indicated by water consumer 150. A distributed water infrastructure may service household users, such as for a faucet, indicated by water consumer 160. In some embodiments, each water consumer 120-160 may consume water in a unique manner that may enable identification of the water consumer.

The term abnormal consumption refers generally to flow of a fluid that deviates from normal flow by at least one water usage indicator. A water usage indicator may include, for example, an average flow rate, an initial flow rate, a total volume associated with a current water event, a noise in signals indicative of water usage, and a pattern in a rate of water usage. The consumption of a fluid may be characterized by a water consumption profile. Such a profile may include a signal or a group of signals representative of fluid flow. By way of example, a time-based water event profile may include a flow rate over time that may be associated with a particular event. Alternatively or additionally, a water event profile may include an average flow rate over time, and a characteristic feature of a water event.

In one aspect, abnormal water consumption may be defined as a water consumption profile, sensed in a distributed water infrastructure, that deviates significantly from one or more existing water consumption profiles that characterize normal water consumption in a distributed water infrastructure. An existing water consumption profile may be a pre-defined profile within a library of profiles general to a variety of distributed water infrastructures or may be pre-learned for a specific distributed water infrastructure. The deviation between a sensed water consumption profile and an existing water consumption profile may be measured quantitatively by comparing the sensed consumption profile with each of the existing water consumption profiles using any suitable distance measure of similarity or dissimilarity. The deviation of the sensed water consumption profile from an existing consumption profile may be considered significant when the distance of the sensed consumption profile is beyond an acceptable distance limit defined for the existing consumption profile. Abnormal water consumption may also be defined by a mathematical function that characterizes a known, undesirable consumption profile, which may then be compared with a sensed consumption profile in order to identify an abnormality.

In accordance with the present disclosure, a system for detecting flow of a fluid may include at least one processor. The at least one processor may include any physical device having an electric circuit that performs a logic operation on input or inputs. For example, a processor may include one or more integrated circuits, microchips, microcontrollers, microprocessors, all or part of a central processing unit (CPU), graphics processing unit (GPU), digital signal processor (DSP), field-programmable gate array (FPGA), or other circuits suitable for executing instructions or performing logic operations. The instructions executed by a processor may, for example, be pre-loaded into a memory integrated with or embedded into the processor or may be stored in a separate memory. Memory may include a random access memory (RAM), a read-only memory (ROM), a hard disk, an optical disk, a magnetic medium, a flash memory, other permanent, fixed, or volatile memory, or any other mechanism capable of storing instructions or data.

More than one processor may be used for any function. Each processor may have a similar construction or the processors may be of differing constructions that are electrically connected or disconnected from each other. For example, the processors may be separate circuits or integrated in a single circuit. When more than one processor is used, the processors may be configured to operate independently or collaboratively. The processors may be coupled electrically, magnetically, optically, acoustically, mechanically, or by other means that permit them to interact.

In one embodiment, a processor may be a data processor, a personal computer, or a mainframe for performing various functions and operations. The system for detecting abnormal consumption of water in a distributed water infrastructure may be implemented, for example, by a general purpose computer or a data processor selectively activated or reconfigured by a stored computer program, or may be a specially constructed computing platform for carrying out the features and operations described herein. Moreover, the system for detecting abnormal consumption of water in a distributed water infrastructure may be implemented or provided with a wide variety of components or systems, including one or more of the following: central processing units, co-processors, memories, registers, or other data processing devices and subsystems.

In accordance with the present disclosure, a system for detecting flow of a fluid in accordance with the present disclosure may include at least one sensor. A sensor may be any device that detects or measures a physical property and records, indicates, or otherwise responds to it. For example, a sensor may provide an output reflective of water usage, such as flow rate. At least one sensor may include a mechanical sensor, such as a multi-jet sensor, a positive displacement sensor, an ultrasonic sensor, or any other instrument capable of outputting a signal reflecting the presence of fluid flow. A sensor may also be a device that provides an output reflective of water properties, such as, by way of example only, temperature, pressure, flow rate, flow volume, salinity, pH, and viscosity. At least one sensor may include a binary sensor that may be capable of detecting the presence or absence of a fluid, such as a humidity detector. In other embodiments, at least one sensor may also be able to qualitatively or quantitatively measure the presence of a bio-film. The at least one sensor may include a water flow sensor having an unmeasured flow reducer.

Some embodiments may include a water flow sensor configured to detect flow at a rate of less than about 2 liters per hour. In some embodiments, a water flow sensor may be configured to detect flow at a rate of less than about 1 liter per hour. In other embodiments, a water flow sensor may be configured to detect flow at a rate of less than about 0.5 liters per hour, or less than about 0.2 liters per hour.

In some embodiments, a water sensor may be an electronic or electro-mechanical device that can detect the flow of water through a distributed water infrastructure. The water sensor may be connected to at least one processor to convey signals indicative of water usage in real-time. The sensor itself may be based on multi jet or ultrasonic technology and the signals the sensor conveys to at least one processor may be quantitative, time-based values indicating flow rate or time difference or any derivative thereof. The at least one sensor may be a single sensor or a plurality of sensors. A plurality of sensors may be positioned in a common location and/or may be positioned in various separated locations. The processor or processors that receive the signals may be connected to the sensor locally or may be located at some remote, distributed infrastructure.

In accordance with the present disclosure, a system for detecting flow of a fluid may include at least one processor configured to receive signals indicative of current water usage. The at least one processor may be configured to receive signals from a local sensor. In other embodiments, the at least one processor may be configured to receive signals from a remote sensor, through wired or wireless communication. Signals indicative of water usage may be any electronic representation of a property associated with the flow of a fluid. Signals indicative of current water usage may be signals received in real-time by at least one processor from at least one sensor associated with some distributed water infrastructure. The signals indicative of current water usage may each be represented by some quantitative value equivalent to the time at which the signal was received whether as a timestamp, or as a relative time difference from the previous signal in the sequence, or as a cumulative measure of time from a reference in time.

A signal indicative of water usage may include any output of the at least one sensor. Such a signal may include an electronic representative of flow, volume, pressure velocity, or any combination thereof. A signal indicative of water usage may be an output of a flow sensor, which may be a digital or analog signal. The at least one processor may be configured to receive signals indicative of water usage through a wire, and may also be configured to receive signals wirelessly. The signals indicative of water usage may be associated with a timestamp. In some embodiments, a signal may be received every time a predefined amount of water flows into or through the distributed water infrastructure.

In accordance with the present disclosure, a system for detecting flow of a fluid may include at least one processor configured to aggregate groups of signals. Aggregating groups of signals may include a process whereby signals indicative of water consumption that are determined to originate from the same cause are grouped together into single, meaningful entities. The signals may be determined to originate from the same cause according to some feature of the signals that may be reflective of water usage, such as flow rate, change in flow rate, volume, time difference between receiving signals, or any combination thereof. The at least one processor may be configured to construct water event profiles based on at least one parameter selected from an average flow rate, an initial flow rate, a total volume associated with a current water event profile, a noise in signals indicative of water usage, and a change in the rate of water usage.

In embodiments of the present disclosure, the at least one processor may be configured to construct a plurality of time-based water event profiles. Aggregated groups of signals may be transformed mathematically into an alternative representation. Mathematical transformation of the groups of signals may be any mathematical operation or function that maps the signals in a group of signals either individually or collectively from one quantitative representation to another quantitative representation. The aggregated groups of signals may be processed automatically or semi-automatically in order to determine the individual groups of signals or some combination of the groups of signals that represent one or more time-based water event profiles. In this way, a time-based water event profile may be constructed to be representative of water consumption that may be typical in a particular distributed water infrastructure. In some embodiments, a plurality of time-based water event profiles may be constructed that represent water consumption that may be typical in a particular distributed water infrastructure.

In accordance with the present disclosure, each water event profile constructed by the at least one processor may include a distribution of water usage indicators over time. In some embodiments, signals indicative of water usage may be received sequentially in time. The signals may be sent continuously. In other embodiments, the signals may be sent at intervals. Individual signals may be represented by some quantitative value equivalent to the time at which the signal was generated, sent, or received. For example, a quantitative value equivalent to the time the signal was received may be a timestamp, a relative time difference since the previous signal in the sequence, or a cumulative measure of time from some reference in time.

Accordingly, a time-based water event profile may be a collection of time-based signals that have been aggregated into groups, or into groups of groups, in a meaningful way. For example, a time-based water event profile may be a distribution of time-based signals over time, and may be represented in a graph as flow rate as a function of time.

In accordance with the present disclosure, a system for detecting flow of a fluid may include at least one processor configured to store a subset of the plurality of water event profiles in memory as normal water event profiles.

Storage may be implemented with a wide variety of systems, subsystems, and/or devices for providing memory or storage including, for example, one or more of the following: a read-only memory (ROM) device, a random access memory (RAM) device, a tape or disk drive, an optical storage device, a magnetic storage device, a redundant array of inexpensive disks (RAID), and/or any other device capable of providing storage and/or memory. Storage may be performed locally, or at a distant location. In some embodiments, physical storage may span multiple servers and locations. In some embodiments, storage services may be accessed through a co-located cloud computer service, a web service application programming interface (API), or by applications that utilize the API, such as cloud desktop storage, a cloud storage gateway, or web-based content management systems.

A normal water event profile may be a water event profile that occurs regularly in a distributed water infrastructure, and may be representative of a typical use of water. A normal water event profile may be learned during a learning period, saved in memory, and then provided as a reference that characterizes the normal water consumption in a distributed water infrastructure.

In accordance with the present disclosure, a system for detecting flow of a fluid may include at least one processor configured to receive from the at least one sensor, signals indicative of current water usage. Signals indicative of current water usage may be signals received in real-time by at least one processor from at least one sensor associated with a distributed water infrastructure. The signals indicative of current water usage may each be represented by a quantitative value equivalent to the time at which the signal was received, whether as a timestamp, or as a relative time difference since the previous signal in the sequence, or as a cumulative measure of time from a reference in time.

In accordance with the present disclosure, a system for detecting flow of a fluid may include at least one processor configured to construct, from the signals indicative of current water usage, at least one current water event profile. The signals indicative of current water usage in a distributed water infrastructure may be grouped and transformed mathematically using the same operations described above for the plurality of water event profiles, which may have previously been constructed for the same distributed water infrastructure. In this way, a water event profile for the current water usage may be constructed that is comparable to other water event profiles for the same distributed water infrastructure.

In accordance with the present disclosure, a system for detecting flow of a fluid may include at least one processor configured to compare the at least one current water event profile with normal water event profiles stored in memory. The current water event profile or profiles may be compared to each of the normal event profiles that have been stored in memory for the distributed water infrastructure by applying a suitable mathematical operation, which may calculate a quantitative value for either the similarity or dissimilarity between the current event profile and each of the normal event profiles.

In some embodiments, a remedial action may be initiated if the at least one current water event profile does not substantially correspond to normal water event profiles stored in memory. Initiating remedial action may include providing one or more notifications to one or more individuals or systems. In one embodiment, the notification may be a signal provided to a processor. In another embodiment, the notification may be a message provided to a user, administrator, or any other individual. The message may be in the form of written text, graphical illustration, or a physical signal conveyed through the distributed water infrastructure. Written text or graphical illustrations may provide an indication of abnormal usage in a general sense or in a specific sense. The notification may provide information about abnormal usage associated with a particular appliance, fixture, or other water receiving device, or the notification may provide general information of a potential abnormality associated with the distributed water infrastructure. The notification may indicate that an appliance, such as a toilet or sink may be leaking. The notification may broadly note that a leak was detected in a distributed water infrastructure or a particular portion of a distributed water infrastructure. In some embodiments, notifications may provide notice for events other than leak detection. For example, a notification may be provided indicating degradation in the performance of an appliance, or some other variation from normal usage of an appliance. Some non-limiting examples of variations from normal usage of an appliance include a shower duration that was longer than normal and a toilet that may be continuously running.

Notifications may be in the form of physical signals such as the pulsing of water through a distributed water infrastructure. For example, if a shower may be longer than normal, water may be pulsed to notify the user of the same. A series of pulses or a sequential series of pulses may be provided to the user. The system may be configured to receive a reply message from the user through the user's variance of water usage. For example, if the user turns off and then turns on the water, the system may be configured to permit continued water flow. Otherwise, if no reply is received from the user, the system may be configured to impede or fully restrict water flow.

The notifications may also include other types of physical indicators such as an alarm, vibration, or a warning light. The notifications may be provided to a mobile communication device, a telephone device, a computer, or any other electronic instrument, such as a laptop, tablet, computer, cell phone, or smart phone. The notification may or may not be immediately perceptible to a user. For example, remedial action may include sending data to a computer system, server, wearable, or other computing device for later processing. As another example, notifications may be collected in a system and then a report may be generated summarizing the notifications. Alternatively, once a number of notifications has accumulated, then further action may be taken.

In some embodiments, remedial action may also include directly or indirectly impeding water flow to some or all of the distributed water infrastructure. For example, a notification may be sent to a valve that causes the valve to restrict or completely halt water flow to some or all of the distributed water infrastructure. Alternatively, a notification may include a message to an individual of a potential leak, and may provide the individual with an option to intervene and shut off one or more valves. In another embodiment, if a notification is provided to a valve to halt water flow, a further notification may be provide to an individual to give the individual the ability to override the stop of water flow. In some embodiments, written notifications may be provided, for example, in the form of SMS messages, emails, social media messages, pop-ups, or through a dedicated application.

In accordance with the present disclosure, a remedial action may be initiated, if at least one water profile does not substantially correspond to a normal water event profile. In some embodiments, a current water event profile, which may be sensed in some distributed water infrastructure, may be compared to a normal event profile using mathematical operations that output a quantitative measure of similarity or dissimilarity between the two profiles. The current event profile may not substantially correspond to the normal event profile if the measure of similarity or dissimilarity lies beyond the acceptable limits of correspondence that may be defined for the normal event profile. In certain embodiments, the acceptable limits of correspondence may be expressed by a standard deviation or variance or any other quantitative measure of spread defined over the numerical representation of the normal water event profile. The quantitative measure of dissimilarity may be sufficient to identify an event of interest with a 75% confidence interval. The quantitative measure of dissimilarity may be sufficient to identify an event of interest with an 85% confidence interval. The quantitative measure of dissimilarity may be sufficient to identify an event of interest with a 95% confidence interval.

In some embodiments, the system may include a transmitter wherein a remedial action may include sending, via the transmitter, a notification to an administrator. An administrator of the abnormal consumption detection system that may be associated with a distributed water infrastructure may be an individual that has been designated responsible for monitoring and managing the system. This individual may also have been given authorization to access the system directly and interact with it through remote communication. In other embodiments, it is envisioned that the individual may have a range of different access and responsibilities. The administrator may be an individual who receives all notifications from the system and may be responsible for responding appropriately in every eventuality. In other embodiments, the administrator may be a homeowner that receives a notification, and instructs a third-party to respond appropriately in every eventuality.

In some embodiments, a system for detecting abnormal water consumption may send a notification, and the sending of the notification may occur through remote communication. The term remote communication includes any system that detects abnormal consumption and can notify the administrator that abnormal consumption has been detected. In some aspects, sending a notification by remote communication may involve sending a message through a communication network to at least one remote computing device. The remote communication device may be accessed by an administrator. The communication network may be a cellular, or a wired or wireless network. The message may be conveyed through an SMS, an e-mail, or an indication on a website, or through a notification on a mobile application, and the computing device may be a desktop computer, a laptop computer, or any mobile computer.

In some embodiments, at the time of classification, the normal water event profiles are not associated with a particular water appliance in the distributed water system. In such embodiments, a normal water usage for a distributed water infrastructure may include a plurality of unassigned normal water profiles.

In some embodiments, the system for detecting abnormal water consumption may include at least one processor that is configured to enable association between a water event and an appliance in the distributed water system. The system for detecting abnormal water consumption may include at least one processor that is configured to enable association between each time-based water event profile and each normal event profile and a specific appliance in the distributed water system. In some embodiments, each time-based water event profile and each normal event profile may be associated with a group of appliances in the distributed water system. The at least one processor may be configured to enable identification of a specific appliance based on at least one parameter selected from an average flow rate, an initial flow rate, a total volume associated with a current water event profile, a noise in signals indicative of water usage, and a change in the rate of water usage.

It is contemplated that a water appliance may be any water-consuming device that may be physically connected to some distributed water infrastructure. In some embodiments, a water appliance consumes water. By way of example, a specific appliance may be a mechanical water outlet such as a tap, sink, valve, or shower head. Other examples may include more complex mechanical devices such as a toilet, or an electro-mechanical device such as a dishwasher, washing machine, water filtration system, irrigation system, air-conditioning system, or any other automatic or semi-automatic water consumer. A group of appliances may be a row of identical toilets in a bathroom.

In some embodiments, at least one processor may be configured to enable association between stored, and new, water event profiles to a known appliance connected to the distributed water infrastructure. Association may be carried out automatically by the processor using prior knowledge about the water event profiles of specific appliances. Association may be carried out semi-automatically whereby the processor uses prior knowledge of water event profiles to suggest the most likely association, which an individual may confirm. Association may be carried out manually whereby an individual associates the water event profiles with known appliances connected to the water system and submits this association to the processor.

In some embodiments, a normal water event may be determined to substantially correspond with a known water event profile for a specific water appliances, or group of water appliances, in the distributed water system. In other embodiments, it may be not necessary for a water event to substantially correspond with a normal water event that may be associated with a specific water appliance, such as when a specific appliance malfunctions a minimal correspondence may be sufficient to match a specific water appliance with a current water event profile. In additional embodiments, the water event may not be associated with a specific water appliance at the time of classification, but may be associated with a specific water appliance at a later time. The time of classification may be the time when a current water event profile is classified either as a normal event or as an abnormal event.

In some embodiments, the at least one processor may be configured to compare water events, which may include pattern recognition. Pattern recognition describes a process of grouping any number of events into groups that share similar characteristics. In some embodiments, pattern recognition describes a process of comparing a new signal, which may originate from a source and that may have been sensed by a sensor, with previously sensed typical signals originating from the same source in order to determine if the new signal may be similar to one of the typical signals and therefore can be classified as a recognized pattern. In some embodiments, patterns may be learned by manual identification or through computation using any machine learning technique whether supervised, unsupervised, or semi-supervised, and recognition may be achieved by comparing new signals with learned signals using any measure of similarity or dissimilarity calculated in the feature space of the signals where the feature space describes the quantitative representation of the signals, obtained through a mathematical transformation of the original signal data.

In some embodiments, at least one processor may be configured to receive from an end user an indication of a specific appliance in use, and to store in an associated manner, the specific appliance with a water event profile associated with the specific appliance. The at least one processor may be configured to identify a water user associated with the water event profile. Specific appliances may have a range of modes of operation that may vary for specific individuals. For example, an individual may take a shower at a certain time of day, for a certain duration, and may use a specific shower in a certain location in the distributed water infrastructure. The at least one processor may be configured to compare normal water event profiles to the current water event profile and associate the water usage with a particular user based on a characteristic associated with a user. For example, a characteristic associated with a user may be a period of time where a user is the only user using the distributed water infrastructure. In some embodiments, a characteristic may be a duration that a water event profile may be used or a sequence that a group of devices are used within a period of time. For example, an individual may be identified by a characteristic time between a toilet and sink being used, or the duration that a sink is used. In such embodiments, the processor may not be configured to associate water event profiles with a specific appliance, such that use of the toilet and sink are associated with water event profiles that are unique but not assigned to specific devices. The at least one processor may be configured to compare normal water event profiles to the current water event profile, identify a specific appliance that may be used, and associate the water usage with a particular user.

In some embodiments, the at least one processor may be configured to determine operation of the specific water appliance when the current water event profile deviates from the normal event profile by less than a predetermined amount. The at least one processor may be configured to identify a partially malfunctioning appliance. The at least one processor may be configured to associate a current water event profile with a normal water event profile if the match is within a predetermined amount or percentage.

In some embodiments, the at least one processor may be configured to determine that the specific appliance may be in use before use of the specific appliance is terminated. For example, the at least one processor may be configured to identify the use of a shower by comparing a current water event profile with a stored shower normal water event profile, which may be based on an initial flow rate and average flow rate, such that after the shower is initiated the at least one processor may identify the appliance in use before the shower completes. The use of a washing machine may be identified after the end of a first cycle, such that the subsequent cycles are associated with the washing machine.

The at least one processor may be configured to determine from the current water event profile a specific appliance that may be leaking, wherein the remedial action may include providing information to an end user identifying the specific appliance. The at least one processor may be further configured to provide to the end user information about a characterization of the leaking of water. A characterization of the leaking of water may be any information regarding the appliance and/or the leak. The information may be stored in association with the water event profile for the specific application. The information may be identified from the at least one sensor contemporaneously with a detection of a leak. For example, the characterization of the leaking of water may be the flow rate of the leak, a stored location of an appliance that may be leaking, a total volume of water that has leaked, and an identification of the last appliance that was in use.

In some embodiments, the at least one processor may be configured to initiate the remedial action when a duration of use of a specific appliance exceeds a duration of an associated normal water event profile. The at least one processor may be configured to determine that the specific appliance may be in use before use of the specific appliance is terminated, such that a remedial action can be initiated if a usage exceeds a predetermined range or learned range of typical water usage. In some embodiments, each normal water event profile may be assigned, by an administrator, a duration of use. The at least one processor may be configured to determine a range of duration of use of a specific appliance, by identifying a specific appliance, tracking the duration of water consumption each time the specific appliance was in use, and determining a representative range of durations.

A distributed water infrastructure may experience abnormal water events that may fall within a set of categories, such as an irrigation leak, a drip leak, and a pipe burst. Certain abnormal water events may have defining characteristics that may be used as the basis for constructing abnormal water event profiles. These water event profiles may be stored in memory, such that when a current water event profile does not match a normal water event profile, the current water event profile may be matched versus stored abnormal water event profiles. The at least one processor may be configured to compare the at least one current water event profile with abnormal water event profiles stored in memory and to initiate remedial action when a substantial match is determined.

A distributed water infrastructure may experience abnormal water events that are more likely to cause a significant amount of damage. For example, a high flow leak on an upper flow may be more likely to cause damage than a low flow leak outside. The at least one processor may be configured to distinguish between abnormal operation of appliances unlikely to cause damage and abnormal operation of appliances likely to cause damage, wherein the remedial action may include closing a valve when abnormal operation likely to cause damage is detected. In some embodiments, each time-based water event profile and each normal event profile may be associated with a specific damage indicator. In certain embodiments, an end user may indicate certain specific appliances that are considered high risks for leaks, and the system may be configured to identify when a specific appliance is in use.

Figure 2A:
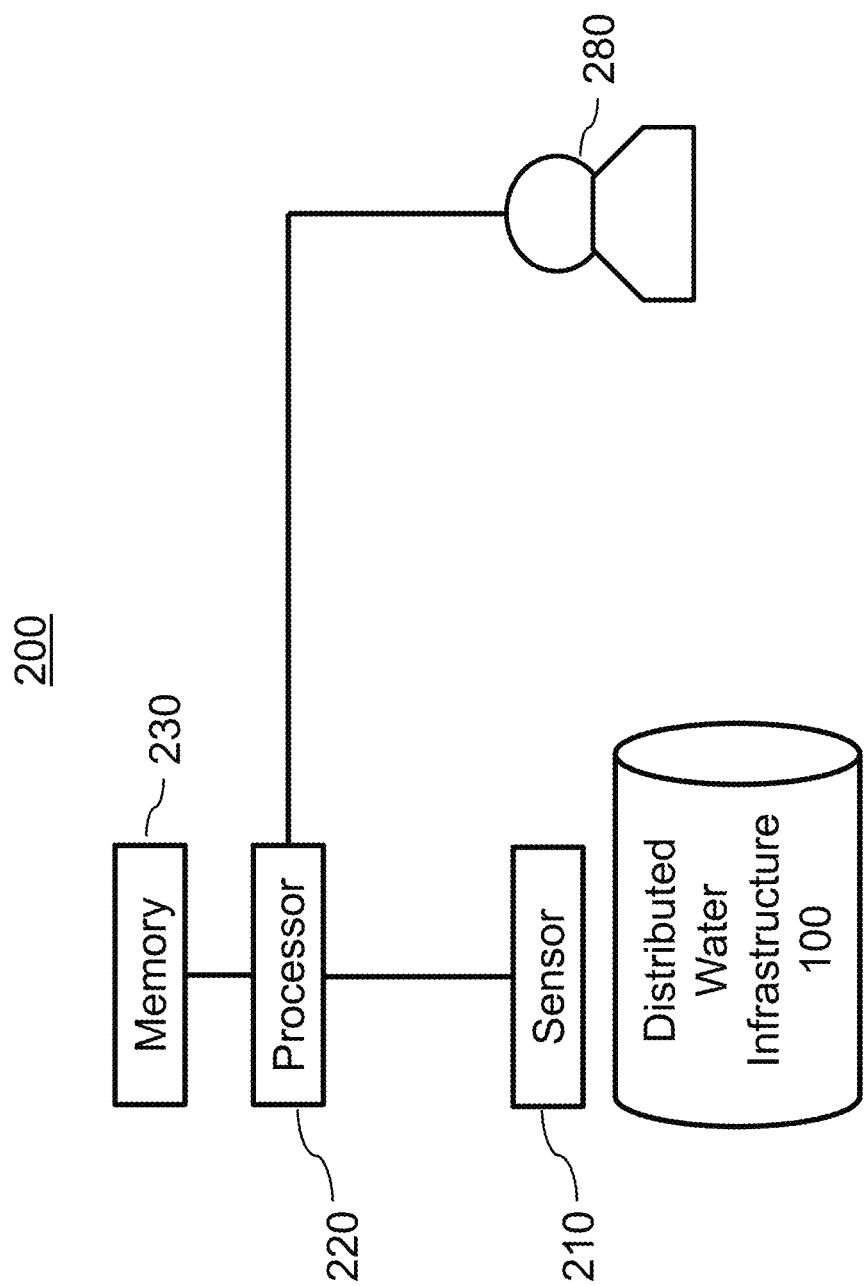
FIGS. 2a and 2b illustrate exemplary systems for detecting the consumption of liquids.

FIG. 2a illustrates an exemplary system 200 for detecting the consumption of liquids. The components of system 200 discussed herein are intended to be illustrative. In some embodiments, system 200 may be implemented with one or more additional components not described, and/or without one or more of the operations discussed. Additionally, the configuration of the elements in which the components of system 200 are illustrated in FIG. 2a, and FIG. 2b, and described herein is not intended to be limiting.

Exemplary system 200 may be configured to carry out a procedure of gathering measurements of liquid consumption according to aspects of the present disclosure. As shown in FIG. 2a, one or more sensors may be provided in the system. In some embodiments, sensors may comprise any sensor that measures the consumption of water, including the non-limiting examples of a flow sensor, a sonic water sensor, and a pressure sensor. The system may include more than one sensor. For example, sensor 210 may be attached at some point in a distributed water infrastructure 100. In some embodiments, sensors may be configured to gather information used to generate statistical and/or event-based data regarding water consumption and relay the information to an end user 280.

As shown in FIG. 2*a*, at least one processor may be provided in the system. In some embodiments, processor 220 may be configured as a part of a computer provided with a central processing unit (CPU) and memory 230. In some embodiments, memory may include at least one of the non-limiting examples of a random access memory (RAM), and a read-only memory (ROM). For example, processor 220 may read out a program corresponding to detecting abnormal consumption in a distributed water infrastructure, load it into the RAM, and cause the CPU to perform a process corresponding to receiving, from sensor 210, signals indicative of water usage in the distributed water infrastructure. The program may be downloaded via a communication network or may be provided as stored in a storage medium in memory 230.

Figure 2B:
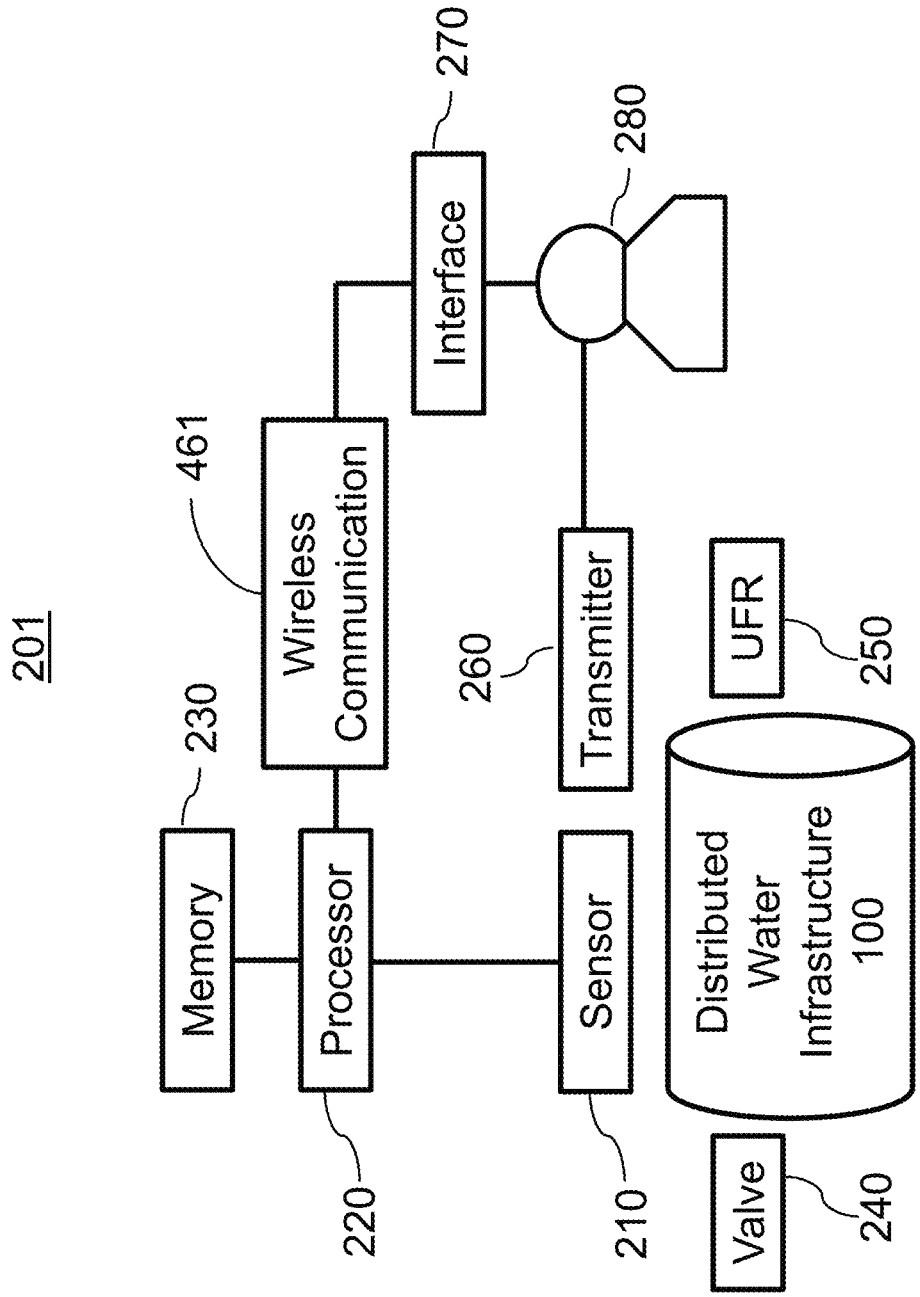

As shown in FIG. 2*b*, an exemplary system 201 may optionally include further components. It is explicitly considered that each additional component in FIG. 2*b* may be included, individually or in some combination, in a system such as illustrated in FIG. 2*a*. In some embodiments, a system may include a valve 240. Valve 240 may be configured to halt the flow of water after receiving a signal from at least one processor 220. The system may include an unmeasured flow reducer 250. The system may include a transmitter 260 and a wireless communication device 261. The system may include a user interface 270. User interface 270 allows a user to interact with the system, and may include a GUI, mechanical controls, electronic controls, electronic interface, display, etc. Processor 220 may be configured to send an alert to an end user 280.

In some embodiments, the measurement of water usage may be performed by any one of the systems described herein, and/or the measure of water usage may be performed by a third-party water measuring device. The measurement of water usage may be performed by separate devices distributed by distance, wherein the processing operations may be performed locally or at a central location. The processing operations may be performed in real time, and/or at a later time. The processing operations may also be provided by distributed parallel or cloud computing infrastructures with data and results transported to the cloud or parallel processor using wireless or wired networks.

In accordance with the present disclosure, some of the embodiments described herein provide examples of the novel benefits provided by event-based leak detection systems and methods. In some embodiments, a measurement of the number of liters consumed as a function of time may be transformed into a water usage pattern that has a particular fingerprint or water usage pattern. A water usage pattern may be determined by any method consistent with identification herein, such as the non-limiting examples of: event-based threshold method, guided machine learning, or automatic machine learning. Water usage pattern determination may be assisted by a neural network, whereby a system may progressively improve performance to determine, identify, and compare water usage patterns by considering examples. In some embodiments, a neural network may be used without task-specific programming. For example, a system may learn (without a specific program directed to the granular task of comparing water usage patterns) to differentiate between water usage patterns, by considering exemplary water usage patterns that are known to be different.

In various alternative methods, detecting the manner of consumption of liquids may be implemented by alternative methods of receiving water information, and employing event-based leak detection systems and methods to provide granularity of water usage to an end user.

Figure 3:
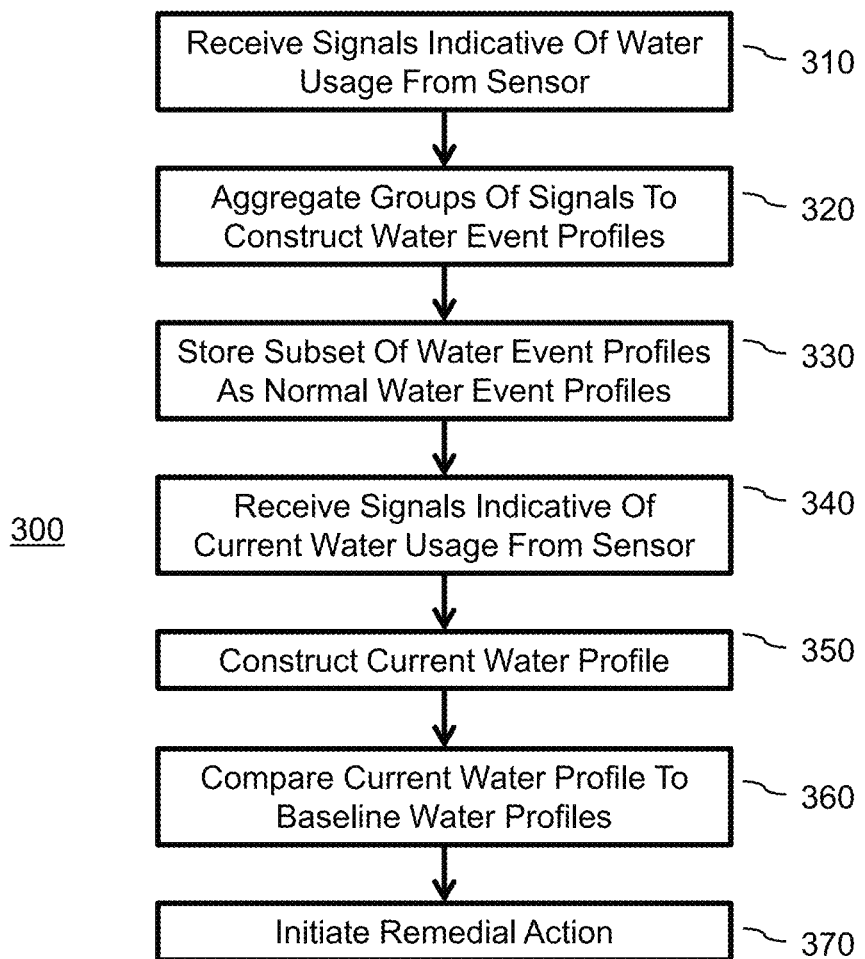
FIG. 3 illustrates an exemplary method for detecting the consumption of liquids.

FIG. 3 illustrates an exemplary method 300 for detecting the consumption of liquids. The operations of method 300 discussed here are intended to be illustrative. In some embodiments, method 300 may be implemented with one or more additional operations not described, and/or without one or more of the operations discussed. Additionally, the order in which the operations of method 300 are illustrated in FIG. 3 and described herein is not intended to be limiting.

In some embodiments, method 300 may be implemented in one or more processing devices (e.g., a digital processor, an analog processor, a digital circuit designed to process information, an analog circuit designed to process information, a state machine, and/or any other mechanisms or types of processors for electronically processing information, including any processors described herein). The one or more processing devices may include one or more devices executing some or all of the operations of method 300 in response to instructions stored electronically on an electronic storage medium. The one or more processing devices may include one or more devices configured through hardware, firmware, and/or software to be specifically designed for execution of one or more of the operations of method 300.

In some embodiments, at operation 310, at least one processor may be configured to receive from at least one sensor associated with the distributed water infrastructure signals indicative of water usage in the distributed water infrastructure. At operation 320, at least one processor may be configured to aggregate groups of signals to construct a plurality of time-based water event profiles, each water event profile containing a distribution of water usage indicators over time. At operation 330, at least one processor may be configured to store a subset of the plurality of water event profiles in memory as normal water event profiles. At operation 340, at least one processor may be configured to receive from the at least one sensor, signals indicative of current water usage in the distributed water infrastructure. At operation 350, at least one processor may be configured to construct, from the signals indicative of current water usage, at least one current water event profile. At operation 360, at least one processor may be configured to compare the at least one current water event profile with normal water event profiles stored in memory. At operation 370, at least one processor may be configured to initiate remedial action if the at least one current water event profile does not substantially correspond to normal water event profiles stored in memory.

An aspect of some embodiments may include a system for leak detection, water damage prevention, water savings, and the control of a water consumer's water system. The system may comprise a water flow meter sensor and solenoid valve inside a standard water meter base. The system may be an install-and-forget system that connects a water system to the Internet. The system may enable alerting, monitoring, and control from a mobile device or website, or from the system itself. The system may comprise a manual override lever that enables a water consumer to deactivate the system's ability to shut down water flow. The override may still allow alerting a water consumer regarding abnormal water consumption, but the system might not shut down water flow. The system may also comprise a water inlet, which may connect the system to a distributed water infrastructure. The system may also comprise a system base that may contain a metering unit and solenoid valve. The system may also comprise a status and control panel, which may display the system status and enable a water user to permit water to flow through the distributed water infrastructure if the system has been closed due to a remedial action.

An aspect of some embodiments may include a system that may include an artificial intelligent system (comprised of a learning mechanism and related algorithms) that continually monitors the water consumption of a water consumer's property. In some embodiments, a system may detect abnormal water flow and immediately alert a water consumer via text message to a mobile phone. The system may be connected to the Internet such that a website and/or application may provide detailed charts and graphs indicating water consumption, including, for example, on an hourly basis. The system may be able to shut down water flow. The system may operate independently. Upon identifying excess water consumption, in either open or hidden areas, during day or night, inside or outside a property, the system may alert an end user via text message to a mobile device.

According to user preferences, the system may either shut down the main water valve automatically or allow a water consumer to shut down the water manually from a mobile device. The system may also enable an end user to remotely override the shutdown from a mobile device. In some embodiments, a system may use its water flow meter sensor and its artificial intelligence algorithms to learn the water consumption patterns on a property (e.g., in an adaptive mode). The system may collect all the signatures of water usage patterns to be used as a baseline for detecting abnormal water consumption.

In some embodiments, for the first month after the system is installed, the system may monitor normal water consumption rates and patterns of a property in order to set up the baseline criteria to be used later as the initial baseline for identifying abnormal water consumption. During this month, the system might not shut down a property's water.

In some embodiments, an end user may deactivate the system's learning mechanisms and instead, use a personal website to enter the water usage threshold values according to any schedule that one may want by specifying various times of day, days of week and holidays, and the water usage thresholds that will determine when the water may be shut down.

In some embodiments, the system may include a home and away mode. The system may enable remotely setting restrictive behavior when an end user is away from a property for more than 24 hours (such as during a vacation).

In some embodiments, the system may enable an end user to define fixed thresholds and functionality per time of day and weekends. When the system detects moderate or major water consumption, it may immediately alert a water consumer via text message, mobile app, and website. A water consumer may have the option to remotely override its decision to shut the water from their mobile app, website, or using their faucet. If a water consumer does not override the system's decision, then the system may automatically shut down the water flow. The system may enable a water user to reopen a water value remotely.

In some embodiments, if the system continues to detect moderate or major abnormal water consumption after an end user has overridden the system's automatic shutting down of water, the system may send another alert after 30 minutes or a determined time period, but it will not shut down the water again.

In some embodiments, the systems and methods according to the present disclosure may categorize the severity of abnormal water events. The systems and methods may take different actions depending on the category. In some embodiments the system may categorize abnormal water flow rates into three categories: minor, moderate, and major.

Minor abnormal water consumption may be equivalent to a tiny leak or water dripping from a faucet. Notably, minor leaks can cause major damage over time in the form of mold and building infrastructure damage. In some embodiments, a system, upon detecting minor abnormal water consumption, may send a message to a mobile device notifying about the abnormal water consumption. If the water consumption continues, then another message may be sent after a day, after a week, and after a month. In some embodiments, no additional text messages might be sent to a mobile device after that.

In some embodiments, after a minor alert is sent, the system may ignore all additional minor abnormal water consumption of the same magnitude until after the current problem is resolved. This may mean, for example, that the minor water leak must be fixed before the system can detect additional minor water leaks of the same magnitude. However, if a larger water consumption abnormality is detected, the system may alert an end user.

Moderate abnormal water consumption may be equivalent to a flow from a slightly open faucet. The difference between moderate and major abnormal water consumption may depend on the flow rate. The larger the abnormal water consumption, the quicker the system's reaction time may be to shut down the water flow via a valve and sending notifications and re-notifications. Some abnormal water consumption may not fall into this category. In some embodiments, if there is a constant flow for a period of time at some rate, the constant flow may be categorized as abnormal water flow.

In some embodiments, a system may be configured to send an alert to a device, website and mobile application that the system has shut down the water, or may shut down the water. The system may be configured to provide a chance to override a shutdown action.

Major abnormal water consumption event may be equivalent to the flow from a completely open faucet or more serious event. According to preferences, a system may automatically and immediately shut off water in order to prevent major damage, while providing an end user with a variety of remote options for overriding the system's decision to shut down the water. The system may be configured to provide a chance to override its decision to shut down the water from a mobile device.

In some embodiments, a system may enable a water consumer to remotely monitor the ongoing consumption of water (monthly, weekly, daily and hourly), to control the water system and to see water system alerts. A device may be installed on a property in order to analyze ongoing water consumption and to produce routine consumption data. Consumption data may be displayed hourly, daily (e.g., last 7 days of consumption), weekly, and monthly. In some embodiments, a mobile app may enable a water consumer to get water system alerts directly from a mobile device, to remotely control a water system, and to monitor ongoing consumption of water, on a monthly, weekly, daily, and hourly basis.

Exemplary Embodiments of Remote Valve
Reopening Following Abnormal Consumption

The present application provides for remote valve reopening following a potential detected leak. A benefit of some embodiments of the present disclosure may be systems and methods may utilize an integrated leak detection system with an application that permits remote valve reopening via a remote communication device.

An aspect of some embodiments may include an integrated abnormal consumption detection system for a distributed water infrastructure. Such a system may include an electronically controllable valve. An electronically controllable valve may be an electromechanical device used to control fluid flow by varying the size of the flow passage as directed by a signal from a controller. The flow passage may be fully closed. Automatic control valves may be open or closed by sending an electrical signal from a controller to a solenoid that causes a valve to open or close.

In some embodiments, an integrated abnormal consumption detection system for a distributed water infrastructure may include a communication transmitter. The communication transmitter may be a remote communication transmitter. A communication transmitter may be any electronic communication device used to transmit information between at least two devices. For example remote communication transmitter may transmit information via a wire or remote communication network.

In some embodiments, an integrated abnormal consumption detection system for a distributed water infrastructure may include a communication receiver. The communication receiver may be a remote communication receiver. A communication receiver may be any electronic communication device used to receive information between at least two devices. In some embodiments, a remote communication receiver may receive information via a wire or remote communication network.

In some embodiments, an integrated abnormal consumption detection system for a distributed water infrastructure may include at least one consumption sensor for measuring water flow information associated with the distributed water infrastructure. A sensor may be any of the sensors described herein. The sensor may be configured to measure any physical property that indicates the quantity of water per unit of time that flows through a distributed water infrastructure. The water flow information may be measured in liters per hour or in gallons per hour. In some embodiments, flow information may include at least one of flow rate and flow volume. Flow information may be gathered from a signal that is sent every time the sensor measures a given amount of volume has passed the sensor.

In some embodiments, an integrated abnormal consumption detection system for a distributed water infrastructure may include at least one processor configured to determine from the water flow information, obtained from the sensor, a potential abnormal consumption associated with the distributed water infrastructure. Abnormal consumption may be defined by a mathematical function that characterizes a known, undesirable consumption profile, which may then be compared with a sensed consumption profile in order to identify an abnormality. The abnormal water consumption may be characterized by a sensed water consumption profile. Abnormal water consumption may refer to any water consumption profile sensed in a distributed water infrastructure that deviates significantly from one or more pre-learned water consumption profiles that characterize normal consumption in that water system. In some embodiments, an abnormal water consumption profile should differ significantly from the known water consumption profiles. The significant deviation may be measured quantitatively by comparing the sensed water consumption profile with each of the pre-learned consumption profiles using any suitable distance measure of similarity or dissimilarity. The deviation of the sensed consumption profile from a pre-learned consumption profile may be considered significant when the distance of the sensed consumption profile is beyond the acceptable distance limits defined for the pre-learned consumption profile.

In some embodiments, an integrated abnormal consumption detection system for a distributed water infrastructure may automatically close a valve, without human intervention when a potential abnormal consumption is determined. The system may transmit, via the remote communication transmitter to a remote administrator, information about the potential abnormal consumption to enable an administrator to decide based on the transmitted information whether to reopen the valve.

In some embodiments, an integrated abnormal consumption detection system for a distributed water infrastructure may wait for confirmation from an administrator before closing a valve. The integrated abnormal consumption detection system for a distributed water infrastructure may receive from the administrator via the remote communication receiver a control signal to close the valve.

In some embodiments, an integrated abnormal consumption detection system for a distributed water infrastructure may be configured to automatically reopen the valve after a period of time. The at least one processor may be configured to reopen the valve if information from the at least one sensor determines an abatement of the potentially abnormal water condition.

In some embodiments, an integrated abnormal consumption detection system for a distributed water infrastructure may send an alert that may assist the end user in determining whether to open or re-open the valve. The alert information may include at least one of flow rate, flow volume, and an indication of a water-consuming appliance likely to be malfunctioning.

In some embodiments, an integrated abnormal consumption detection system for a distributed water infrastructure may receive from an administrator via a remote communication receiver a control signal to reopen the valve. The administrator may choose to re-open the valve despite information about the potential abnormal consumption, and the valve would be reopened.

A control signal may refer to a pulse of electricity, or any other transmitted signal, that represents a control command generated by a controller. Such a pulse may travel over a network or a computer channel using wired or wireless communication. At least one of the remote communication transmitter and the remote communication receiver may be wireless.

In some embodiments, an integrated abnormal consumption detection system for a distributed water infrastructure may include an integrated remote communication transmitter and remote communication receiver. The two communications units may be combined in one electronic unit that unites both the transmitting and receiving function. In another embodiment, the remote communication transmitter and remote communication receiver may not be integrated. At least one of the remote communication transmitter and the remote communication receiver may be wireless. The term wireless, or wireless communication, refers generally to the transfer of information between two or more points that are not connected by an electrical conductor. In wireless communication, information may be transferred over both long and short distances. Examples of wireless communication may include, but are not limited to, GPS units, radio receivers, satellite television, LTE, Wi-Fi, and Bluetooth.

In some embodiments, the at least one consumption sensor may include at least two sensors, wherein the at least one processor may be further configured to receive water flow information from at least two sensors. A sensor according to the present disclosure may include a sensor hub. A sensor hub may receive information from at least one sensor. The sensor hub may be a device that comprises a microcontroller unit and interfaces, and may integrate data from different sensors and process the data. Examples of the different sensor data types that may be incorporated into a sensor hub include flow rate, flow pressure, and temperature. Further, a sensor may measure other water quality properties such as pH, conductivity, fluorine concentration, and the presence of a biofilm.

In some embodiments, an integrated abnormal consumption detection system for a distributed water infrastructure may include a valve, wherein the valve is closed or opened based on a measurement of or from a sensor. A measurement from a sensor may be any electrical signal generated by a sensor and delivered to a sensor hub or controller. Such electrical signals may be proportional to physical properties, such as, but not limited to, pressure, water flow rate, acceleration, and temperature.

In some embodiments, an integrated abnormal consumption detection system for a distributed water infrastructure may include at least one processor configured to determine from the water flow information an appliance likely associated with the abnormal consumption and to identify a subsystem valve associated with the appliance, wherein automatically closing the valve may include closing the subsystem valve to isolate the appliance from at least a portion of the distributed water infrastructure.

The system may include a transceiver that integrates the remote communication transmitter and the remote communication receiver. The system may include at least one processor configured to ignore the potential abnormal consumption, store in memory the water flow information associated with the potential abnormal consumption, and take no remedial action when the potential abnormal consumption is below a shut-off threshold.

An aspect of some embodiments may include an abnormal water consumption detection system for a distributed water infrastructure. In accordance with the present disclosure, a system for detecting flow of a fluid may include at least one processor. The at least one processor may include any physical device having an electric circuit that performs a logic operation on input or inputs. For example, a processor may include one or more integrated circuits, microchips, microcontrollers, microprocessors, all or part of a central processing unit (CPU), graphics processing unit (GPU), digital signal processor (DSP), field-programmable gate array (FPGA), or other circuits suitable for executing instructions or performing logic operations. The instructions executed by a processor may, for example, be pre-loaded into a memory integrated with or embedded into the processor or may be stored in a separate memory.

More than one processor may be used for any function. Each processor may have a similar construction or the processors may be of differing constructions that are electrically connected or disconnected from each other. For example, the processors may be separate circuits or integrated in a single circuit. When more than one processor is used, the processors may be configured to operate independently or collaboratively. The processors may be coupled electrically, magnetically, optically, acoustically, mechanically, or by other means that permit them to interact.

In one embodiment, a processor may be a data processor, a personal computer, or a mainframe for performing various functions and operations. The system for detecting abnormal consumption of water in a distributed water infrastructure may be implemented, for example, by a general purpose computer or a data processor selectively activated or reconfigured by a stored computer program, or may be a specially constructed computing platform for carrying out the features and operations described herein. Moreover, the system for detecting abnormal consumption of water in a distributed water infrastructure may be implemented or provided with a wide variety of components or systems, including one or more of the following: central processing units, co-processors, memories, registers, or other data processing devices and subsystems.

In some embodiments, an integrated abnormal consumption detection system may include at least one processor configured to receive, from at least one sensor associated with the distributed water infrastructure, water usage information for the distributed water infrastructure. The system may include at least one processor configured to determine, from the water usage information, an event likely to be an abnormal consumption within the distributed water infrastructure. The system may include at least one processor configured to send, via a transmitter, an alert message to an administrator notifying the administrator of the likely abnormal consumption, and providing to the administrator data associated with the likely abnormal consumption. The system may include at least one processor configured to receive from the administrator via a receiver a command, the command being chosen from a group consisting of an ignore command and a remedial action command. The system may include at least one processor configured to permit water to flow through a valve after the ignore command is received.

In some embodiments, at least one processor may be configured to close a valve in response to receipt of the remedial action command. At least one processor may be configured to store a profile of the likely abnormal consumption associated with the ignore command, and to avoid sending a subsequent alert message to the administrator at a later time when the profile may be detected again. The data associated with the likely abnormal consumption provided to the administrator may include at least one of flow rate, flow volume, and an indication of an identity of an appliance likely to be malfunctioning. Data provided to the administrator may include location information of the appliance likely to be malfunctioning.

In some embodiments, the at least one processor may be configured to store in memory appliance information including at least one of location information and identity information for at least one water-consuming appliance in the distributed water infrastructure, associate the likely abnormal event with appliance information, and send to the administrator via the transmitter the appliance information when a likely abnormal event is determined. The at least one processor may be configured to predict identities of a plurality of water appliances in the distributed water infrastructure based on the water usage information.

In some embodiments, the processor may be configured to provide, via the transmitter, updated data to the administrator following the message in order to enable the administrator to assess ongoing severity. The at least one processor may be configured to determine a sub-system valve that isolates at least one appliance likely associated with an abnormal water event from other portions of the distributed water infrastructure, and to close the sub-system valve in response to the remedial action command. The at least one processor may be configured to close the valve if a command is not received from the administrator within a predetermined time period following message transmission to the administrator.

An aspect of some embodiments may include an abnormal consumption detection system for a distributed water infrastructure. In some embodiments, the system may comprise at least one processor configured to determine from water flow information obtained from at least one sensor a potential abnormal consumption associated with the distributed water infrastructure. The at least one processor may be configured to determine, from the water flow information, an identity of a water-consuming appliance associated with the potential abnormal consumption. The at least one processor may be configured to automatically close a valve without human intervention, which shuts off water flow to the determined water-consuming appliance.

In some embodiments, at least one processor may be further configured to transmit, via a remote communication transmitter to a remote administrator, information about the potential abnormal consumption to enable the remote administrator to decide based on the transmitted information whether to reopen the valve. The at least one processor may be further configured to receive from the remote administrator via a remote communication receiver a control signal to reopen the valve, despite the information about the potential abnormal consumption, and to reopen the valve in response to the control signal.

Figure 4A:
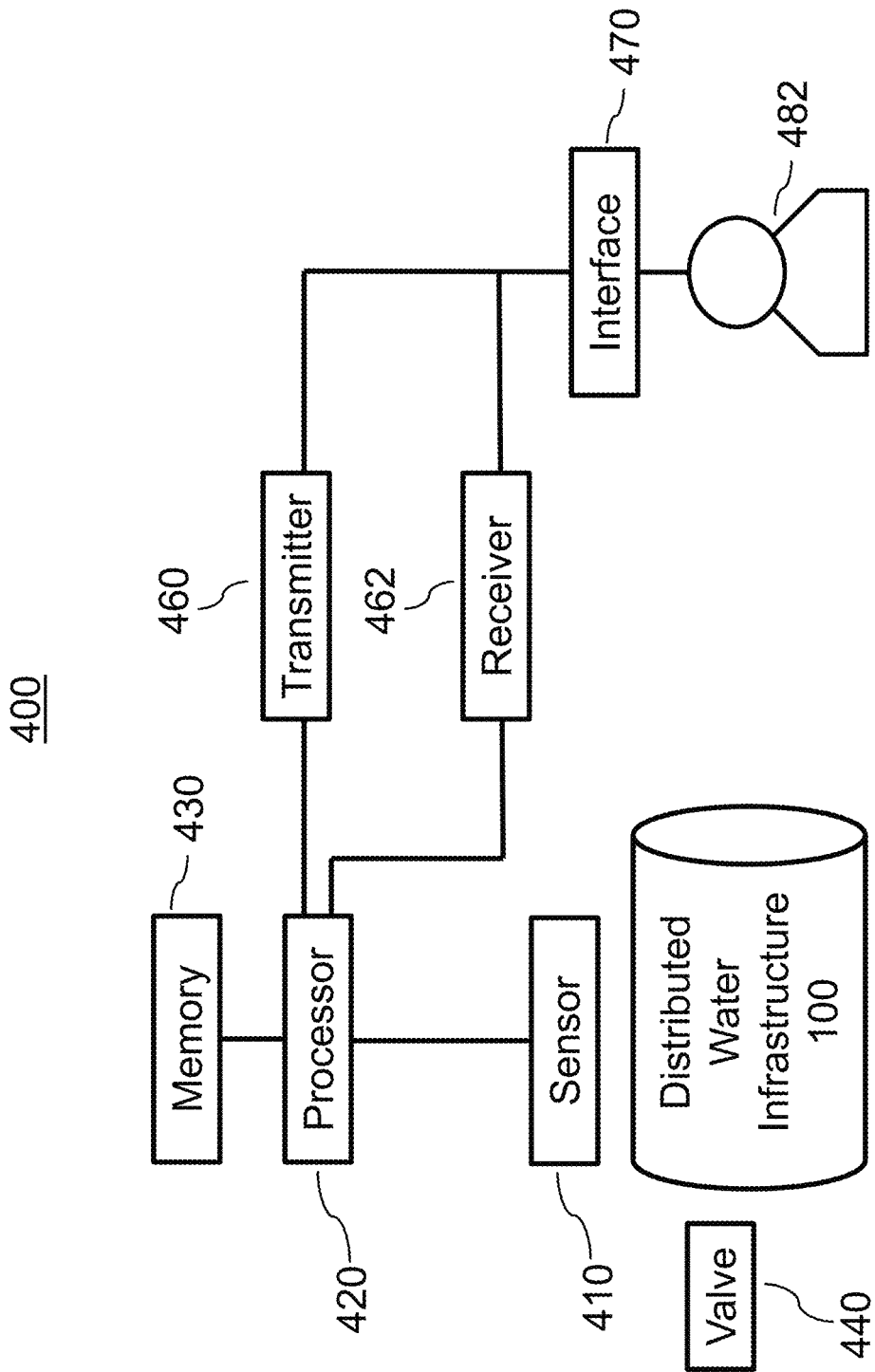
FIGS. 4a and 4b illustrate exemplary systems for remote valve reopening and/or automatic valve closure after the detection of abnormal consumption.

FIG. 4a illustrates an exemplary system 400 for remote valve reopening and/or automatic valve closure after the detection of abnormal consumption. The components of system 400 discussed herein are intended to be illustrative. In some embodiments, system 400 may be implemented with one or more additional components not described, and/or without one or more of the operations discussed. Additionally, the configuration of the elements in which the components of system 400 are illustrated in FIGS. 4a and 4b, and described herein, is not intended to be limiting.

Exemplary system 400 may be configured to carry out a procedure of remote valve reopening following potential detected abnormal consumption according to aspects of the present disclosure. As shown in FIG. 4a, one or more consumption sensors 410 may be provided in the system. In some embodiments, processor 420 may be configured as a part of a computer provided with a central processing unit (CPU). The system may include a controllable valve 440. Valve 440 may be configured to halt the flow of water after receiving a signal from at least one processor 420. The system may include a communication transmitter 460 and a communication receiver 462. A remote administrator 482 may send and/or receive information to and from communication transmitter 460 and communication receiver 462.

Figure 4B:
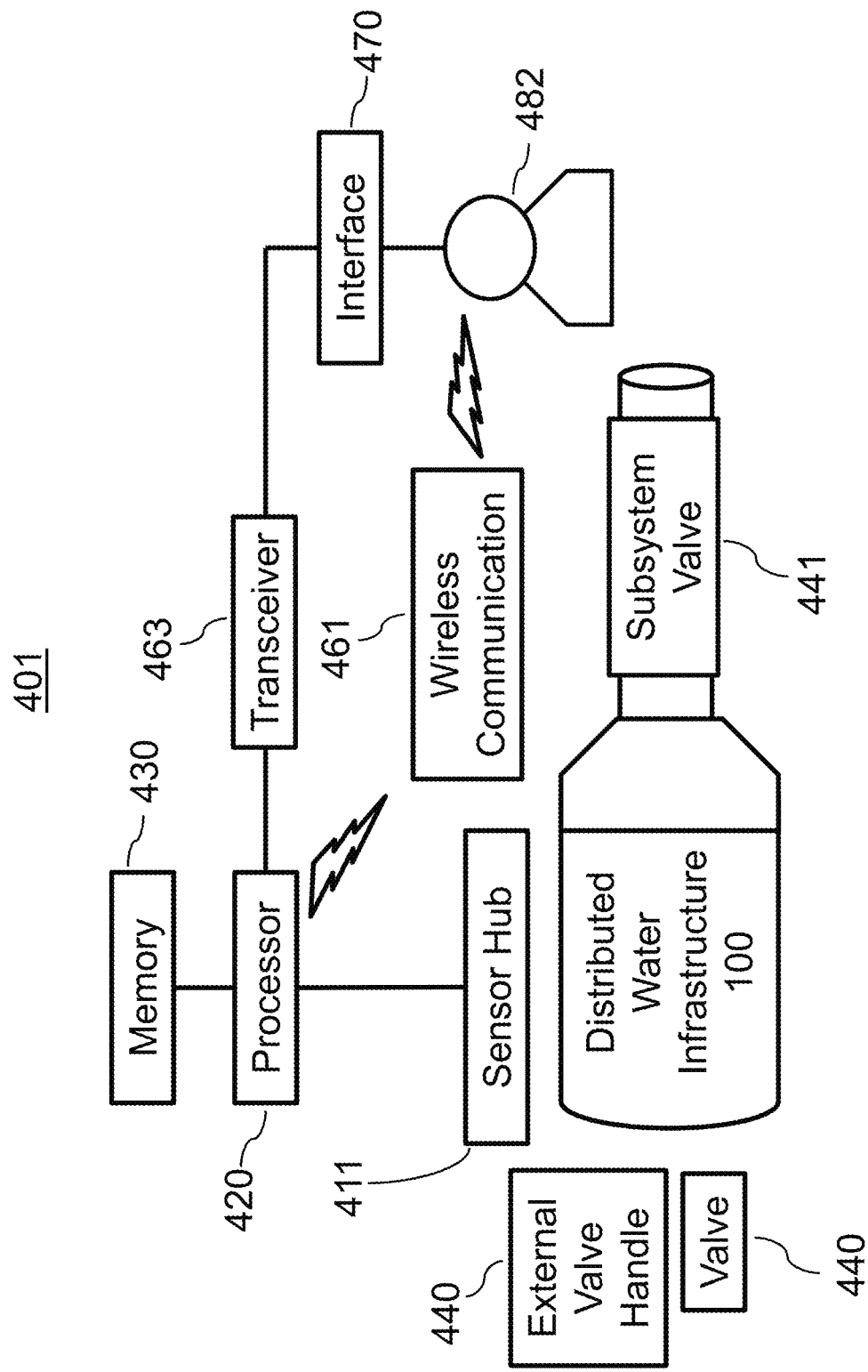

As shown in FIG. 4b, an exemplary system 401 may include other components. It is explicitly considered that each component in FIG. 4b may be included, individually or in some combination, in a system such as illustrated in FIG. 4a. In some embodiments, a system may include wireless communication. The system may include communication transceiver 463, which may combine communication transmitter 460 and communication receiver 462. Transceiver 463, transmitter 460, and receiver 462 may be wireless or wired. The system may include subsystem valve 441, which may be connected to another location in the distributed water infrastructure 100. The system may include exterior valve handle 442, which may allow for manual close of a valve 440. In some embodiments, a system may include sensor hub 411, which may include multiple sensors in addition to a consumption sensor 410.

Figure 5A:
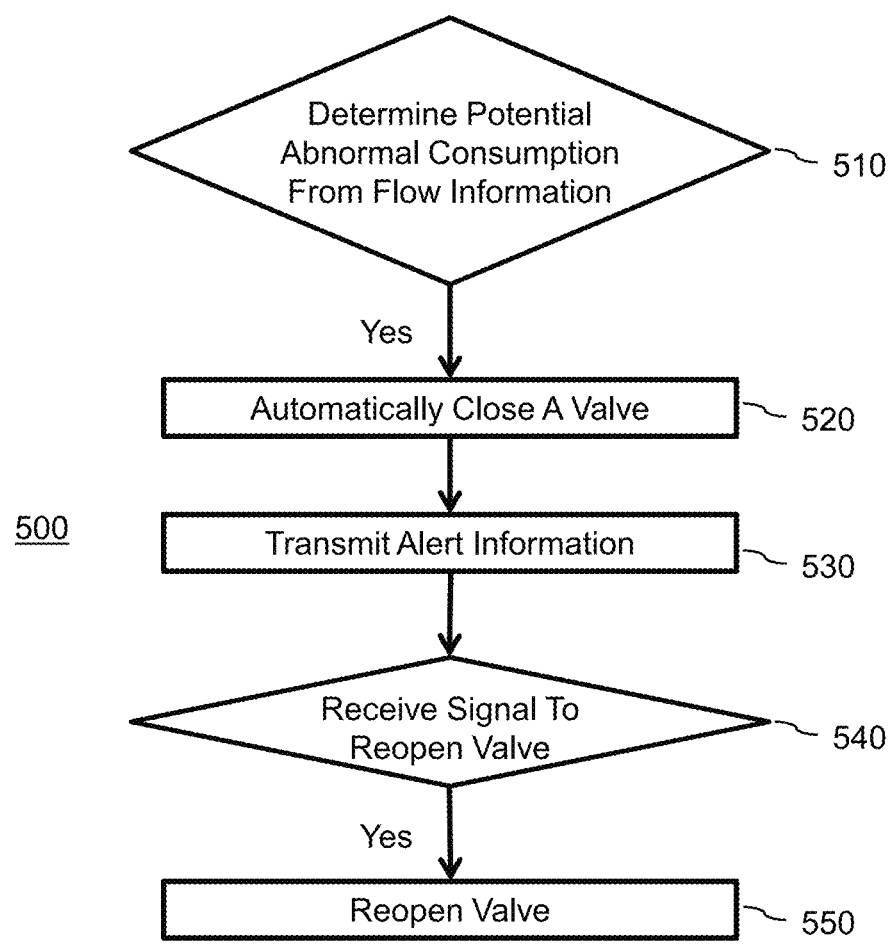
FIG. 5a illustrates an exemplary method for remote valve reopening and/or automatic valve closure after the detection of abnormal consumption.

FIG. 5a illustrates an exemplary method 500 for remote valve reopening and/or automatic valve closure after the detection of abnormal consumption. The operations of method 500 discussed herein are intended to be illustrative. In some embodiments, method 500 may be implemented with one or more additional operations not described, and/or without one or more of the operations discussed. Additionally, the order in which the operations of method 500 are illustrated in FIG. 5a and described herein is not intended to be limiting.

In some embodiments, method 500 may be implemented in one or more processing devices. The one or more processing devices may include one or more devices executing some or all of the operations of method 500 in response to instructions stored electronically on an electronic storage medium. The one or more processing devices may include one or more devices configured through hardware, firmware, and/or software to be specifically designed for execution of one or more of the operations of method 500.

In some embodiments, at operation 510, at least one processor may be configured to determine from the water flow information obtained from the at least one consumption sensor a potential abnormal consumption associated with the distributed water infrastructure. At operation 520, at least one processor may be configured to automatically close a valve, without human intervention, when the potential abnormal consumption is determined. At operation 530, at least one processor may be configured to transmit, via the remote communication transmitter to a remote administrator, alert information about the potential abnormal consumption to enable an administrator to decide based on the transmitted information whether to reopen the valve. At operation 540, at least one processor may be configured to receive from the administrator via the remote communication receiver a control signal to reopen the valve, despite the information about the potential abnormal consumption. At operation 550, at least one processor may be configured to reopen the valve.

Figure 5B:
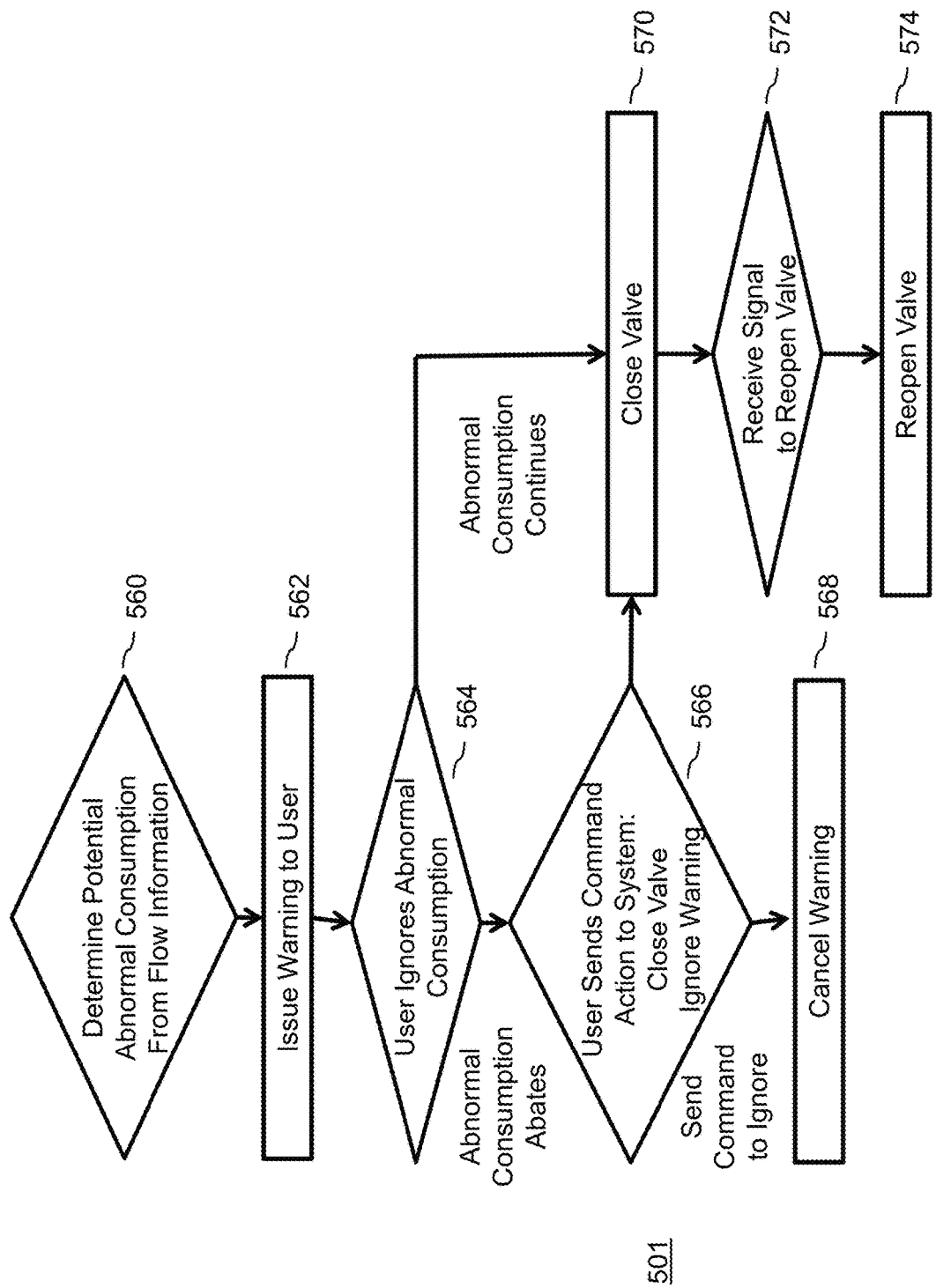
FIG. 5b illustrates an exemplary method for remote valve reopening and/or automatic valve closure after the detection of abnormal consumption including an option to ignore warnings of abnormal consumption.

FIG. 5b illustrates an exemplary method 501 for remote valve reopening and/or automatic valve closure after the detection of abnormal consumption. The operations of method 500 discussed herein are intended to be illustrative. In some embodiments, method 501 may be implemented with one or more additional operations not described, and/or without one or more of the operations discussed. Additionally, the order in which the operations of method 501 are illustrated in FIG. 5b and described herein is not intended to be limiting.

In some embodiments, method 501 may be implemented in one or more processing devices. The one or more processing devices may include one or more devices executing some or all of the operations of method 501 in response to instructions stored electronically on an electronic storage medium. The one or more processing devices may include one or more devices configured through hardware, firmware, and/or software to be specifically designed for execution of one or more of the operations of method 501.

In some embodiments, at operation 560, at least one processor may be configured to determine from the water flow information obtained from the at least one consumption sensor a potential abnormal consumption associated with the distributed water infrastructure. At operation 562, at least one processor may be configured to issue a warning to a user.

At operation 564, at least one processor may be configured to identify if the user has ignored the warning of an abnormal consumption. In some embodiments, a warning of an abnormal consumption may be in the form of at least one of a text message on a phone, a notification on a phone, and a notification on a web-based GUI. A user may ignore the warning of an abnormal consumption by taking no action, and a user may ignore the warning by dismissing a notification on their phone.

In some embodiments, where the user ignores a warning of an abnormal consumption, abnormal consumption may stop or abate. Accordingly, at operation 566, at least one processor may be configured to receive a command from a user to either close a valve or ignore the warning. If the user sends a command action to ignore a warning, then at operation 568 at least one processor may be configured to cancel the warning. Canceling a warning may include configuring a setting to indicate that future abnormal events matching the abnormal consumption will be ignored. In addition, or in an alternative, cancellation of a warning may include configuring a setting that indicates that a future water event matching the ignored abnormal consumption will be considered a type of normal water consumption. If, instead of sending a command to the system to ignoring a warning, the user sends a command action to close the valve, at operation 570, at least one processor may be configured to close the valve. At operation 572, at least one processor may be configured to receive a signal to reopen the valve, and at operation 574, at least one processor may be configured to reopen a closed valve.

In some embodiments, where the user ignores a warning of an abnormal consumption, abnormal consumption may continue. In the absence of a response from a user, at operation 570, at least one processor may be configured to close a valve. At operation 572, at least one processor may be configured to receive a signal to reopen the valve, and at operation 574, at least one processor may be configured to reopen a closed valve. A signal to reopen the valve may be sent by a user, but may also be sent automatically at a specified time. For example, an abnormal event that occurs overnight may trigger the automatic closing of a water valve for a distributed water infrastructure, but in order for water to be available the next morning, the valve may be automatically opened.

In some embodiments, the measurement of water usage may be performed by any one of the systems described herein, and/or the measure of water usage may be performed by a third-party water measuring device. The measurement of water usage may be performed by separate devices distributed by distance, wherein the processing operations may be performed locally or at a central location. The processing operations may be performed in real time, and/or at a later time, e.g., through a batch process or delayed process. The processing operations may also be provided by distributed parallel or cloud computing infrastructures with data and results transported to the cloud or parallel processor using wireless or wired networks.

In accordance with the present disclosure, some of the embodiments described herein provide examples of the novel benefits provided by event-based leak detection systems and methods. In some embodiments, a measurement of the number of liters consumed as a function of time may be transformed into a water usage pattern that has a particular fingerprint or water usage pattern. A water usage pattern may be determined by any method consistent with identification herein, such as the non-limiting examples of: event-based threshold method, guided machine learning, or automatic machine learning. Water usage pattern determination may be assisted by a neural network, whereby a system may progressively improve performance to determine, identify, and compare water usage patterns by considering examples. In some embodiments, a neural network may be used without task-specific programming.

In various alternative methods, remote valve reopening and/or automatic valve closure after the detection of abnormal consumption may be implemented by alternative methods of receiving water information, and employing event-based leak detection systems and methods to provide granularity of water usage to an end user.

Exemplary Embodiments of Preventing Frozen Pipe Breaks

The present application provides for systems for preventing frozen pipe breaks. One potential benefit of systems that include a sensor capable of detecting when a pipe is about to freeze, and then release a valve, is to prevent damage caused by frozen pipes and resulting leaks. A system consistent with the present disclosure may be configured to automatically open a release valve to initiate mitigating flow through an at-risk pipe. A transmitter may remotely send a notification to an administrator with the ability to initiate this or other remedial actions.

An aspect of some embodiments may include a system for mitigating frozen pipe bursts. The system may comprise at least one processor. The at least one processor may be configured to receive from a sensor associated with a pipe in a distributed water infrastructure at least one signal indicative of the pipe being in a near-freezing pipe condition. The at least one processor may be configured to analyze the at least one signal to determine whether remedial action may be warranted. The at least one processor may be configured to generate a control signal for causing a remedial action associated with the near-freezing pipe. The at least one processor may be configured to cause the control signal to be transmitted to thereby commence the remedial action in order to reduce a possibility of a bursting of the near-freezing pipe.

In some embodiments, the control signal may include a command to open a valve associated with the freezing pipe. The valve may be a trickle valve. The system may be configured to transmit leak warnings and the system may be further configured to avoid sending leak warnings associated with flow through the trickle valve. The remedial action may include sending, via a remote communication transmitter, a notification to an administrator and opening a trickle valve.

In some embodiments, the at least one processor may be configured to receive from the administrator a trickle valve open command, wherein the processor may be further configured to transmit the control signal to the trickle valve in response to the trickle valve open command. The at least one sensor may include a temperature sensor. The at least one processor may be configured to receive a plurality of signals from a plurality of sensors across the distributed water system. Each of the plurality of sensors may have an address associated with a location in the distributed water system. The at least one processor may be configured to open at least one of a plurality of trickle valves in a location proximate to a sensor from which a near-freezing condition signal emanates.

In some embodiments, the at least one processor may be configured to maintain a unique identifier address for each of the plurality of sensors and the plurality of trickle valves, and to associate at least one sensor unique identifier address with at least one trickle valve identifier address. When a remedial instruction is received, the at least one processor may enable opening of a trickle valve associated with a corresponding sensor that prompted the remedial instruction.

Exemplary Embodiments of Abnormal Consumption Detection During Normal Water Usage The present application provides for leak detection during normal water usage. A potential benefit of some embodiments may include the ability to detect abnormal consumption, even during times of normal water usage. In some embodiments, this may be done by determining a baseline of existing usage, and ascertaining a non-expected deviation from the baseline. In addition or in the alternative, systems and methods may be able to identify the use of water at a granular level, such that normal water usage may be categorized into discrete events, and the addition of a new unrecognized event may indicate a leak.

An aspect of some embodiments may include a system for detecting abnormal consumption in a distributed water infrastructure while water usage occurs in the infrastructure. The system may comprise at least one processor. In some embodiments, the at least one processor may be configured to receive from at least one sensor associated with the distributed water infrastructure indications of regular water usage. An indication of regular water usage may be a signal indicating water consumption originating from at least one correctly functioning water-consuming appliance that may be connected to a distributed water infrastructure, which may be faultless.

A water-consuming appliance may be any appliance that consumes water whether mechanical such as a faucet or a toilet, or electro-mechanical such as a washing machine or dish-washer for which the term "correctly functioning" implies that it is not damaged or malfunctioning in any way that may impede or interfere with its normal water-consuming function. A faultless distributed water infrastructure may be one that is not subject to any blockages or leaks and for which all the water consumers connected to it are working correctly.

Indications of regular water usage may be signals received from a sensor associated with the distributed water infrastructure that are each represented by some quantitative value equivalent to the time when the signal was received, whether as a time stamp or a as relative time difference, since the previous signal or as cumulative measure of time from a reference in time.

In some embodiments, the at least one processor may be configured to determine from a plurality of indications received over a time period, a plurality of baseline water usage profiles. A baseline water usage profile may be a normal water event profile that characterizes specific water usage that may occur regularly or predictably in a distributed water system and therefore represents a typical usage of water in that water system. Within a plurality of baseline profiles, each profile may correspond to a particular water consumer connected to the distributed water infrastructure or a typical use of a particular water consumer. A profile may have several levels of specificity. For instance, one baseline water usage profile may be associated with washing of hands in a faucet. Another level of baseline water usage profiles may be associated with a particular user, who usually cooks and washes their hands multiple times during cooking or uses a dishwasher after the meal. These baseline water event profiles may be learned during a learning period. These baseline profiles may also be informed by previously established water event profiles. A baseline water profile may be saved in the memory of at least one processor associated with the distributed water system and, either individually or together with other baseline water usage profiles, may provide a reference that characterizes the normal water consumption in the distributed water system.

In some embodiments, the at least one processor may be configured to receive from the at least one sensor a current water usage profile. A current water usage profile may be an indication of the current water consumption. A current water usage profile may be a signal indicating water consumption originating from at least one correctly functioning water-consuming appliance that may be connected to a distributed water infrastructure. In some embodiments, a distributed water infrastructure may be faultless. A faultless distributed water infrastructure may be one that is not subject to any blockages or leaks, such that all the water consumers and/or appliances connected to it are working as intended. A water consumer may be any appliance that consumes water whether mechanical such as a faucet or a toilet, or electro-mechanical such as a washing machine or dish-washer. The term "correctly functioning" implies that such a water consumer or appliance is not damaged in a way that may impede or interfere with its water-consuming function.

Indications of regular water usage are gathered by signals received from a sensor associated with the distributed water infrastructure. Indications of water usage may be characterized by a quantitative value equivalent to the time when the signal was received. The quantitative value may be a time stamp, a relative time difference since the previous signal, or a cumulative measure of time from a reference in time.

In some embodiments, the at least one processor may be configured to compare the current water usage profile with the plurality of baseline water usage profiles. Where there are no faults in the water system, the current water usage profile may find agreement between the current water usage profile and at least some of the profiles in a plurality of stored baseline water usage profiles.

In some embodiments, the at least one processor may be configured to determine a likely abnormal water consumption based on the comparison between the current water usage profile and the plurality of baseline water usage profiles. An abnormal water consumption signal may be a current event profile that is not similar enough or too different to the baseline water event profiles that have been constructed for a distributed water infrastructure and may be therefore considered abnormal for that water infrastructure. The acceptable limits of similarity or difference between a baseline profile and a current event profile may be defined by a quantitative range that deviates from each baseline profile. The quantitative range may be flexible for each water consumption profile. In some embodiments, if a water consumption profile consumes a large amount of water, then the quantitative range may be relatively large compared to a smaller water consumption event. If the water consumption profile includes many varying levels of water consumption, but shares other characteristics for a water consumer, then the quantitative range may be directed to characteristics other than the amount of water consumed. In some embodiments, the at least one processor may be configured to generate an abnormal water consumption signal when likely abnormal water consumption is determined.

An aspect of the disclosure may be directed to a system for detecting abnormal consumption in a distributed water infrastructure while water usage occurs in the infrastructure. The system may comprise at least one processor configured to receive from at least one sensor associated with the distributed water infrastructure indications of regular water usage, determine from a plurality of indications received over a time period a plurality of baseline water usage profiles, receive from the at least one sensor a current water usage profile, compare the current water usage profile with the plurality of baseline water usage profiles, determine a likely abnormal water consumption based on the comparison between the current water usage profile and the plurality of baseline water usage profiles, and generate an abnormal water consumption signal when likely abnormal water consumption is determined.

In some embodiments, the determined plurality of baseline water usage profiles may include a plurality of profiles unique to appliances within the distributed water infrastructure. At least one processor may be configured to receive from an end user an indication of a specific appliance in use, and to store in an associated manner, the specific appliance with a baseline water usage profile associated with the specific appliance. At least one processor may be configured to determine specific appliances without input from an end user. Some appliances may be identifiable without input from an end user, due to identifiable characteristics of the water consumption. By way of non-limiting examples, the identifiable water characteristics may be an initial flow rate, a sustained flow rate, and a total volume of water consumed. For example, the use of a shower may be determined by a flow rate of 8 liters per minute, and a flow rate that lasts for 8 minutes.

In some embodiments, the distributed water infrastructure may include a plurality of water-consuming appliances, wherein each of a plurality of baseline water usage profiles may be associated with a differing specific appliance within the distributed water infrastructure. Following an addition of a new water appliance to the distributed water infrastructure, the at least one processor may be configured to adjust at least some of the baseline water usage profiles associated with other appliances in the distributed water infrastructure. In such an instance, the system will not initiate an unnecessary leak alert after the addition of an appliance.

Profiles unique to appliances are signals or groups of signals indicative of water consumption over time that have been identified as originating from an appliance connected to the distributed water infrastructure. In some embodiments, there may be only a single appliance with the unique water consumption profile. In another embodiment, there may be several appliances, e.g. faucets, that share a distinctive water consumption profile. An appliance may be either a mechanical appliance such as a toilet or a tap in a sink or in a shower, or an electro-mechanical device such as a dish-washer, washing machine, water-filtration system, or automatic irrigation system. Such profiles may uniquely identify water consumption by a particular appliance.

In some embodiments, a quantitative comparison may occur between the current water usage profile and at least one baseline profile. The current water usage profile may be the group of signals received by at least one processor from at least one sensor associated with a distributed water infrastructure, which are produced by at least one consumer or appliance in the distributed water infrastructure. In some embodiments, when no water consumption is occurring the water consumption profile may be zero. The current water consumption profile may include a signal or group of signals that at least one appliance is currently consuming water.

A quantitative comparison of the current water event profile with a baseline water event profile may be achieved by applying a suitable mathematical operation on the data of the two profiles, which calculates a measure either of similarity or dissimilarity between them and expresses this measure with a quantitative value. In some embodiments, quantitative comparison involves subtraction of one compared profile versus another compared profile, and the magnitude of the remainder may be used to determine a match. Part of a profile may be compared with another profile. As a non-limiting example, two handwashing water usage patterns that last a different amount of time may be matched by comparing the beginning of the water usage patterns.

A quantitative comparison of the current water event profile with a baseline water event profile may be achieved by applying a form of subtraction of the data or the pre-processed data of one of the profiles from the other, which produces a measure of dissimilarity between the two profiles expressed by a single quantity representing this deviation. In some embodiments, quantitative comparison involves subtracting a known water consumption rate from the current water consumption rate, and concluding that the current water consumption profile matches a known baseline water consumption profile, if the remainder after subtraction is substantially zero.

In some embodiments, the abnormal water consumption signal contains an indication of an appliance likely to be leaking. The abnormal water consumption signal may be accompanied by a device that is likely causing the leak.

In some embodiments, an indication that an appliance may be leaking during an abnormal consumption event may be determined by matching the current water consumption profile to a unique appliance, but where the measure of comparison of the abnormal consumption profile exceeds a maximal value for at least one of the profiles of unique appliances. This quantitative measure of comparison may constitute a combination of similarity and dissimilarity measures applied to all or parts of the profiles being compared. In some embodiments, a likely device to be causing the abnormal water consumption may be identified by the time that the leak occurs. For example, if showers are usually taken at a certain time in the morning, and a leak occurs at that time, then an indication may be provided that suggests that the leak may be associated with the shower.

In some embodiments, an abnormal water consumption signal may be configured to trigger a remedial action for abating the abnormal consumption, wherein the remedial action may include at least one of sending an alert and automatically closing a valve. At least one processor may be configured to detect changes in at least two baseline water usage profiles within a predetermined period and generate a signal indicating a blockage in the distributed water infrastructure. The at least one processor may be configured to detect a change in at least one characteristic of at least one baseline water usage profile. The at least one characteristic may be selected from an initial rise in flow rate, an average sustained flow rate, a total amount of water consumed, a duration of the baseline water usage profile, and cycles of water usage.

In some embodiments, at least one processor may be configured to compare the current water usage profile against known abnormal water event profiles. The at least one processor may be configured to receive, from an end user, information on abnormal water event profiles. Comparing may include a subtraction of the current water usage profile and at least one baseline water usage profile to determine if a remainder matches a predetermined threshold for a leak.

In some embodiments, at least one processor may be configured to determine a specific appliance associated with the abnormal water consumption by identifying a recently-used appliance. The at least one processor may be configured to determine a specific appliance associated with the abnormal water consumption by determining whether a current water usage profile differs from a baseline water usage profile by more than a threshold difference in similarity.

In some embodiments, at least one processor may be further configured to compare the current water usage profile and a baseline water usage profile by deconstructing each profiles into subcomponents and comparing subcomponents. The at least one processor may be configured to determine a malfunction in a specific water appliance in the distributed water infrastructure by accessing memory storing a reference water usage profile of the specific water appliance, comparing a current water usage profile associated with the specific appliance with the reference water usage profile, and determining an appliance malfunction based on at least one difference identified in the comparing.

In some embodiments, at least one sensor may be a flow sensor with an unmeasured flow reducer. At least one sensor may be configured to detect flow at a rate of less than about 2 liters per hour.

Figure 6:
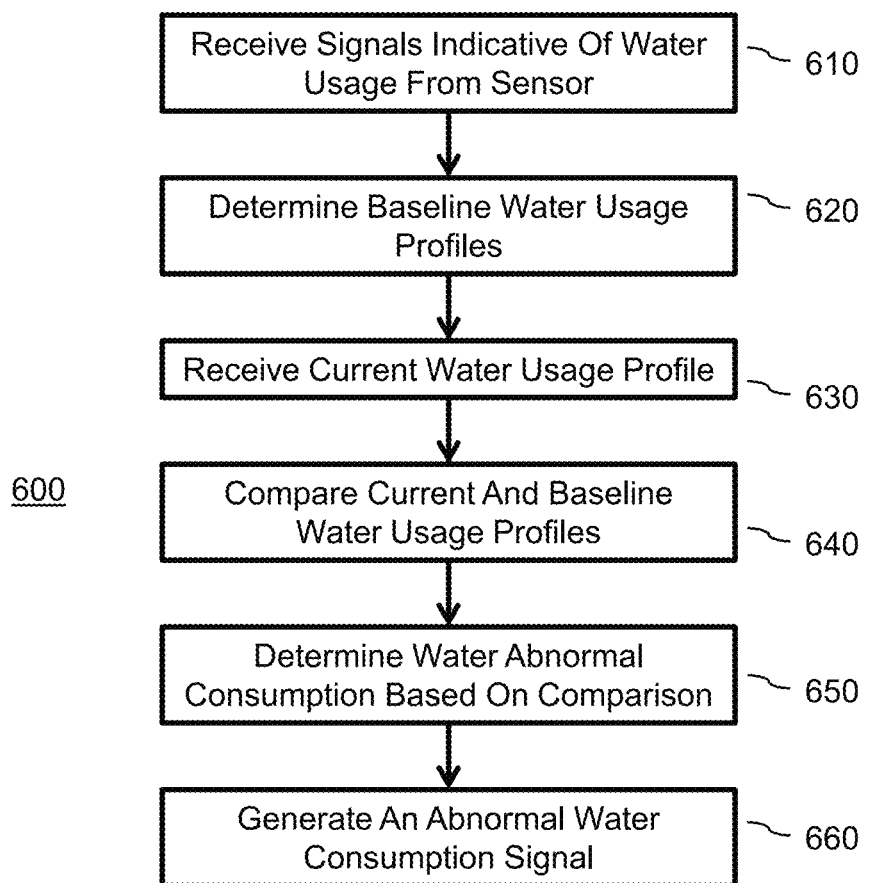
FIG. 6 illustrates an exemplary method for detecting abnormal consumption in a portion of a distributed water infrastructure.

FIG. 6 illustrates an exemplary method 600 for detecting abnormal consumption in one portion of a distributed water infrastructure while normal water usage occurs in another portion of the distributed water infrastructure. The operations of method 600 discussed herein are intended to be merely illustrative. In some embodiments, method 600 may be implemented with one or more additional operations not described, and/or without one or more of the operations discussed. Additionally, the order in which the operations of method 600 are illustrated in FIG. 6 and described herein is not intended to be limiting.

In some embodiments, method 600 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 600 in response to instructions stored electronically on an electronic storage medium. The one or more processing devices may include one or more devices configured through hardware, firmware, and/or software to be specifically designed for execution of one or more of the operations of method 600.

In some embodiments, at operation 610, at least one processor may be configured to receive from at least one sensor associated with the distributed water infrastructure indications of regular water usage. While this operation may serve the purpose of gathering information for baseline water usage, a large facility or an analogous water distribution infrastructure may share sufficient characteristics that a baseline water usage could be shared between at least two devices. In some embodiments, this step may not be necessary and the system may not include configuring to receive from at least one sensor associated with the distributed water infrastructure indications of regular water usage. At operation 620, at least one processor may be configured to determine from a plurality of indications received over a time period, a plurality of baseline water usage profiles. At operation 630, at least one processor may be configured to receive from the at least one sensor a current water usage profile.

At operation 640, at least one processor may be configured to compare the current water usage profile with the plurality of baseline water usage profiles. At operation 650, at least one processor may be configured to determine an abnormal water consumption based on the comparison between the current water usage profile and the plurality of baseline water usage profiles. At operation 660, at least one processor may be configured to generate an abnormal water consumption signal when abnormal water consumption is determined.

In some embodiments, the measurement of water usage may be performed by any one of the systems described herein, and/or the measure of water usage may be performed by a third-party water measuring device. The measurement of water usage may be performed by separate devices distributed by distance, wherein the processing operations may be performed locally or at a central location. The processing operations may be performed in real time, and/or at a later time. The processing operations may also be provided by distributed parallel or cloud computing infrastructures with data and results transported to the cloud or parallel processor using wireless or wired networks.

In accordance with the present disclosure, some of the embodiments described herein provide examples of the novel benefits provided by event-based leak detection systems and methods. In some embodiments, a measurement of the number of liters consumed as a function of time may be transformed into a water usage pattern that has a particular fingerprint or water usage pattern. A water usage pattern may be determined by any method consistent with identification herein, such as the non-limiting examples of: event-based threshold method, guided machine learning, or automatic machine learning. Water usage pattern determination may be assisted by a neural network, whereby a system may progressively improve performance to determine, identify, and compare water usage patterns by considering examples. In some embodiments, a neural network may be used without task-specific programming.

In various alternative methods, detecting abnormal consumption in one portion of a distributed water infrastructure while normal water usage occurs in another portion of the distributed water infrastructure may be implemented by alternative methods of receiving water information, and employing event-based leak detection systems and methods to provide granularity of water usage to an end user.

Exemplary Embodiments of Low Flow Abnormal Consumption Detection During Periods of No Water Usage The present application may provide for slow leak detection during periods of no water usage. A potential benefit of systems and methods of the present disclosure may include allowing the examination of liquid flow during periods when no water use is expected, such as on weekends or at night. During such times, water usage, particularly low flow or low volume usage, may be likely attributable to a leak. The ability to discern flow during specific times, as opposed to general thresholds over the course of a month, are valuable to determine low level leaks.

An aspect of some embodiments may include a system for detecting abnormal consumption in a distributed water infrastructure. In some embodiments, the distributed water infrastructure may include a plurality of water appliances. The system may include at least one processor configured to receive from at least one sensor associated with the distributed water infrastructure indications of regular water usage. At least one processor may be configured to determine, from the indications received over a time period, at least one recurring time period of expected diminished water usage.

At least one processor may be configured to determine, for the at least one recurring time period of expected diminished water usage, at least one expected diminished water usage profile. In some embodiments, the at least one processor may be configured to determine, from a plurality of indications received over a time period, at least one expected water usage profile. A time period may refer to a sufficient period of time for the system to gather enough indications of water consumption in order for it to determine typical water usage profiles for that water infrastructure. An expected water usage profile may refer to a plurality of signals indicative of water usage in a distributed water infrastructure that originate from the usage of a particular water consumer, such as a water appliance, which may be connected to that water infrastructure. The system may operate for an extended period of time to gather representative data from the different consumers that are connected to the distributed water infrastructure. Additionally or alternatively, the system may operate for a relatively short amount of time if the full range of different consumers occurs over a short period of time.

In some embodiments, at least one processor may be configured to receive from the at least one sensor, during a current time period of expected diminished water usage, a real-time indications of water usage that constitutes a current water usage profile. At least one processor may be configured to compare the current water usage profile during the expected period of diminished water usage with the at least one expected diminished water usage profile. At least one processor may be configured to determine, based on the comparison, that water usage in the current water usage profile materially exceeds water usage in the at least one expected water usage profile.

In some embodiments, at least one processor may be configured to execute a remedial action when, based on the comparison, the current water usage profile materially exceeds the at least one expected water usage profile. At least one processor may be configured to receive from the at least one sensor, during a period when at least one appliance within the water infrastructure may be in non-use, a current water usage profile. The at least one processor may be configured to compare the current water usage profile with the at least one expected water usage profile. The at least one processor may be configured to determine, based on the comparison, whether the current water usage profile does not substantially correspond to the at least one known water usage profile.

In some embodiments, the at least one processor may be configured to generate an abnormal consumption indication signal when, based on the comparison, the current water usage profile does not substantially correspond to the at least one known water usage profile. A current water event profile that is sensed in some distributed water infrastructure may be compared to a normal event profile using a mathematical operation that outputs a quantitative measure of similarity or dissimilarity between the two profiles. A current event profile may be said to not substantially correspond to the normal event profile if the measure of similarity or dissimilarity lies beyond the acceptable limits of correspondence that may be defined for the normal event profile. The acceptable limits of correspondence may be expressed by a standard deviation or variance or any other quantitative measure of spread defined over the numerical representation of the normal water event profile.

In some embodiments, at least one sensor of the system has a resolution of at least 0.2 liters per hour. In a preferred embodiment, the at least one sensor of the system has a resolution of greater than 0.2 liters per hour. Sensors with a resolution of less than 0.2 liters per hour may still detect abnormal water consumption, but with less accuracy. In one embodiment, at least one sensor of the system has a resolution of one of: at least 0.1 liters per hour, at least 0.05 liters per hour, and at least 0.01 liters per hour.

In some embodiments, at least one expected water usage profile may include a plurality of profiles each associated with a differing period of expected diminished water usage, wherein during comparing, the current water usage profile may be compared with an expected diminished water usage profile corresponding to a time period of the current water usage profile.

In some embodiments, at least one of the expected diminished water usage profiles may correspond to a night time period when substantially no normal water usage is expected in the distributed water infrastructure. At least one expected diminished water usage, during night time, may take into account automated consumption of water from appliances and periodically occurring irregular uses.

In some embodiments, at least one processor may be configured during comparing, to compare the current water usage profile with at least one preset water usage profile that corresponds to a leak. The at least one preset water usage profile may correspond to a leak of at least 0.2 liters per hour.

In some embodiments, a remedial action may include generating an abnormal consumption alert. At least one processor may be configured, during comparing, to compare the current water usage profile with at least one preset water usage profile that corresponds to a water appliance, wherein the remedial action may include generating an abnormal consumption alert indicating a use of the water appliance.

An aspect of some embodiments may include a system for detecting abnormal consumption in a distributed water infrastructure. The system may include at least one processor. At least one processor may be configured to receive, from a water sensor upstream of a plurality of water appliances in the distributed water infrastructure, overall water consumption measurements. At least one sensor may have a resolution of less than two liters per hour. The at least one processor may be configured to determine periods when the distributed water infrastructure may be in an inactive state of substantial non-use of water appliances. The at least one processor may be configured to track water consumption during a plurality of times when the distributed liquid infrastructure is in an inactive state.

In some embodiments, at least one processor may be configured to detect an upward trend in water consumption over the plurality of times. The at least one processor may be configured to initiate remedial action when an upward trend is detected. Remedial action may include generating an abnormal consumption alert.

In some embodiments, at least one processor may be configured to automatically determine periods when the distributed water infrastructure is in an inactive state and water appliances are in substantial non-use. At least one processor may be configured to determine periods when the distributed water infrastructure is in an inactive state by accessing a timetable stored in memory, wherein the timetable may include times of inactivity supplied by an administrator. The periods when the distributed water infrastructure is in an inactive state or substantial non-use may include a non-zero continuous baseline of water usage. The at least one processor may be configured to construct an expected water event profile for consumption of water during the inactive state. The at least one processor may be configured to compare a current overall water consumption measurements with an expected water event profile for the consumption of water during the inactive state. The at least one processor may be configured to store indications of a plurality of expected periods of substantial water inactivity and to initiate remedial action when a decrease is detected in an overall number of actual periods of substantial water inactivity.

Figure 7:
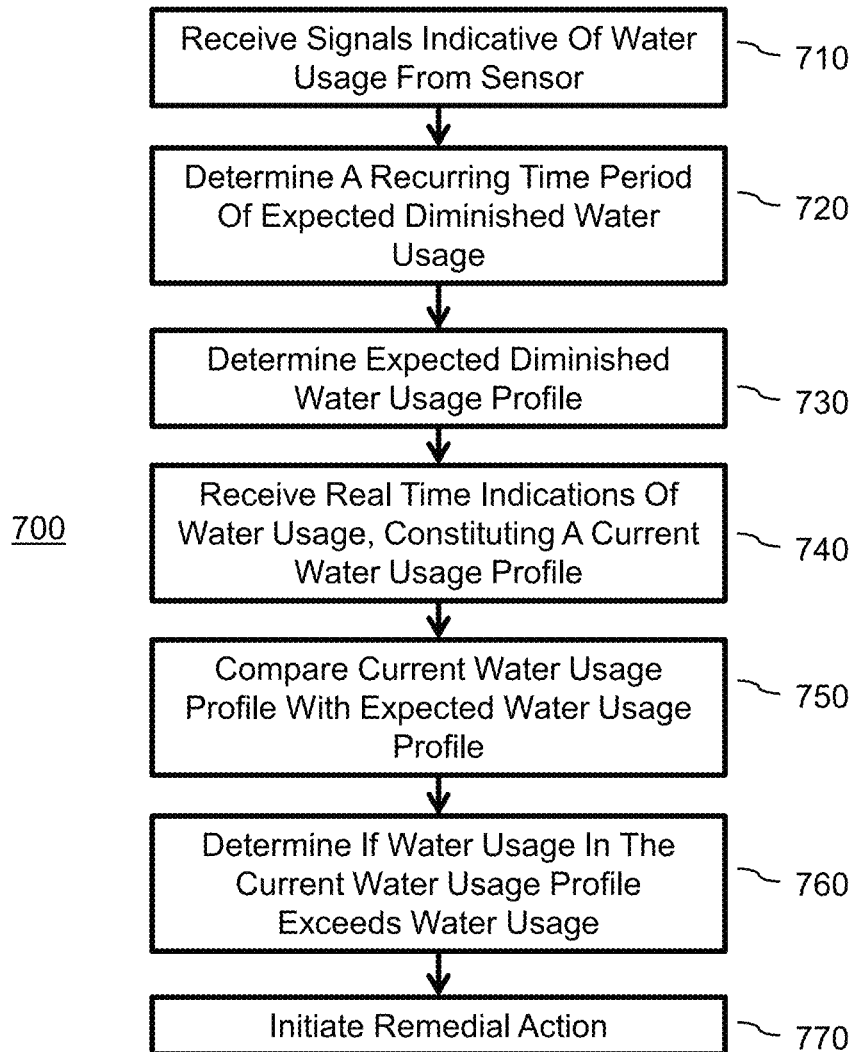
FIG. 7 illustrates an exemplary method for detection of abnormal consumption with low volumes of water consumption.

FIG. 7 illustrates an exemplary method 700 for detection of abnormal consumption with low volumes of water consumption. The operations of method 700 discussed herein are intended to be illustrative. In some embodiments, method 700 may be implemented with one or more additional operations not described, and/or without one or more of the operations discussed. Additionally, the order in which the operations of method 700 are illustrated in FIG. 7 and described herein is not intended to be limiting.

In some embodiments, method 700 may be implemented in one or more processing devices. The one or more processing devices may include one or more devices executing some or all of the operations of method 700 in response to instructions stored electronically on an electronic storage medium. The one or more processing devices may include one or more devices configured through hardware, firmware, and/or software to be specifically designed for execution of one or more of the operations of method 700.

In some embodiments, at operation 710, at least one processor may be configured to receive from at least one sensor associated with the distributed water infrastructure, indications of regular water usage, wherein the distributed water infrastructure may include a plurality of water appliances. At operation 720, at least one processor may be configured to determine, from the indications received over a time period, at least one recurring time period of expected diminished water usage. At operation 730, at least one processor may be configured to determine, for the at least one recurring time period of expected diminished water usage, at least one expected diminished water usage profile. At operation 740, at least one processor may be configured to receive, from the at least one sensor during a current time period of expected diminished water usage, real time indications of water usage that constitutes a current water usage profile.

At operation 750, at least one processor may be configured to compare the current water usage profile during the expected period of diminished water usage with the at least one expected diminished water usage profile. At operation 760, at least one processor may be configured to, based on the comparison, determine that water usage in the current water usage profile materially exceeds water usage in the at least one expected water usage profile. At operation 770, at least one processor may be configured to execute a remedial action when, based on the comparison, the current water usage profile materially exceeds the at least one expected water usage profile.

In some embodiments, the measurement of water usage may be performed by any one of the systems described herein, and/or the measure of water usage may be performed by a third-party water measuring device. The measurement of water usage may be performed by separate devices distributed by distance, wherein the processing operations may be performed locally or at a central location. The processing operations may be performed in real time, and/or at a later time. The processing operations may also be provided by distributed parallel or cloud computing infrastructures with data and results transported to the cloud or parallel processor using wireless or wired networks.

In accordance with the present disclosure, some of the embodiments described herein provide examples of the novel benefits provided by event-based leak detection systems and methods. In some embodiments, a measurement of the number of liters consumed as a function of time may be transformed into a water usage pattern that has a particular fingerprint or water usage pattern. A water usage pattern may be determined by any method consistent with identification herein, such as the non-limiting examples of: event-based threshold method, guided machine learning, or automatic machine learning. Water usage pattern determination may be assisted by a neural network, whereby a system may progressively improve performance to determine, identify, and compare water usage patterns by considering examples. In some embodiments, a neural network may be used without task-specific programming.

In various alternative methods, detection of abnormal consumption with low volumes of water consumption may be implemented by alternative methods of receiving water information, and employing event-based leak detection systems and methods to provide granularity of water usage to an end user.

Exemplary Embodiments of Abnormal Consumption Detection with Remainder after Subtracting known Events The present application may provide for leak detection by identifying a remainder after subtracting known events. In a distributed water infrastructure such as an office building, many water events regularly occur simultaneously, increasing the challenge in detecting an anomaly. A potential benefit of systems and methods of the present disclosure may include subtracting all detected known events from an overall infrastructure profile and examining the remainder to determine if the remainder is likely attributable to a leak.

An aspect of some embodiments may include a system for detecting abnormal consumption in a distributed water infrastructure. The system may comprise at least one processor. In some embodiments, the at least one processor may be configured to receive from at least one sensor associated with the distributed water infrastructure indications of a current overall water usage profile in the distributed water infrastructure. The at least one processor may be configured to access a database of individual water usage profiles associated with water appliances in the distributed water infrastructure. The at least one processor may be configured to determine at least one individual water usage profile that makes up the current overall water usage profile. The at least one processor may be configured to segment the at least one individual usage profile from the current overall usage profile.

In some embodiments, the at least one processor may be configured to analyze data associated with the segmenting to determine whether abnormal consumption may be occurring in the distributed water infrastructure. The at least one processor may be configured to generate an abnormal consumption signal when likely abnormal consumption is determined.

In some embodiments, segmenting may include subtracting the at least one individual liquid usage profile from the overall liquid usage profile to obtain a remainder. Analyzing may include determining whether the remainder may be indicative of abnormal consumption. The database of individual water usage profiles may be generated from the history of at least one sensor associated with the distributed water infrastructure. The individual water usage profiles in the database may be confirmed by an end user. An individual water usage profile may include a group of water usage profiles Exemplary Embodiments of Ignoring Abnormal Consumption The present application may provide for a feature for an end user to ignore certain leak notifications. Not all leak notifications are necessarily important leaks, or may be misidentified as a leak. These notifications may annoy or distract an end user. A potential benefit of systems and methods of the present disclosure may include permitting administrators, after receiving notification of a potential leak, to have the ability to remotely instruct the system to ignore a leak.

An aspect of some embodiments may include a remote communication override abnormal consumption detection system for a distributed water infrastructure. The system may comprise at least one processor. The at least one processor may be configured to receive water usage information from at least one sensor regarding a distributed water infrastructure. The at least one sensor may be associated with the distributed water infrastructure. For example, the sensor may be associated with a pipe in the distributed water infrastructure. The sensor may be partially, or completely, within the pipe or outside the pipe.

In some embodiments, the at least one processor may be configured to determine from the water usage information an event likely to be an abnormal consumption within the distributed water infrastructure. The at least one processor may be configured to send via a transmitter a message to an administrator notifying the administrator of the likely abnormal consumption, and providing to the administrator data associated with the likely abnormal consumption.

A message refers generally to any information sent by the system. The system may send a message in the form of two-way data packages. Two-way data packages may be transmitted and received, either continually, or intermittently, between the system and the administrator. Exemplary message contents may include, but are not limited to, information regarding water consumption data, water quality, appliance usage, and health profile.

Data associated with the likely abnormal consumption may include, but are not limited to, a current water consumption profile that may be sensed in a distributed water system. Data associated with likely abnormal consumption may include information that the current conditions within the distributed water infrastructure meet the conditions of a stored abnormal water event. In some embodiments, data associated with the likely abnormal consumption may include a current water consumption profile, pre-learned water consumption profiles that characterize normal consumption, and any definitions of acceptable distance limits between a pre-learned consumption profile and a current water consumption profile.

In certain instances, a customer or an administrator may find an abnormal water event to be acceptable. In such circumstances, a customer may not want to be bothered by continual reminders or alerts for the abnormal water event. The at least one processor may be configured to receive from the administrator via the receiver a command to ignore the likely abnormal consumption indication. The at least one processor of the system may be configured to receive, in response to the transmitted message, a command to close a valve.

A command to ignore may be generated by the administrator or by the customer to signal the system that an abnormal alert has been received and the administrator, or customer, prefers to ignore the abnormal water consumption event. A remote communication override abnormal consumption detection system may permit water to flow through the valve after the ignore command is received.

In some embodiments, the processor may be configured to store a profile of the likely abnormal consumption associated with the ignore abnormal consumption command received from the administrator, and to avoid sending a subsequent likely abnormal consumption message to the administrator the next time a likely abnormal consumption matches the stored profile.

In some embodiments, the system may store a water profile in a nonvolatile memory (NVM) device. A stored profile may include any of a water consumption profile, a time stamp, a water flow rate, and any water quality information, as well as appliance usage and health profile.

In some embodiments, the system may be configured to avoid customer harassment and have a low false alarm rate. The system may have logic to reduce the number of alerts and use an effective messaging system with fewer alerts.

In some embodiments, the data provided to the administrator may include at least one of flow rate and flow volume of the likely abnormal consumption. The data provided to the administrator may include location information for the likely abnormal consumption. Gathering the location information for the likely abnormal consumption may be a function implemented in the cloud in order to get an overall geographical view about any abnormal consumption distribution. The system may provide information that may be used to initiate a water service for customers. A water service provider or residence may use information gathered by multiple sensors to identify that some appliances that are within a geographic location are malfunctioning.

In some embodiments, the data provided to the administrator may include an indication of an identity of a malfunctioning appliance. An indication of an identity of a malfunctioning appliance may be based on a deviation beyond a certain threshold level from a normal pattern of the appliances. A normal pattern may include all the information that defines and indicates the normal functioning of the appliance. Exemplary information may include information related to flow, usage, time, water patterns, vibration, and any health profile of the water-consuming device.

In some embodiments, at least one processor may be configured to provide updated data to the administrator following an initial alert in order to enable the administrator to assess ongoing severity. Abnormal water consumption may only last for a period of time before stopping. For example, a leak in an irrigation system may only occur when the irrigation system is in use. The processor may be configured to provide updated data to the administrator following an initial alert in order to enable the administrator to determine if the likely abnormal consumption has self-mitigated. An abnormal water consumption event that has self-mitigated may refer to a situation where the system, either automatically or under the direction of an administrator, has taken an action that mitigates and reduces the severity of the event. Once the risk to property or appliance or degradation in appliance performance has been mitigated or corrected, the system may inform the administrator that the adverse event is resolved.

In some embodiments, the processor may be further configured to close a system-wide valve in response to a command to close the valve. A system-wide valve refers generally to at least one valve that may control the distribution of water through the system. In other embodiments, the system-wide water consumption may be controlled through mechanisms other than a valve. For example, water consumption may be halted by diverting water to an emergency reservoir.

In one embodiment, a system may support several water consumption configurations. A distributed water infrastructure may comprise a main water pipe system with a large diameter at an entrance to a large building, and small diameter water pipe systems for each floor. In some embodiments, a system-wide valve may control the water flow through a house or single building. A system-wide valve may control water flow through a floor of a building or to a particular room.

In some embodiments, the at least one processor may be further configured to close a sub-system valve in response to a command to close the valve. The at least one processor may be configured to close a system-wide valve if neither a close valve or an ignore command is received within a predetermined time period following message transmission to the administrator. In some embodiments, a predetermined time period may be at least 30 seconds, at least 1 minute, at least 5 minutes, at least 10 minutes, at least 15 minutes, at least 30 minutes, and at least 45 minutes. In some embodiments, the predetermined time period may be one of: at least 1 hour, at least 2 hours, at least 3 hours, at least 5 hours, at least 10 hours, and at least 24 hours. The predetermined time period may depend on the type of abnormal water event detected. A predetermined time period may be relatively short if the abnormal water event is determined to consume a large amount of water. A predetermined time period may be relatively long if the abnormal water event is determined to consume a small amount of water. A predetermined time period may be set by a consumer. The system may have a built-in mechanism to control the period of time before a reminder is transmitted to a consumer, or to control length of the predetermined time period to close a system-wide valve.

An advantage of some embodiments may be the ability of a system to communicate to a remote user. A remote user may be informed of an emergency even if in a remote location, and address the emergency from the remote location. The transmitter may be a remote communication transmitter and the receiver may be a remote communication receiver.

Exemplary Embodiments of Self-Monitoring Water Appliances

The present application may provide for a system that monitors the performance of water appliances. Some water-using appliances may deteriorate in performance after a certain amount of time. An aspect of the disclosure may be directed to water appliances such as washing machines and dishwashers that are able to check their own health by monitoring deviations from normal water usage profiles. It is envisioned that this process may be performed at the level of a distributed water infrastructure, or at the level of an individual appliance.

Some water-using appliances may deteriorate in performance after a certain amount of time. This deterioration may be in the form of an increase in the amount of water consumed during the operation of the appliance. For example, some part of the water appliance may be leaking. The water appliance may be required to consume more water before the appliance ceases operation. The deterioration of a water appliance may be apparent from a decrease in the amount of water consumed during the operation of the application. For example, the water appliance may be clogged such that water does not flow properly into the appliance. The water appliance may not need to demonstrate either an increase or decrease in water consumption, but the flow of water into the appliance may show a difference from a normally operating appliance. For example, an appliance may be clogged, or have a loose valve such that the amount of water flow oscillates over time, even though the total amount of water consumed by the device does not differ from that of a normally operating device.

An aspect of some embodiments may include a water-using appliance. The water-using appliance may comprise an inlet for connection to a water source, and a water outlet. A water-using appliance may be any device that takes water as an input and discards water as an output. The appliance might enhance the water inputted via an enhancement process (e.g. filter, or ultraviolet purification system). The appliance output (water outlet) may be an input for other appliances, faucets, or taps. Examples of water-using appliances range from faucets, mini-bars, washing machine, dishwasher, or industrial machinery. A water source refers generally to the input for a water-using appliance. The water source may be any inlet that provides water for a water-using appliance. The water source may be a major water main that provides water to a water-using appliance. The water source may be a source of water inside a building proximate to the water-using appliance. A water outlet refers to an outlet that water exits after water has passed through the device. Water-using appliances may have specific piping where water goes after the water-using appliance has finished its use of the water. The water outlet may be a drain, sewer, or another water-using appliance. In some embodiments, a water-using appliance may be any appliance that includes a chamber between a water inlet and a water outlet, where the chamber may be configured to enable water to be employed as part of a process. For example, a water using appliance comprising a chamber may include a washing machine, a wet carpet cleaner, and an ice machine.

In one embodiment of the water appliance, at least one sensor may be integrated into the appliance for monitoring water usage of the appliance. Memory may be integrated into the appliance for storing water usage information indicative of normal operation of the appliance. A water-using appliance may have the ability to retain useful water usage information that can help the appliance be monitored (either independently or from a central source) for proper usage.

In some embodiments, at least one processor may be integrated with the appliance. An integrated processor refers to a processor that is included with the appliance. The processor may be within the water-using appliance. In other embodiments, the processor may be enclosed within a separate container that may be part of the appliance. The water-using appliance may be configured to accept the addition of a processor. For example, any sensor within the appliance may be configured to be easily accessed by a processor to accept or store data. In some embodiments, an integrated processor may be either built into the water-using appliance during manufacturing or may be added at a later point.

A processor may be configured to receive, from the at least one sensor, current water usage information. Water usage information refers to any measurements related to the water consumption by the water-using device, and may include the water flow rate or the total consumption over time. The measurement of water usage may be monitored and tracked to very low levels of flow over time. A processor may compare the current water usage information with water usage information stored in memory to determine an existence of a substantial deviation. "Substantial deviation" as used herein refers to a measurement of deviation from the normal expected usage for each water-using appliance. A substantial deviation from the normal expected usage can help determine proper usage and efficiency of the water-using appliance. The processor may be configured to initiate remedial action if a substantial deviation exists.

Initiating remedial action refers to the process where the substantial deviation moves beyond a certain threshold causes an action to occur. In some embodiments, a remedial action can be an alert, an email, or even a shutdown of the water-using appliance. The nature of an action may be determined by the rules associated with each water-using device.

In some embodiments, a water-using appliance may comprise an inlet for connection to a water source, a water outlet, a chamber between the inlet and the outlet configured to enable water to be employed as part of a process, at least one sensor integrated into the appliance for monitoring water usage of the appliance, memory integrated into the appliance for storing water usage information indicative of normal operation of the appliance, at least one processor integrated into the appliance, the at least one processor configured to: receive from the at least one sensor current water usage information, compare the current water usage information with water usage information stored in memory to determine an existence of a substantial deviation, and initiating remedial action if a substantial deviation exists.

The appliance may also be configured to initiate remedial action such as providing information about options to repair and/or replace the water-using appliance. Remedial action may include providing information about options to repair and/or replace the water-using appliance. In some embodiments, a remedial action available for a water-using appliance may include a recommendation to repair or replace a part that has crossed the substantial deviation threshold. This recommendation may, based upon recommended norms of usage, other data gathered on similar devices, or pattern analysis.

Exemplary Embodiments of Differentiating between Irrigation and Non-Irrigation Events A potential benefit of some embodiments of the present disclosure may include differentiating between irrigation and non-irrigation events. Many commercial and residential properties have irrigation systems that use high volumes of water for extended periods. Those examining flow rates and/or volumes might misinterpret an irrigation event as a pipe burst. An aspect of the present disclosure may be directed to overcome this issue by analyzing and storing water usage profiles for irrigation events. When high-volume water usage is detected, a profile of that usage can be compared with known profiles of irrigation events. If there is a match, no remedial action may be taken.

An aspect of some embodiments may include a system for enabling remedial action in response to detecting abnormal consumption in a distributed water infrastructure, which may include irrigation and non-irrigation appliances. The distributed water infrastructure may contain only irrigation appliances. Alternatively, the distributed water infrastructure may contain only non-irrigation appliances. For example, a system that is useful for identifying irrigation events may also be useful for identifying any high-volume water usage. The water usage may be infrequent, like the infrequent refilling of a swimming pool.

In some embodiments, the system may receive from at least one sensor associated with the distributed water infrastructure signals indicative of water usage in the distributed water infrastructure. The system may, based on the signals, construct a plurality of water event profiles. The system may characterize at least one of the plurality of water event profiles as an irrigation water event profile, and store the at least one irrigation water event profile in memory. The system may receive from at least one sensor, current signals indicative of current water usage in the distributed water infrastructure. The system may construct a current water event profile based on the signals indicative of current water usage. The current water event profile may share characteristics with an abnormal consumption in the distributed water infrastructure.

In some embodiments, the system may compare the current water event profile with at least one irrigation water event profile stored in memory. When the current water event profile substantially matches the at least one irrigation water event profile, the system might not initiate remedial action. The system might not initiate remedial action despite detecting that a current water event profile shares characteristics with abnormal consumption in the distributed water infrastructure, because the current water event profile matches a known exception.

In some embodiments, a system for enabling remedial action in response to detecting abnormal consumption in a distributed water infrastructure that may include irrigation and non-irrigation appliances, may receive from at least one sensor associated with the distributed water infrastructure signals indicative of water usage in the distributed water infrastructure. The system may, based on the signals, construct a plurality of water event profiles, and characterize at least one of the plurality of water event profiles as an irrigation water event profile. The system may store the at least one irrigation water event profile in memory. The system may receive, from the at least one sensor, current signals indicative of current water usage in the distributed water infrastructure, and construct a current water event profile based on the signals indicative of current water usage, wherein the current water event profile shares characteristics with an abnormal consumption in the distributed water infrastructure. The system may compare the current water event profile with the at least one irrigation water event profile stored in memory, and when the current water event profile substantially matches the at least one irrigation water event profile, avert remedial action despite the current water event profile sharing characteristics with abnormal consumption in the distributed water infrastructure.

In some embodiments, the at least one processor may be further configured to initiate remedial action if the current water profile does not substantially correspond to the at least one irrigation water event profile. The remedial action may include sending a notification to a system administrator and providing the system administrator with an ability to remotely control a valve in the distributed water infrastructure.

In some embodiments, an irrigation event may demonstrate a relatively large spike in the amount of water consumed relative to non-irrigation consumption. An irrigation event may be differentiated from non-irrigation events by a significantly higher flow rate of water. The flow rate of water during an irrigation event may be at least one of: 10%, 20%, 30%, 40%, 50%, 100%, 150%, or 200% larger than regular non-irrigation water consumption. The flow rate of water during an irrigation event may be greater than 200% of normal water consumption. The system for initiating remedial action may identify issues with the irrigation system by determining that a water consumption event is an irrigation event, but that the water consumption varies in at least one of flow rate and flow volume, as compared to a normal irrigation event.

In some embodiments, the water irrigation profile may include a 50-100 ml of water flow in no more than at least one of 0.1, 0.15, 0.18, 0.2, 0.3, 0.4, and 0.5 seconds. The water irrigation profile may include a 50-100 ml of water flow in less than 0.18 seconds. The water irrigation profile may include 100+ ml of water flow in less than 0.18 seconds. The water irrigation profile may include a 100 ml of water flow in less than 0.18 seconds. The water irrigation profile may include a 50 ml of water flow in less than 0.18 seconds. The water irrigation profile may include a 75 ml of water flow in less than 0.18 seconds.

Exemplary Embodiments of Health and Lifestyle Predictions Based on Detected Water Usage An aspect of some embodiments may include utilizing a recognized correlation between water usage and a resident's health and lifestyle. For example, if during a period when a resident is expected to be at home, water usage goes to zero, it may be an indicator that the resident is incapacitated, and remedial action may be initiated. A dramatic increase in toilet flushes may be an indicator of a gastrointestinal disorder, and remedial action may be initiated. A tap left running may be an indicator of dementia, and remedial action may be initiated. The indicator may be general to all consumers. The indicator may be applied only to users as requested or determined by a user. The indicator may be based on a particular consumer's usage patterns. For example, if the resident has a usual pattern of water usage during specific times of the day, deviations from that schedule may be used to help inform whether there is any change in the resident's health or lifestyle.

An aspect of some embodiments may include a detection system for a distributed water infrastructure, where the system may be configured to determine at least one of a human health or lifestyle state from water usage patterns in the distributed water infrastructure. A detection system may be to any apparatus that can sense water usage characteristics, and may include a water meter of any kind, a water sensor, or a plurality of water sensors. A water usage pattern may be a collection of signals that form an identifiable or unique combination that can be associated to a specific water usage.

The ability to identify and track the frequency that water consumers use certain water appliances enables the ability to associate human behavior, health condition, and life style to one or more water usage patterns (or a lack of usual water usage patterns). For example, a water usage pattern associated with a bath/shower may be used to determine health conditions according to the following exemplary factors: the indication of a bath, bath versus shower, length of shower, or not using the bath for a long period of time. Any of these factors may be used alone or in combination, together or with other factors, including the absence of such factors, to determine the health or hygiene of a particular water consumer.

For example, a water usage pattern associated with a toilette may be used to generate information on the frequency of use of the toilette. By way of example, such information on the frequency of use of the toilette may indicate that there is a digestive or bladder problem.

The combination of multiple water usage patterns can be used to holistically determine the water consumer's health. For example, the water user's hygiene habits can be determined if there is a signal for washing hands after flushing the toilet. The frequency of handwashing, or the time of day that concentrates handwashing versus not using water at all, may indicate wake-up times or going to sleep times.

In some embodiments, water appliance usage and frequency may be used to determine a water consumer's health or lifestyle. For example, the frequency that a liquid dispenser, such as a water bar, kiosk, or coffee machine is used may indicate whether the water user is well hydrated. The usage of a laundry machine or dishwasher may be an indicator for a water consumer's lifestyle or health. The use of water for irrigation may be an indicator for a water consumer's lifestyle or health.

In some embodiments, other factors aside from health and lifestyle can be determined from the water usage information. For example, water usage information may be used to determine the number of cars in an automated car washing facility, the amount of time that an office was active, or the amount of time a cleaning team took to wash something. Additionally, the system may be able to detect fraudulent usage of water. For example, the use of water when it is expected that no water should be used may indicate theft of water.

In some embodiments, a detection system may comprise at least one processor. The at least one processor may be configured to receive from at least one sensor associated with the distributed water infrastructure signals indicative of water usage in the distributed water infrastructure.

In some embodiments, the at least one processor may be configured to determine detected patterns of signals. The at least one processor may be configured to access a database of a plurality of stored water usage patterns, where each stored water usage pattern may be associated with at least one human health or lifestyle state. A database may refer to physical memory that can be either locally in a computer, including any system with memory and a computing device, and storage services in a cloud. A water usage pattern can be stored in any type of database. The database can be accessed in a real-time situation or in non-real-time situations in order to retrieve data, such as water usage patterns.

In some embodiments, each stored water usage pattern may be associated with at least one human health or lifestyle state. Not every water usage pattern may be associated with at least one human health or life style. In some embodiments, a combination of patterns may provide an indication of human behavior. For example, significant change in a single water usage pattern (such as a longer than average shower) may indicate a change in lifestyle or health state. A combination of patterns (such as a toilette flush with or without hand washing and the frequency of toilette flushes) may indicate a change in lifestyle or health state.

In some embodiments, the at least one processor may be configured to compare at least one detected pattern with at least some of the plurality of stored water usage patterns. The at least one processor may be configured to, based on the comparison, determine that at least one detected pattern substantially corresponds to at least one of the plurality of stored water usage patterns in the database.

In some embodiments, the at least one processor may be configured to institute a remedial action for a human health or lifestyle state associated with the at least one stored water usage patterns. A system may be configured to establish a baseline of normal behavior, and provide an indication if a pattern or plurality of patterns substantially divert from the normal. As a non-limiting example, a regular shower-length average as detected in a specific house may be 7 minutes with a standard deviation of 3 minutes, so if a detected shower length is three standard deviations greater than the average shower length, the system may initiate a remedial action.

In some embodiments, systems and methods according to the present disclosure, may employ and/or create rules to indicate a human state. As a non-limiting example, a manual or automatic method may determine that a frequency of toilette flushes during night hours greater than some number (x) may be abnormal, and be a possible indication for prostate problem. As a non-limiting example, a manual or automatic method may determine that the lack of toilette flushes during morning hours in an occupied apartment in an elderly care facility may be abnormal and initiate a remedial action. If an abnormal activity indicates a possible life-threatening condition, a remedial action may be to immediately try to contact the tenant.

In some embodiments, one of the plurality of stored usage patterns may include a signal indicating that hands are washed after using the toilets. A toilet flush may have a distinctive, easy to recognize, repeatable pattern of water usage. A basic hygiene practice is that, after every use of toilets, people must wash their hands properly in order to prevent the transfer of germs and other communicative diseases. In some embodiments, washing hands also creates a clear pattern of water usage. The lack of a washing hands pattern in conjunction with a toilets flush pattern can indicate an unhealthy habit. A washing hand pattern that has volume or duration less than a specific threshold can also indicate the same. Such indication in a food industry facility should raise an immediate alarm and a corrective action.

In some embodiments, one of the plurality of stored usage patterns may include an extended period of non-water use wherein the associated health state may be an individual's incapacity, where the remedial action may be to send a message to a contact indicating the probable incapacity. A message may be sent to any individual, group of individuals, safety system, security system, network operation center, or any other entity that has interest on receiving data and alerts from the system.

In some embodiments, an extended period of non-water use may indicate the incapacity of an end user. Healthy life habits involve regular use of water. A typical day for a healthy individual usually includes using water for flushing toilets, washing hands, washing dishes, drinking, taking a shower, cleaning the house, etc. An irregular or extended period of non-water usage might give an early warning of a health state or even an acute state of incapacitation. Sending an alert during an irregular period of non-water usage may be a non-intrusive way to monitor the health of an at-risk person.

In some embodiments, one of the plurality of stored usage patterns may include an amount of water usage below a threshold, where the associated health state may be unhealthiness and the remedial action may be to send a message to a remote recipient indicating the probable unhealthiness. A reduction of water usage or a reduction of a certain water usage or the absence of certain water usage might give an early warning of a health state or even an acute state of incapacitation.

In some embodiments, one of the plurality of stored usage patterns may include leaving on a water-using device past a threshold, where the associated health state may be dementia and the remedial action may be to send a message indicating a probability of dementia. Leaving the water running beyond the usual average usage can indicate that one has forgot to turn it off or lost the ability to do so. A threshold could be set up for each type of usage based upon the average or any type of prior knowledge. The water-using device may be a faucet.

In some embodiments, one of the plurality of stored usage patterns may include a number of toilet flushes above a threshold, where the associated health state may be a digestive disorder and the remedial action may be to send a message indicating a probable digestive disorder. A digestive disorder may be a health condition that is usually associated with unusual use of water such as increasing visits to the toilettes, shower, and washing of hands.

Frequency of toilette flushes during night hours greater than a certain amount may indicate possible prostate problems. Alternatively, the lack of toilette flushes during morning hours in an occupied apartment in an elderly care facility may indicate a possible life-threatening condition, and may trigger a remedial action to immediately try to contact the tenant.

In some embodiments, the processor may be further configured to determine from water usage patterns when an inhabitant is likely away from home and to suspend comparing during away periods. Some usage patterns are associated with automated machines (i.e. laundry, dishwasher, automated irrigation, etc.) and others with human behavior (toilette, faucet usage, shower, etc.).

If for a period of x minutes or more human usage of water is not detected then one may conclude that the tenants are away or sleeping. The time of day can give a good indication for the former or the later. The x minutes can be a fixed number or can be learned from the past, manually, or by automated machine learning.

Figure 8A:
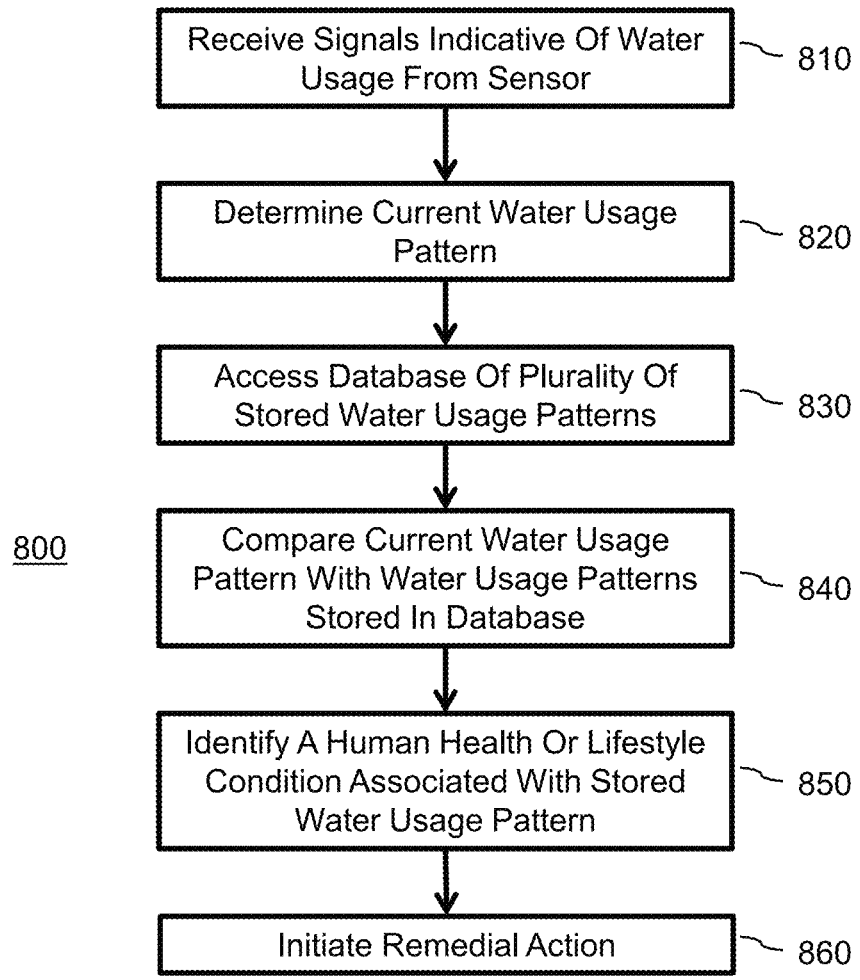
FIG. 8a illustrates an exemplary method for estimating a health and lifestyle status based on water consumption.

FIG. 8*a* illustrates an exemplary method 800 for estimating a health and lifestyle status based on water consumption. The operations of method 800 discussed herein are intended to be illustrative. In some embodiments, method 800 may be implemented with one or more additional operations not described, and/or without one or more of the operations discussed. Additionally, the order in which the operations of method 800 are illustrated in FIG. 8*a* and described herein is not intended to be limiting.

In some embodiments, method 800 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all the operations of method 800 in response to instructions stored electronically on an electronic storage medium. The one or more processing devices may include one or more devices configured through hardware, firmware, and/or software to be specifically designed for execution of one or more of the operations of method 800.

In some embodiments, at operation 810, at least one processor may be configured to receive from at least one sensor associated with the distributed water infrastructure signals indicative of water usage in the distributed water infrastructure. At operation 820, at least one processor may be configured to determine from the signals indicative of water usage a current water usage pattern. At operation 830, at least one processor may be configured to access a database of a plurality of stored water usage patterns, wherein at least one stored water usage pattern may be associated with at least one human health or lifestyle state. At operation 840, at least one processor may be configured to compare at least one current water usage pattern with at least some of the stored water usage patterns. At operation 850, at least one processor may be configured to, based on the comparison, identify a human health or lifestyle condition reflected by the current water usage pattern. In some embodiments, at operation 860, at least one processor may be configured to institute a remedial action corresponding to the identified human health or lifestyle state.

Figure 8B:
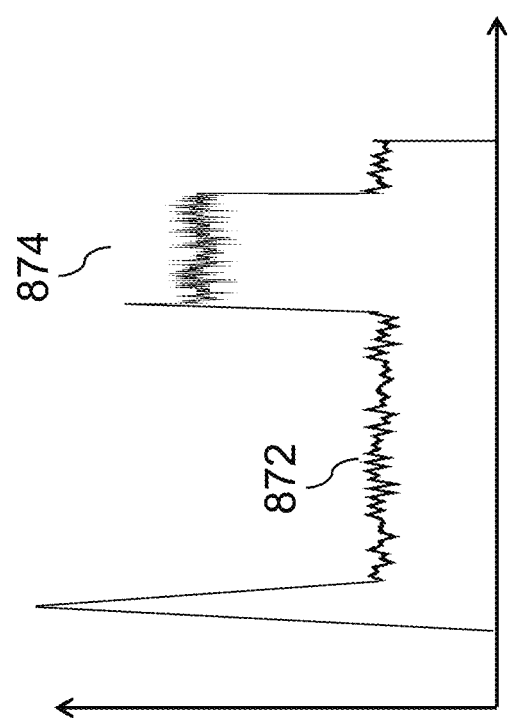
FIG. 8b illustrates an exemplary water usage pattern for detecting a handwashing state after the use of a toilet.

FIG. 8b illustrates an exemplary water usage pattern for detecting a handwashing state after the use of a toilet. FIG. 8b shows a water usage signal over time, with flow rate on the y-axis and time on the x-axis. FIG. 8b shows a water usage pattern 872 that may be determined to be toilet flushing. Water usage pattern 872 may be determined by any method consistent with identification herein, such as the non-limiting examples of through a threshold method, guided machine learning, or automatic machine learning. Water usage pattern determination may be assisted by a neural network, whereby a system may progressively improve performance to determine, identify, and compare water usage patterns by considering examples. In some embodiments, a neural network may be used without task-specific programming.

Similarly to water usage pattern 872 for toilet flushing, water usage pattern 874 corresponding to handwashing may be measured and identified. FIG. 8b shows two overlapping water usage profiles, but in some embodiments, for example depending on the flow pattern of the toilet flushing and/or being refilled after flushing, overlapping water usage profiles may not exist, and the water usage profiles may be distinct. Water usage pattern 874 might not be present, which would indicate that a user has not washed hands. The duration of water usage pattern 874 may be shorter than some threshold period of time, which may indicate that hands were not thoroughly washed. Water usage patterns 872 and 874 might not be present, which may indicate that no users are within a household, and/or a user may be ill in the household.

In some embodiments, the measurement of water usage may be performed by any one of the systems described herein, and/or the measure of water usage may be performed by a third-party water measuring device. The measurement of water usage may be performed by separate devices distributed by distance, where the processing operations may be performed locally or at a central location. The processing operations may be performed in real time, and/or at a later time. The processing operations may also be provided by distributed parallel or cloud computing infrastructures with data and results transported to the cloud or a parallel processor using wireless or wired networks.

In accordance with the present disclosure, some of the embodiments described herein provide examples of the novel benefits of event-based leak detection systems and methods. In some embodiments, a measurement of the number of liters consumed as a function of time may be transformed into a water usage pattern that has a particular fingerprint or water usage pattern. A water usage pattern may be determined by any method consistent with identification describe herein, such as the non-limiting examples of: event-based threshold method, guided machine learning, or automatic machine learning. Water usage pattern determination may be assisted by a neural network, where a system may progressively improve performance to determine, identify, and compare water usage patterns by considering examples. In some embodiments, a neural network may be used without task-specific programming.

In various alternative methods, estimating a health and lifestyle status based on water consumption may be implemented by alternative methods of receiving water information, and employing event-based leak detection systems and methods to provide granularity of water usage to an end user.

Exemplary Embodiments of Differentiating between Multiple Overlapping Water Events Traditionally, a single upstream water sensor may have difficulty differentiating between water usage of multiple downstream water appliances. A potential benefit of systems and methods of the present disclosure may be that some embodiments may address this issue by analyzing water usage signals for a first sustained increase and a first steady state plateau, followed by a second sustained increase and a second plateau that leads to a total flow rate greater than the first flow rate by itself. Each water consumption event may have its own characteristics. Therefore, when one of the events ends, the system may determine which of the overlapping events has ended by analyzing which characteristics are missing from the continuing water usage. In an alternative, a mixed event may be deconstructed into two or more components by using inflection locations to deconstruct mixed events in subcomponents. In some embodiments, a subcomponent, from an overlapping event that has been deconstructed, may be compared against prior stored signatures of subcomponents.

In some embodiments, a system could may be configured to detect when water flow rate is above a certain threshold to be identified as a water event, identify the sustained increase in water flow rate as a first event, detect a second sustained increase above a second threshold during the first event, and identify a second event. If a drop is approximately the same as the sustained increase of one of the sustained increases, the system may be able to identify which event has ended.

By way of a non-limiting example, if a shower is taken during a laundry cycle, and the shower consumes 2 gallons per minute, then the consumption and cessation of water use by the shower can be determined by an increase in water flow rate by 2 gallons per minute, and followed by a decrease in water flow rate by 2 gallons per minute. This procedure may be performed when two or more simultaneous water consumption events occur.

An aspect of the disclosure may be directed to a system for differentiating between overlapping water events in a distributed water infrastructure including a plurality of water appliances, the system comprising at least one processor. Overlapping water events are two or more events that occur simultaneously or partially-simultaneously in time, in a distributed water system, where each event originates from a unique or identifiable water consumer connected to the water system.

In some embodiments, the at least one processor may be configured to repeatedly measure at least one overall water usage indicator of the distributed water infrastructure, the at least one water usage indicator including at least one of an overall flow rate and an overall flow volume in the distributed water infrastructure. The overall flow rate of the water flowing in a distributed water system may be a measure of the aggregate flow rate of the water that may be flowing through all the water consumers connected to the water system at any moment in time.

In some embodiments, repeated measuring occurs at a single location upstream of the plurality of water appliances. At least one processor may be configured to detect a first sustained increase in the repeated measurements.

The at least one processor connected to the distributed water infrastructure may detect a first significant increase in the flow rate that corresponds to the use of a single water-consuming appliance in the distributed water infrastructure. In some embodiments, a significant increase in the flow rate may be an increase to a flow-rate that is over a minimum flow rate, which may represent the minimal normal flow rate detected for all water consumers connected to the water system.

In some embodiments, the at least one processor may be configured to store in memory a first indicator of the first sustained increase. A first indicator of the first sustained increase in flow rate may be a quantitative value that encapsulates the increase in flow-rate. This value may be, by way of non-limiting examples, an absolute flow rate, a flow rate difference, and a derivate thereof.

In some embodiments, the at least one processor may be configured to attribute in memory the first sustained increase to a first water event in the distributed water infrastructure. Attribution may be done by associating a sustained increase with a water event. Attribution might not include an indicator that is tied to a specific event, but rather may be a general indicator that some event has occurred. The at least one processor may attribute the first sustained increase to a first water event by storing the time that the first sustained increase occurred. The at least one processor may be configured to store in memory the magnitude of the first sustained increase. Measures of the magnitude of the first sustained increase may be, for example, the average flow rate of the sustained increase and the duration of time for the increase in flow rate to be sustained.

In some embodiments, the at least one processor may be configured to attribute the first sustained increase to a first water event without specifying the source or type of water event. Any time that a sustained increase occurs, the at least one processor may be configured to identify the type of water event that has occurred.

In some embodiments, attributing in memory a water event to the first sustained increase may include identifying a particular appliance associated with the first sustained increase. Attributing in memory the first sustained increase to a first water event may include accessing previously stored fingerprints of water events associated with known appliances in the distributed water system, and determining a match between at least one characteristic of the first sustained increase and a characteristic of a particular fingerprint.

In some embodiments, certain water events may have identifiable characteristics that may aid in the identification of that event, and these identifiable characteristics, or fingerprints, may be stored in memory. The stored fingerprints may be associated with known water appliances. The stored fingerprints may be associated with a type of water use that is not specific to a single water appliance. The at least one processor may be configured to identify a particular appliance associated with the first water event-based on at least the first indicator and the third indicator. The at least one processor may, during the first sustained increase, detect in the overall measurements a second sustained increase.

A second significant increase in the flow rate in the aggregate flow rate signal may correspond to the use of a second water-consuming appliance in the distributed water infrastructure simultaneously with the first water-consuming appliance whose sustained flow rate was detected earlier and may be ongoing. The at least one processor may be configured to, during the first sustained increase, detect in the repeated overall measurements a second sustained increase. The at least one processor may be configured to store in memory a second indicator of the second sustained increase. The at least one processor may be configured to attribute, in memory, the second sustained increase to a second water event in the distributed water infrastructure.

In some embodiments, the at least one processor may be configured to, following initiation of the first sustained increase and the second sustained increase, detect in the repeated measurements a decrease in the overall water usage indicator. A decrease in the overall water usage indicator may be a quantitative value that encapsulates the decrease in flow-rate that may include two or more consecutive signals indicative of water usage in a distributed water system. The signals may each represent an aggregate measure of the water usage over all water-consuming appliances that are connected to the system. This value may be measured as absolute flow rate or a flow rate difference or any derivate thereof.

In some embodiments, the at least one processor may be configured to attribute a third indicator to the decrease. The process of attributing a third indicator may refer to the process of assigning and retaining a quantitative value representing the decrease in flow rate. This value may be the third one retained after two sustained increases in flow rate. By way of non-limiting example, this value may be an absolute flow rate, a flow rate difference, or any derivate thereof.

In some embodiments, the at least one processor may be configured to compare the third indicator with at least one of the first indicator and the second indicator stored in memory to determine a substantial match and determine a cessation of at least one of the first water event and the second water event. A substantial match between one of the two previous indicators of sustained increases in the overall consumption and a third indicator of a decrease in the overall consumption may be determined by calculating a distance measure between the third indicator and each of the first two indicators—to determine to which it may be most similar and if it is similar enough based on whether the difference is within some acceptable, pre-determined bounds. In this case, a substantial match between the third indicator and the one most similar to it may be established. The distance measure used may be any appropriate similarity or difference measure.

In some embodiments, the at least one processor may be configured to initiate an action based on a cessation determination. A cessation of consumption from a particular consumer connected to the distributed water infrastructure may be determined when a substantial match has been found between an indicator of a sustained decrease with a previous indicator of sustained increase in the overall consumption indicator. Once the end of an event has been determined an action may be taken, which may include storing all data about the event in a database, including, for example, the raw consumption signals, the volume, the duration, the start-time of the event and any derivatives of this data. The action may also involve triggering algorithms to determine the water consumer or appliance connected to the distributed water infrastructure from where the ended event originated.

In some embodiments, the initiated action may include recording, in memory, usage of at least one of the plurality of water appliances. The initiated action may include transmitting an alert to a remote location indicating the water event.

An aspect of the disclosure may be directed to a system for differentiating between overlapping water events in a distributed water infrastructure including a plurality of water appliances, the system comprising at least one processor configured to repeatedly measure at least one overall water usage indicator of the distributed water infrastructure. The at least one water usage indicator may include at least one of an overall flow rate and an overall flow volume in the distributed water infrastructure. In the repeated measurements, the processor may be configured to detect a first sustained increase, store in memory a first indicator of the first sustained increase, attribute in memory the first sustained increase to a first water event in the distributed water infrastructure. During the first sustained increase, the at least one processor detect in the repeated overall measurements a second sustained increase, store in memory a second indicator of the second sustained increase, attribute in memory the second sustained increase to a second water event in the distributed water infrastructure. Following initiation of the first sustained increase and the second sustained increase, the at least one processor may detect, in the repeated measurements, a decrease in the overall water usage indicator, attribute to the decrease to a third indicator, compare the third indicator with at least one of the first indicator and the second indicator stored in memory to determine a substantial match, thereby determining a cessation of at least one of one of the first water event and the second water event, and initiate an action based on the cessation determination.

In some embodiments, the first sustained increase may be an increase beyond a first threshold. A first threshold may be a quantitative value defining the minimum acceptable increase in flow rate for a first event to be considered legitimate. This value may be determined using prior knowledge about the sustained flow rates of other legitimate consumption events occurring on their own in a distributed water infrastructure. For example, a threshold may be a percentage, an amount above signal to noise, or an amount that may be above the smallest amount of water.

In some embodiments, the at least one processor may be configured to determine the first threshold by aggregating water usage data of water appliances known to be currently operating in the distributed water infrastructure. A first threshold may be determined to be less than the smallest water consumer in a distributed water infrastructure.

In some embodiments, the second sustained increase may be an increase beyond a second threshold associated with the second sustained increase. A second threshold may be a quantitative value defining the minimum acceptable increase in flow rate for a second event, which begins while a first event may be ongoing, in order to be considered legitimate. This value may be determined using prior knowledge about the increase in flow rates of legitimate consumption events that start while a first event may be ongoing in the same distributed water infrastructure.

In some embodiments, the first threshold and the second threshold are substantially equal. The threshold associated with the first sustained increase and the threshold for the second sustained increase may be between 0.001 and 10 liters/minute. The threshold may be between 0.01 and 1 liters/minute. The threshold may be approximately 0.1 liters/minute. The first threshold and the second threshold may be less than about 1 liter/hour.

In some embodiments, the indicator may be a pattern of water usage over a period of time. The indicator might not be a single indication, and may also include indicators that occur during an extended period of time during the first sustained increase. By way of non-limiting example, an exemplary indicator may be the average flow rate during the first sustained increase. At least one of the first sustained increase and the second sustained increase may include a pattern that varies over time. By way of non-limiting example, an exemplary indicator may be the pattern for washing machine.

In some embodiments, prior to the first sustained increase, at least one processor may be configured to detect an initial spike in water usage, and to attribute in memory the first sustained increase to the first water event if the spike is detected.

An initial spike in a pattern of water usage may be a rapid increase in flow rate that occurs at the beginning of the pattern when a water consumer or appliance connected to a distributed water infrastructure starts to consume water. This spike might not represent the actual flow rate that the consumer or appliance is consuming water but rather may be attributed to the pressure difference in the water system on either side of the consumer or appliance.

A substantial plateau in a pattern of water usage may constitute a sequence of signals indicative of water consumption of uniform flow rate that occurs following a spike in flow rate that occurs at the start of the same pattern. Such a plateau may represent the actual flow rate that the consumer or appliance is consuming water. A remedial action may include recording in memory usage information attributable to water appliance usage. The first water event may be associated with a first water appliance and the second water event may be associated with a second water appliance. The at least one processor may be configured to identify a first water appliance associated with the first water event and a second water appliance associated with the second water event.

In some embodiments, the at least one processor may be configured to identify a first water appliance associated with the first water event before the use of a second appliance begins. Identification may begin before or after the usage begins. The at least one processor may be configured to differentiate between water events by identifying inflexion locations in the at least one overall water usage indicator of the distributed water infrastructure. An inflexion point may be a first derivative, or a second derivative.

In some embodiments, the at least one processor may be configured to differentiate between water events by identifying at least two inflection locations. The at least one processor may be configured to differentiate between water events by identifying inflexion locations and deconstructing overlapping events into subcomponents based on prior stored signatures of the subcomponents. Only the beginning of a water usage profile might be used to identify a water event.

The signatures of the subcomponents may be the unique consumption patterns of the individual water consumers or appliances that are connected to some distributed water infrastructure. Each signature constitutes a group of signals indicative of water usage in time and may occur simultaneously with other signatures to form an aggregated mixed signal.

In some embodiments, the at least two inflection locations may be between periods of at least one of no consumption or substantially uniform consumption.

A system may differentiate between water events by identifying inflection locations. A general process may include segmenting the signals indicative of water usage into individual water events using inflection locations, where the inflection points are either rapid increases in the consumption rate or rapid decreases in the consumption rate between periods of no consumption or uniform consumption.

Deconstructing mixed events into subcomponents refers to a process of separating multiple signals indicative of simultaneous water usage, from more than one consumer or appliance, into groups of signals each representing the consumption of a single water consumer or appliance connected to the distributed water infrastructure. The deconstruction of the mixed events may be carried out by a mathematical algorithm that resamples the mixed signal to produce the individual signals.

Figure 9:
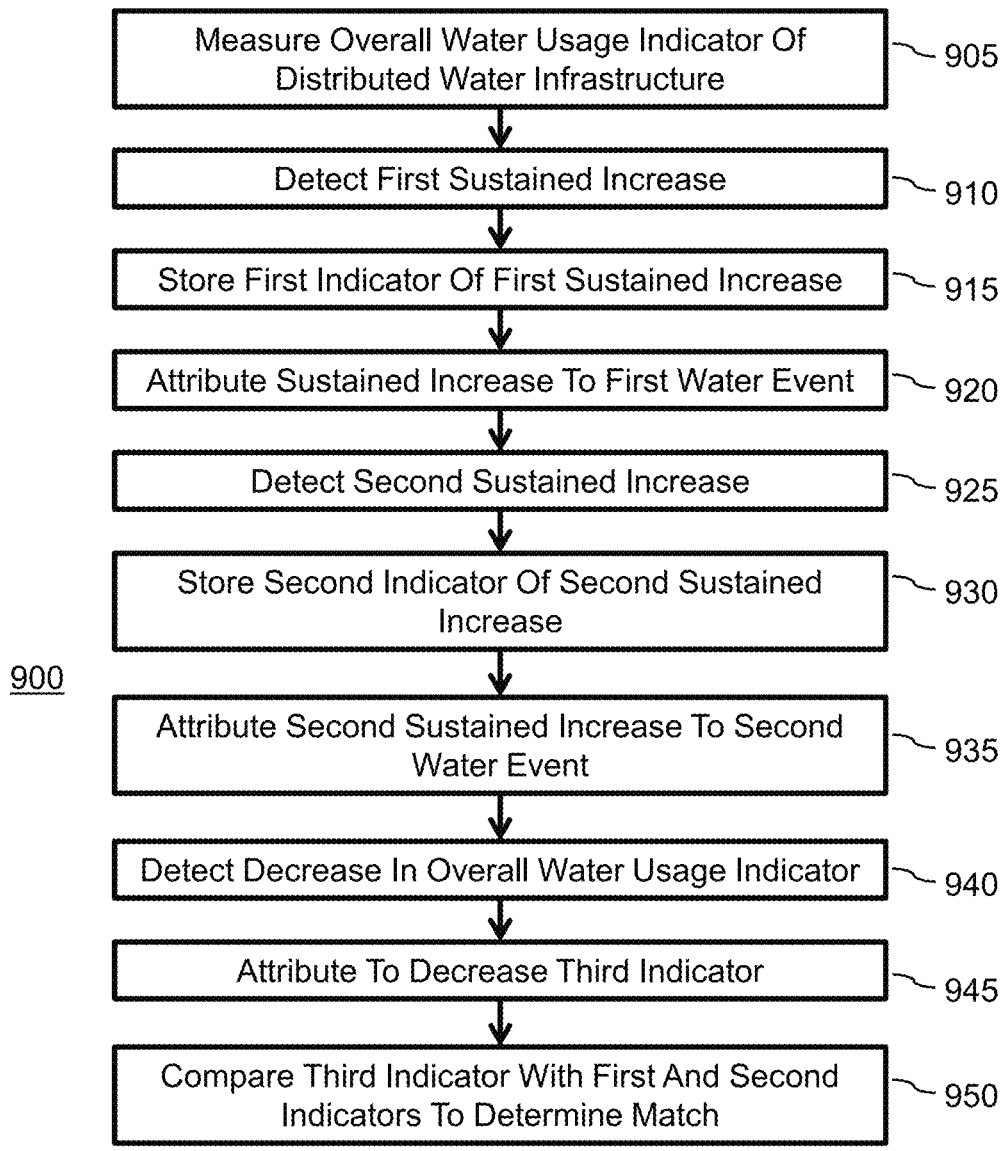
FIG. 9 illustrates an exemplary method for differentiating between overlapping water events in a distributed water infrastructure with a plurality of water appliances.

FIG. 9 illustrates an exemplary method 900 for differentiating between overlapping water events in a distributed water infrastructure including a plurality of water appliances. The operations of method 900 discussed herein are intended to be illustrative. In some embodiments, method 900 may be implemented with one or more additional operations not described, and/or without one or more of the operations discussed. Additionally, the order in which the operations of method 900 are illustrated in FIG. 9 and described herein is not intended to be limiting.

In some embodiments, method 900 may be implemented in one or more processing devices. The one or more processing devices may include one or more devices executing some or all the operations of method 900 in response to instructions stored electronically on an electronic storage medium. The one or more processing devices may include one or more devices configured through hardware, firmware, and/or software to be specifically designed for execution of one or more of the operations of method 900.

In some embodiments, at operation 905, at least one processor may be configured to repeatedly measure at least one overall water usage indicator of the distributed water infrastructure, the at least one water usage indicator including at least one of an overall flow rate and an overall flow volume in the distributed water infrastructure. At operation 910, at least one processor may be configured to detect, in the repeated measurements, a first sustained increase. At operation 915, at least one processor may be configured to store in memory a first indicator of the first sustained increase. At operation 920, at least one processor may be configured to attribute in memory the first sustained increase to a first water event in the distributed water infrastructure. At operation 925, at least one processor may be configured to, during the first sustained increase, detect in the overall measurements a second sustained increase. At operation 930, at least one processor may be configured to store in memory a second indicator of the second sustained increase. At operation 935, at least one processor may be configured to attribute, in memory, the second sustained increase to a second water event in the distributed water infrastructure. At operation 940, at least one processor may be configured to detect, following initiation of the first sustained increase and the second sustained increase, in the repeated measurements, a decrease in the overall water usage indicator. At operation 945, at least one processor may be configured to attribute to the decrease a third indicator.

In some embodiments, at operation 950, at least one processor may be configured to compare the third indicator with at least one of the first indicator and the second indicator stored in memory to determine a substantial match and determine a cessation of at least one of the first water event and the second water event. The measurement of water usage may be performed by any one of the systems described herein, and/or the measure of water usage may be performed by a third-party water measuring device. The measurement of water usage may be performed by separate devices distributed by distance, where the processing operations may be performed locally or at a central location. The processing operations may be performed in real time, and/or at a later time. The processing operations may also be provided by distributed parallel or cloud computing infrastructures with data and results transported to the cloud or a parallel processor using wireless or wired networks.

In accordance with the present disclosure, some of the embodiments described herein provide examples of the novel benefits of event-based leak detection systems and methods. A measurement of the number of liters consumed as a function of time may be transformed into a water usage pattern that has a particular fingerprint or water usage pattern. A water usage pattern may be determined by any method consistent with identification herein, such as the non-limiting examples of: event-based threshold method, guided machine learning, or automatic machine learning. Water usage pattern determination may be assisted by a neural network, where a system may progressively improve performance to determine, identify, and compare water usage patterns by considering examples. In some embodiments, a neural network may be used without task-specific programming.

In some embodiments, differentiating between overlapping water events in a distributed water infrastructure including a plurality of water appliances may be implemented by alternative methods of receiving water information, and employing event-based leak detection systems and methods to provide granularity of water usage to an end user.

Figure 10A:
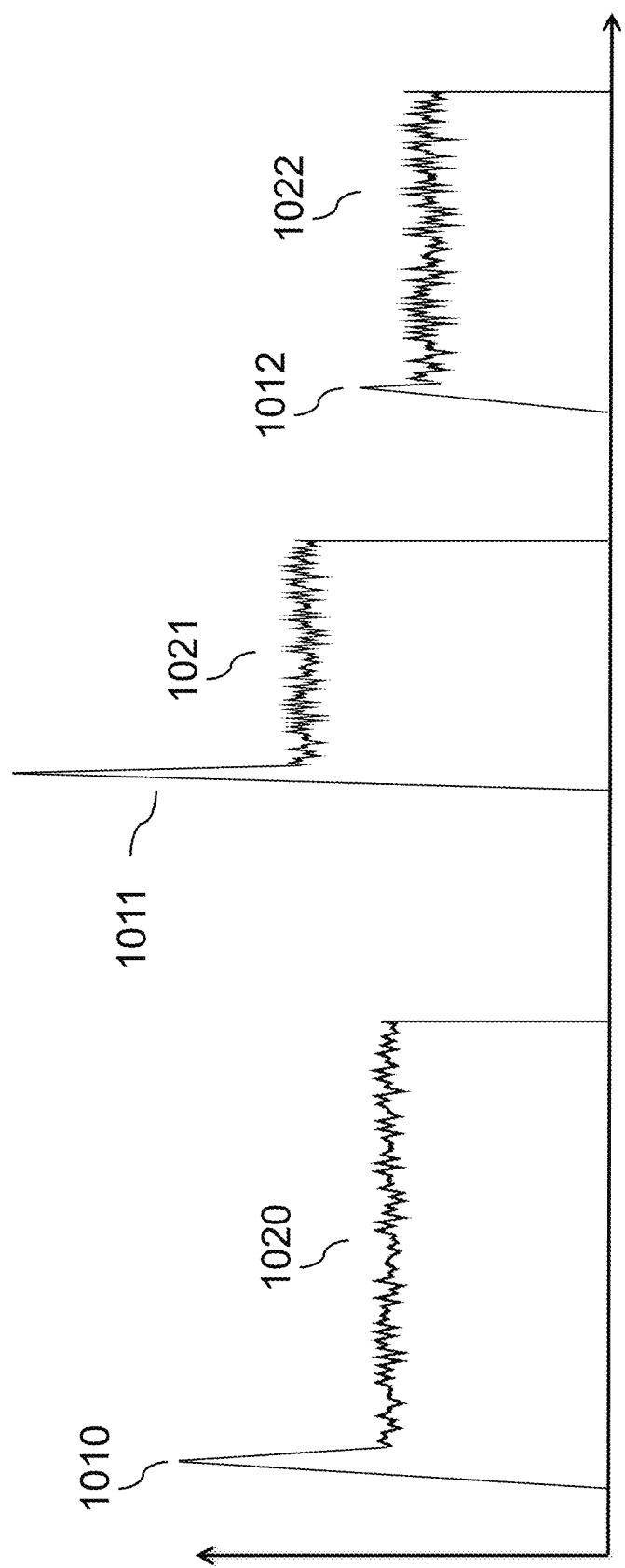

FIG. 10a illustrates an exemplary water usage pattern over time, with flow rate on the y-axis and time on the x-axis. The exemplary water usage pattern may comprise a spike 1010 in the flow rate at the beginning. In other examples, there might not be spike at the beginning of a water usage pattern. A spike may be large, or may be a different magnitude such as spikes 1011 and 1012. The increase in the water flow rate may be characteristic of a type of water usage. After initiation of water usage, the flow rate may take a period of time to reach a steady state of water flow.

The exemplary water usage pattern in FIG. 10a may comprise a steady state flow rate 1020 during the exemplary pattern. In some embodiments, a steady state flow rate may be a different magnitude, such as steady state flow rates 1021 and 1022. Steady state flow rate 1020 may have a certain level of noise associated with the water usage. The signal to noise ratio may be indicative of a type of water usage. The entirety of the water usage may comprise at least one unique water usage identifier that is used to determine a type of water usage event. The entirety of the water usage may comprise at least one weak water usage identifier that is used to assist in determining a type of water usage event. The combination of several water usage identifiers may be used to identify or guess a type of water usage event. A heuristic method that uses simple manually defined rules may be used to determine a type of water usage event. A water usage pattern shown in FIG. 10a may be determined by any method consistent with identification described herein, such as the non-limiting examples of a threshold method, guided machine learning, or automatic machine learning. Water usage pattern determination may be assisted by a neural network, where a system may progressively improve performance to determine, identify, and compare water usage patterns by considering examples. In some embodiments, a neural network may be used without task-specific programming.

Figure 10B:
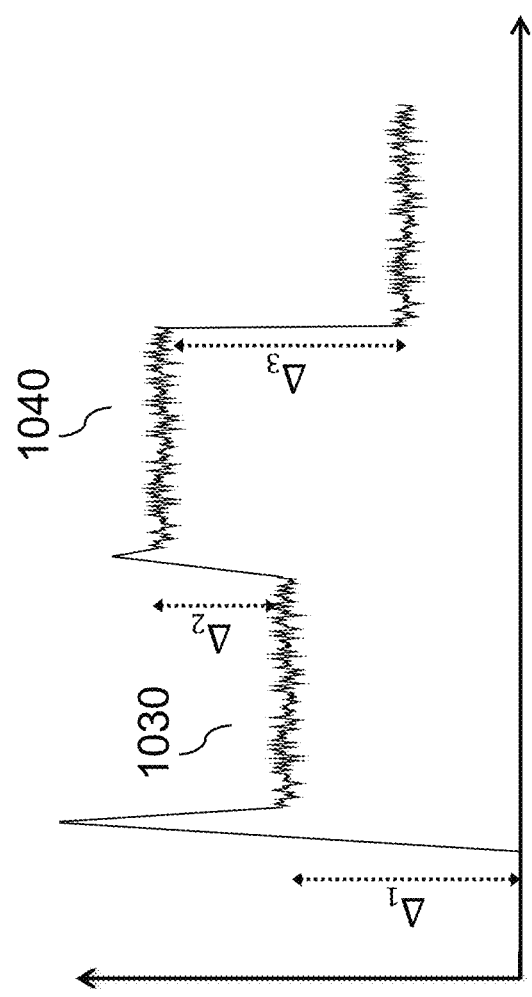

FIG. 10b illustrates an exemplary water usage pattern over time, with flow rate on the y-axis and time on the x-axis. FIG. 10b shows exemplary overlapping water usage patterns, where water usage pattern 1030 overlaps with water usage pattern 1040. As shown in FIG. 10b, in some embodiments, a water usage pattern 1030 may begin before water usage pattern 1040. A steady state flow rate ($\Delta_1$) of water usage pattern 1030 may be different than a steady state flow rate ($\Delta_2$) of water usage pattern 1040. Either water usage pattern 1030 or water usage pattern 1040 may end first. A sustained decrease in steady state flow rate ($\Delta_3$) may match a first water usage pattern steady state flow rate ($\Delta_1$) and be different than a second steady state flow rate ($\Delta_2$). In such an embodiment, where ($\Delta_3$) equals ($\Delta_1$), water usage pattern 1030 can be determined to have been terminated. Water usage pattern 1030 may be differentiated from water usage pattern 1040, by subtracting a contribution of water usage pattern 1040, e.g., second steady state flow rate ($\Delta_2$), from the water usage pattern that begins at ($\Delta_1$) and is assigned a water pattern 1030 during the time period between ($\Delta_1$) and ($\Delta_3$). Similarly, in some embodiments, water usage pattern 1040 may be determined by subtracting a contribution of water usage pattern 1030, e.g., first steady state flow rate ($\Delta_1$), from the water usage pattern that begins at ($\Delta_2$) and is assigned a water pattern 1040 for the period that follows ($\Delta_2$).

Figure 10C:
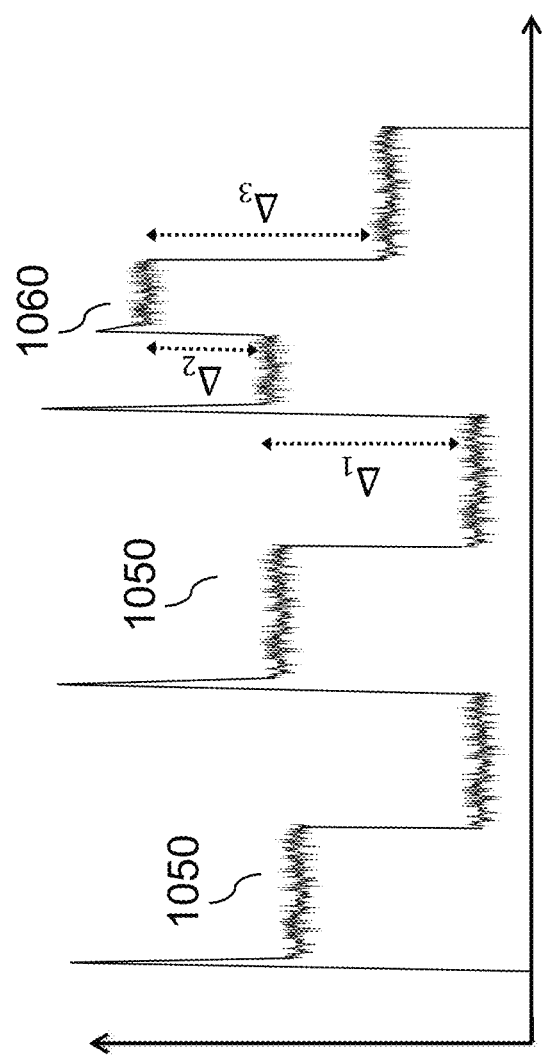

FIG. 10c illustrates an exemplary water usage pattern over time, with flow rate on the y-axis and time on the x-axis. FIG. 10c shows exemplary overlapping water usage patterns, where water usage pattern 1050 may be a repeating water usage pattern, e.g., a washing machine, that overlaps with singular water usage pattern 1060. As shown in FIG. 10c, in some embodiments, a water usage pattern 1050 may begin before water usage pattern 1060. A repeating water usage pattern 1050 might be readily identified by a distinct repeating pattern. An overlapping water usage pattern 1060 might frustrate automatic or manual identification of water usage patterns 1050 and 1060, as the method of identification may rely on easily identifiable repeating patterns. An aspect of the present disclosure may be directed to handling this problem.

For example, a steady state flow rate ($\Delta_1$) of water usage pattern 1050 may be different than a steady state flow rate ($\Delta_2$) of water usage pattern 1060. Either water usage pattern 1050 or water usage pattern 1060 may end first. A first water usage pattern's steady state flow rate ($\Delta_1$) may be different than a second steady state flow rate ($\Delta_2$). A sustained decrease in steady state flow rate ($\Delta_3$) may match a first water usage pattern's steady state flow rate ($\Delta_1$) and be different than a second steady state flow rate ($\Delta_2$). In such an embodiment, where ($\Delta_3$) equals ($\Delta_1$), water usage pattern 1050 can be determined to have been terminated. Water usage pattern 1050 may be differentiated from water usage pattern 1060, by subtracting a contribution of water usage pattern 1060, e.g., second steady state flow rate ($\Delta_2$), from the water usage pattern that begins at ($\Delta_1$) and is assigned a water pattern 1050 for the time period between ($\Delta_1$) and ($\Delta_3$). Similarly, in some embodiments, water usage pattern 1060 may be determined by subtracting a contribution of water usage pattern 1050, e.g., a first steady state flow rate ($\Delta_1$), from the water usage pattern that begins at ($\Delta_2$) and is assigned a water pattern 1060 for the period that follows ($\Delta_2$).

In some embodiments, a water usage pattern may be determined by one or more processing devices. The one or more processing devices may include one or more devices executing some or all of the operations of method 900 in response to instructions stored electronically on an electronic storage medium. The one or more processing devices may include one or more devices configured through hardware, firmware, and/or software to be specifically designed for execution of one or more of the operations of a method, for example method 900.

In some embodiments, several indicators of the water usage pattern may be used to identify a type of water usage. The duration of water usage pattern 1000 may increase. For example, a water usage pattern corresponding to handwashing does not have a pre-determined length of time. The steady state flow rate may increase depending on the water usage. For example, a water usage pattern corresponding to handwashing may use a larger amount of water if both hot and cold water are used. As another example, a faucet may not be fully opened, such that a water usage pattern may have a low steady state flow rate. If one water usage indicator changes, a single water usage indicator may be used to identify a type of water usage. For example, if a duration of water usage changes, a particular flow rate volume and/or the magnitude of noise for a water flow pattern may be used to identify a type of water usage.

FIG. 10d-10f illustrates exemplary water usage patterns over time, with flow rate on the y-axis and time on the x-axis. FIG. 10g further illustrates an exemplary current water usage pattern over time, with flow rate on the y-axis and time on the x-axis, and may include several water usage events.

In some embodiments, a system may be continually measuring water usage, and all types of water usage may be eventually experienced and identified. The types of water usage can be categorized and stored in memory to be compared with and used at a later time.

Exemplary Embodiments of Unrecognized Liquid Events Triggering Remedial Action

An aspect of some embodiments may include detecting water events that trigger remedial actions. These remedial actions may be automatic or require confirmation of an end user. As an alternative to using absolute thresholding, which may be less reliable for abnormal consumption detection, a potential benefit of some embodiments may be that exemplary systems and methods of the present disclosure may learn patterns of system behavior and store them as water events. When a water event is detected that deviates from the normal patterns, the system may recognize the deviation as a likely abnormal consumption and initiate remedial action. If, for example, the duration of an otherwise normal event exceeds a norm, an alert may be signaled (e.g., "Your shower at 8:30 am today was longer than usual. Save water by taking shorter showers!").

An aspect of some embodiments may include a detection system for a distributed water infrastructure, where the system may be configured to identify abnormal water use from water usage patterns in the distributed water infrastructure, the system comprising at least one processor. At least one processor may be configured to receive from at least one sensor associated with the distributed water infrastructure signals indicative of water usage in the distributed water infrastructure. At least one processor may be configured to determine at least one detected pattern of signals, access a database of a plurality of stored water usage patterns, where each stored water usage pattern may be associated with at least one normal water usage pattern. A normal water usage pattern may be a pattern of consumption, constituting a sequence of signals over time indicative of water consumption, that originates from and characterizes the use of a particular water consumer or water-consuming appliance that may be connected to a distributed water infrastructure and therefore represents a typical usage of water in that water system.

In some embodiments, at least one processor may be configured to compare the at least one determined pattern with at least some of the plurality of stored water usage patterns. At least one processor may be configured to determine, based on the comparison, that at least one determined pattern substantially deviates from at least one corresponding stored water usage pattern. At least one processor may be configured to initiate a remedial action when a substantial deviation may be determined. A substantial deviation between two water usage patterns may be a deviation measured using a quantitative distance measure that exceeds a predefined limit. The distance measure may be any quantitative measure of dissimilarity and the limit of the acceptable deviation may be defined as the variance or standard deviation of the distances between acceptable water usage patterns, beyond which the deviation may be considered substantial.

In some embodiments, the remedial action may include closing and opening a valve to send pulses of water to communicate that an abnormal amount of water has been consumed. An abnormal amount of water for a consumption event may be a quantitative value defining a volume of water that is beyond the acceptable volume for a normal consumption event in a distributed water infrastructure. The acceptable volume of a normal consumption event may be a fixed predetermined value or may be learned over a learning period. Pulses of water may include the physical stopping and starting the water flow from the point of view of the end-user of a water-consuming appliance connected to the distributed water infrastructure. The pulses of water will cause the user to experience an intermittent burst of water representing a physical indication of an abnormal consumption event in the water infrastructure.

In some embodiments, the at least one processor may be configured to determine based on the comparison, an identity of a water user associated with the deviation. A water user may be an individual who regularly consumes water in a distributed water infrastructure through the water-consuming appliances connected to that infrastructure.

To determine an identity, the processor associated with the distributed water infrastructure may compare, either completely or partially, a new water consumption pattern with an identified, stored, water consumption pattern associated with an end-user. This may be done using a quantitative distance measure of similarity or dissimilarity to determine if the usage originates from the same end-user.

In some embodiments, the remedial action may include sending a message to a device of the water user. A device of a water user may be an electronic computing device that has the ability to communicate over a network and can therefore send and receive electronic messages. This device may be a mobile phone, a wearable computer, a tablet computer, a laptop computer, a desktop computer, similar devices disclosed herein, or any other variation thereof.

Exemplary Embodiments of Water use Signatures for Identifying Operation of Water Appliances An aspect of the disclosure may be directed to providing water use signatures for identifying the operation of water appliances. A potential benefit of using a water sensor upstream of many water appliances such as toilets, sinks, showers, and washing machines may include the ability to distinguish and track the operation of individual appliances by storing unique water usage signatures for each appliance. Each appliance may have a unique signature that can be associated to that specific appliance. This signature may indicate what appliance is being used. The signature may be based upon clustering, which may be done to create a defined signature for that appliance.

An aspect of the disclosure may be directed to a system for tracking usage of a plurality of water appliances in a distributed water infrastructure. In some embodiments, tracking usage refers to the process of recording water usage of water appliances in a distributed water infrastructure. Tracking usage may include measuring water usage flow and time to deliver a picture of how an appliance has used water, or in what ways a distributed water infrastructure has consumed water.

In some embodiments, the system may comprise at least one processor. The at least one processor may be configured to receive, from a location in the distributed water infrastructure upstream of the plurality of water appliances, historical water usage measurements. The at least one processor may be configured to receive historical water usage measurements from locations upstream of the measuring unit. In this way, any appliance downstream may be measured. Historical water usage measurements refer generally to acts of measuring and storing both usage, flow, time, and water patterns over a period to achieve a unique fingerprint of the water used. The at least one processor may be configured to determine from the historical water usage measurements at least one unique water usage signature associated with each of the plurality of water appliances.

In some embodiments, the at least one processor may be configured to store in memory at least one unique water usage signature for each of the plurality of appliances. The at least one processor may be configured to receive, from the location in the distributed water. The at least one processor may be configured to determine from the current water usage measurements at least one current water usage signature. The at least one processor may be configured to compare the current water usage signature with at least one of the unique water usage signatures stored in memory to determine a match. The at least one processor may be configured to compare the current water usage signature with at least one of the unique water usage signatures stored in memory to determine a match by taking the unique water signatures and comparing them, algorithmically, to similar patterns. The at least one processor may be configured to ascertain an identifier of a water appliance in current use, based on the signature match. The at least one processor may be configured to ascertain an identifier that indicates a positive match based upon patterns and grouping of stored data with measured signals.

In some embodiments, the at least one water usage signature may include an initial spike, followed by a plateau. Regardless of the reason for the initial spike, in some embodiments an initial spike may be observed in the water flow rate when certain appliances are used. The magnitude of the spike may depend on characteristics unique to specific distributed water infrastructures, such as for example the distance of the measuring unit from the appliance in use, which may affect the magnitude of the spike. The magnitude of the spike may depend on characteristics specific to an appliance. For instance, the spike may depend on the amount of water consumed by the device.

In some embodiments, the at least one processor may be configured, based on an ascertained identifier of the water appliance in current use, to record, over time, aggregated usage information for the appliance. At least one processor may be configured to store operational information about the continued use of the water appliance in current use. Operational information may be any information that defines the appliance. By way of non-limiting example, operational information may include water flow, water usage, duration of consumption, time of consumption, and water patterns.

In some embodiments, it may be typical that water is consumed by multiple appliances at one time. This system may be able to distinguish and track the operation of individual appliances by storing unique water usage signatures for each appliance, and may also be able to distinguish between multiple water appliances used simultaneously. The at least one processor may be configured to extract the current water usage signature from current water usage measurements that reflect multiple water appliances used simultaneously. The at least one processor may be configured to distinguish multiple water appliances used simultaneously, by marking an indicator when a sustained increase in water flow is observed.

In some embodiments, the at least one processor may be configured to determine from the historical water usage measurements a plurality of unique water usage signatures for a single water appliance, where each water usage signature corresponds to a differing operating state of the single water appliance. The at least one processor may be configured to determine who may be using each device based on assignments of unique water usage signatures. A personal identifier might not associated with unique water usage signatures, but the unique water usage signatures may still be associated with an anonymous water consumer. The at least one processor may be configured to determine an identity of a water consumer before, after, or during the use of the device.

In some embodiments, the at least one processor may be configured to determine from the historical water usage measurements a plurality of unique water usage signatures for a single water appliance, where each water usage signature corresponds to the single water appliance operating substantially simultaneously with at least one other water appliance in the distributed water infrastructure. The substantially simultaneous operation may operate in rapid succession or within a certain time window, such as the non-limiting example of hands being washed after flushing a toilet.

In some embodiments, same model water appliances in the distributed water infrastructure may share similar signatures, where the at least one processor may be configured to use the similar signatures to aggregate water usage information by the model of the water appliance. The at least one processor may be configured to initiate a water preservation action based at least in part on the current usage signature, and in some embodiments, a water preservation action may be an action that can be automatic, semi-automatic, or a recommendation on how to use the appliance in a more efficient manner. The action may also be to notify the end-user of the imminent failure of the appliance. At least one processor may be configured to initiate a water preservation action using an identifier and stored operational information.

In some embodiments, the at least one processor may be configured to receive from a user, an identification of a water appliance in current use, and to associate in memory the identification with the current water usage signature. The at least one processor may be configured to determine an identity of water usage appliances by accessing signature information from an external source. The external source may include information provided by an appliance manufacturer. The external source may include a database of appliances and associated water usage signatures. The processor may be configured to store in memory information obtained from the external source. The water preservation action may include reporting, to an administrator, the identifier and water usage data.

In some embodiments, the water preservation action may include providing suggestions to a water administrator for reducing water consumption. Suggestions provided by the system may include suggestions to better use the appliance in an efficient cost-effective manner. Different water reduction strategies may be suggested based on the identified appliances used in the distributed water infrastructure.

In some embodiments, the water preservation action may include causing the display of a comparison of current water usage information with historical water use information for an appliance. The at least one processor may be configured to determine, based on the water usage signature of the appliance in current use, an abnormality in operation of the appliance in current use, and to send an alert on the abnormality. The identifier may include a type and brand of an appliance. The identifier may include at least one of a floor and room location of the water appliance in current use. The at least one processor may be configured to output cumulative water consumption data for each identified appliance in the distributed water infrastructure.

Figure 11:
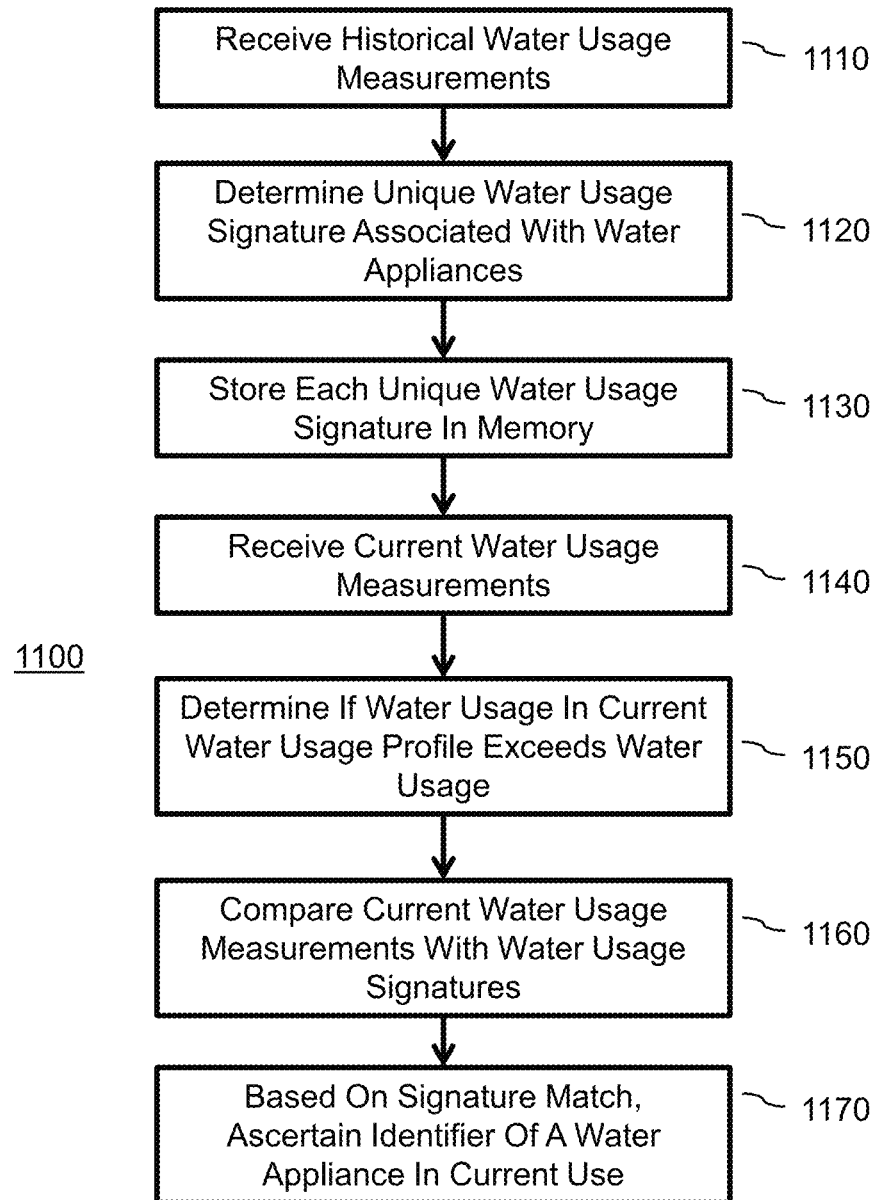
FIG. 11 illustrates an exemplary method for tracking usage of a plurality of water appliances in a distributed water infrastructure.

FIG. 11 illustrates an exemplary method 1100 for tracking usage of a plurality of water appliances in a distributed water infrastructure. The operations of method 1100 discussed herein are intended to be illustrative. In some embodiments, method 1100 may be implemented with one or more additional operations not described, and/or without one or more of the operations discussed. The order in which the operations of method 1100 are illustrated in FIG. 11 and described herein is not intended to be limiting. Additionally, the steps may be performed contemporaneously, or with some delay, with the measurement of water usage. The measurement of water usage may be performed by any one of the systems described herein. The measurement of water usage may be performed by separate components distributed by distance, and the operations may be performed immediately or at a later time via bath processing or delayed processing.

In some embodiments, method 1100 may be implemented in one or more processing devices. The one or more processing devices may include one or more devices executing some or all the operations of method 1100 in response to instructions stored electronically on an electronic storage medium. The one or more processing devices may include one or more devices configured through hardware, firmware, and/or software specifically designed for execution of one or more of the operations of method 1100.

In some embodiments, at operation 1110, at least one processor may be configured to receive, from a location in the distributed water infrastructure upstream of the plurality of water appliances, historical water usage measurements.

At operation 1120, at least one processor may be configured to determine from the historical water usage measurements at least one unique water usage signature associated with each of the plurality of water appliances. Water usage signatures may include an initial spike, followed by a plateau, as demonstrated in FIGS. 10*a-g*. At operation 1130, at least one processor may be configured to store in memory the unique water usage signature for each of the plurality of appliances.

In some embodiments, at operation 1140, at least one processor may be configured to receive, from the location in the distributed water infrastructure upstream of the plurality of water appliances, current water usage measurements. At operation 1150, at least one processor may be configured to determine from the current water usage measurements at least one current water usage signature. At operation 1160, at least one processor may be configured to compare the current water usage signature with at least one of the unique water usage signatures stored in memory to determine a match.

In some embodiments, at operation 1170, at least one processor may be configured to, based on the signature match, ascertain an identifier of a water appliance in current use. The match may be used to aggregate usage information for the appliance over time.

In some embodiments, the measurement of water usage may be performed by any one of the systems described herein, and/or the measure of water usage may be performed by a third-party water measuring device. The measurement of water usage may be performed by separate devices distributed by distance, where the processing operations may be performed locally or at a central location. The processing operations may be performed in real time, and/or at a later time. The processing operations may also be provided by distributed parallel or cloud computing infrastructures with data and results transported to the cloud or parallel processors using wireless or wired networks.

In accordance with the present disclosure, some of the embodiments described herein provide examples of the novel benefits of event-based leak detection systems and methods. A measurement of the number of liters consumed as a function of time may be transformed into a water usage pattern that has a particular fingerprint or water usage pattern. A water usage pattern may be determined by any method consistent with identification herein, such as the non-limiting examples of: event-based threshold method, guided machine learning, or automatic machine learning. Determining water usage pattern may be done with the assistance of a neural network, where a system may progressively improve performance to determine, identify, and compare water usage patterns by considering examples. In some embodiments, a neural network may be used without task-specific programming.

In various alternative methods, tracking usage of a plurality of water appliances in a distributed water infrastructure may be implemented by alternative methods of receiving water information, and employing event-based leak detection systems and methods to provide granularity of water usage to an end user.

Exemplary Embodiments of a Noise Generator used to Identify an Appliance

An aspect of some embodiments may include providing for noise generators to identify specific appliances. In order to aid in identifying water appliances, a potential benefit of some embodiments may include providing noise generators associated with specific water appliances. When the appliances are in use, each noise generator may send a unique noise signal to a receiver, which may identify the appliance in use. In this way, water usage measurements may be reliably associated with a particular appliance. An aspect of the disclosure may be directed to a system for tracking usage of a plurality of water appliances in a distributed water infrastructure, the system comprising at least one processor. At least one processor may be configured to receive, from a location in the distributed water infrastructure upstream of the plurality of water appliances, water usage information from one of the plurality of water appliances. At least one processor may be configured to receive a noise signal unique to the water appliance. At least one processor may be configured to correlate the water usage information of the water appliance with the unique noise signal of the appliance to identify water usage of the appliance.

In some embodiments, the noise signal may be generated via operation of the appliance. The noise signal may be generated by an aftermarket noise generator associated with the water appliance in the distributed water infrastructure.

Exemplary Embodiments of an All-In-One Learning Water Usage Tracking System

An aspect of some embodiments may include providing for all-in-one learning water usage tracking systems. A potential benefit of some embodiments may include offering a plug and play unit that incorporates flow and volume measurement, a communication module, a learning algorithm, and an electronic valve. With such an installation, a user may install a single device and track water usage throughout a distributed water system.

An aspect of some embodiments include a centralized system for tracking water usage of a plurality of water appliances in a distributed water infrastructure. The system an electronically controllable valve having an inlet for flow connection to a source of water and an outlet for flow connection to the distributed water infrastructure. The system may comprise a water flow sensor associated with the valve.

In some embodiments, the system may comprise a water volume sensor associated with the valve. The water volume sensor may be the same sensor as the water flow sensor. For example, a sensor capable of detecting the flow rate of water may also be able to integrate the flow rate over a period of time to determine the volume of water that has flowed past the sensor.

In some embodiments, the system may comprise a receiver, a transmitter, and at least one processor. The at least one processor may be configured to collect from the water flow sensor and the water volume sensor, flow and volume information relating to the upstream plurality of water appliances. The at least one processor may be configured to execute a learning algorithm to learn and log normal events in the distributed water infrastructure. The at least one processor may be configured to compare, in real time, current sensed events with learned normal events. The at least one processor may be configured to initiate remedial action if an event sensed in real time deviates from a learned normal event, where the remedial action may include sending a notification via the transmitter. The at least one processor may be configured to command to close the valve in response to a close valve instruction received via the receiver.

In some embodiments, the remedial action may include generating compliance data. The remedial action may include supplying the compliance data to an insurance company.

Exemplary Embodiments of Changing Zero Identifying Abnormal Consumption

Systems and methods of the present disclosure may provide the ability to learn normal system behavior and establish a baseline for overall system water usage when the water system is in a sleep state (nights and on weekends, for example). The system may track sleep state water usage over time, and if an upward trend is detected, signal a leak.

An aspect of some embodiments may include a system for changing the protection level for detection of abnormal consumption in a distributed water infrastructure by sensing the activity of the liquid infrastructure, the system comprising at least one processor. The processor may be configured to receive, from a liquid sensor upstream of a plurality of liquid appliances in the distributed liquid infrastructure, overall liquid consumption measurements. The processor may determine periods when the distributed liquid infrastructure is in an inactive state of substantial non-use of liquid appliances, track liquid consumption during a plurality of times when the distributed liquid infrastructure is in an inactive state, detect an upward trend in liquid consumption over the plurality of times, and initiate remedial action when the upward trend is detected.

In some embodiments, a high-sensitivity detector may be employed to differentiate between water usage and detect low level leaks. A change in the baseline during water use may indicate an abnormal water event. A rising flow rate during water use may indicate an abnormal water event.

In some embodiments, the remedial action may include generating an abnormal consumption alert. An increase in water consumption between sequential times of non-use may be insufficient to cause an initiation of remedial action.

Exemplary Embodiments of Aggregating Demographic Data with Water Meters

A potential benefit of some embodiments may include aggregating demographic data with water sensors. In some embodiments, systems and methods of the present disclosure may identify if a particular appliance is malfunctioning. As described above and below, water appliances may have their own water sensor for detecting malfunctions. Alternatively, a single sensor on the distributed water infrastructure may be able to determine, from water usage profiles, whether many water appliances are malfunctioning. If so, various forms of remedial action may be automatically taken. Systems may aggregate data from smart water sensors across many properties to identify trends in water usage by categories of appliances. Those trends may then be used for benchmarking purposes.

An aspect of some embodiments may include a system for determining operational states of specific categories of water appliances using a plurality of geographically distributed water sensors. In some embodiments, the system may comprise at least one processor. The system may comprise at least one central processor, which may aggregate data from multiple smart water sensors. The processor may perform processing steps in a distributed network.

In some embodiments, at least one processor may be configured to receive water appliance usage data from the plurality of geographically distributed water sensors, where each water sensor may be located upstream of a plurality of water appliances in an associated distributed water infrastructure. Each water sensor may be configured to collect data from an infrastructure inlet flow reflective of operation of at least one specific category of water appliance downstream of the water sensor. At least one processor may be configured to compare the water appliance usage data to determine trends in operation of the at least one specific category of water appliance across a population.

In some embodiments, at least one processor may be configured to output information about trends in usage data. The geographically distributed water sensors may be each associated with a differing household and may each include a transmitter for sending water appliance usage information for processing by the at least one central processor. The specific category of water appliance may include at least one category chosen from the group comprising washing machines, dishwashers, toilets, specific models of washing machines, specific models of dishwashers, and specific models of toilets, and the information about trends in usage may include at least one of malfunctions, efficiency, volume of water used, water flow rate, time of day of usage, location of usage, and cycles run in a specific time period. The at least one central processor may be configured to alert an administrator of a particular distributed water infrastructure if water usage for a category of appliance deviates substantially from a threshold. The at least one central processor may be configured to alert a water appliance manufacturer when a trend relating to malfunctions is detected.

In some embodiments, the geographically disbursed water sensors may be each associated with at least one local processor that may be configured to determine from collected data water usage, patterns sufficient to identify operation of specific appliances within an associated distributed water infrastructure. The local processor may transmit, for processing by the at least one central processor, information about the operation of the identified specific appliances. The collected data from the infrastructure inlet flow may include substantially all water flow through the infrastructure inlet, and the at least one central processor may be configured to determine geographical trends in home and away time periods based on the collected data. The specific appliances may include water faucets, shower heads, and toilets, where the at least one of local processor and the at least one central processor may be configured to determine home and away time from data reflective of at least one of water faucet usage, shower head usage, and toilet usage.

In some embodiments, the at least one local processor may be configured to receive, from at least one sensor associated with the distributed water infrastructure, signals indicative of water usage in the distributed water infrastructure and generate, from the signals indicative of water usage, at least one water usage signature. The local processor may compare the at least one water usage signature with at least one of the unique water usage signatures stored in memory to determine a match, based on the signature match, and ascertain an identifier of a specific water appliance corresponding to the water usage signature. The local processor may transmit, for processing by the at least one central processor, operational information about the specific water appliance.

An aspect of some embodiments may include methods for determining operational states of specific categories of water appliances using a plurality of geographically distributed water sensors. The method may comprise receiving water appliance usage data from the plurality of geographically distributed water sensors, where each water sensor may be located upstream of a plurality of water appliances in an associated distributed water infrastructure. Each water sensor may be configured to collect from an infrastructure inlet flow, via at least one local processor, data reflective on operation of at least one specific category of water appliance downstream of the water sensor. The method may comprise comparing, via at least one central processor, the water appliance usage data to determine trends on the operation of the at least one specific category of water appliance across a population.

In some embodiments, the method may comprise outputting information about usage trends. The method may comprise transmitting water appliance usage information from the geographically distributed water sensors, and receiving water appliance usage information via the at least one central processor. The geographically distributed water sensors may each be associated with a differing household and each geographically distributed water sensor may include a transmitter.

In some embodiments, the specific category of water appliance may include at least one category chosen from the group comprising washing machines, dishwashers, toilets, specific models of washing machines, specific models of dishwashers, and specific models of toilets, and the information about trends in usage may include at least one of malfunctions, efficiency, volume of water used, water flow rate, time of day of usage, location of usage, and cycles run in a specific time period. The method may comprise alerting an administrator of a particular distributed water infrastructure if water usage for a category of appliance deviates substantially from a threshold. The method may comprise alerting a water appliance manufacturer when a trend relating to malfunctions is detected.

In some embodiments, a method may comprise determining, via the at least one central processor, from collected data water usage, patterns sufficient to identify operation of specific appliances within an associated distributed water infrastructure, and transmitting information about the operation of the identified specific appliances. The method may comprise determining, via the at least one central processor, geographical trends in home and away time periods based on the collected data, where the collected data from the infrastructure inlet flow may include substantially all water flow through the infrastructure inlet. The method may comprise determining, via at least one of the at least one local processor and the at least one central processor, home and away time from data reflective of at least one of water faucet usage, shower head usage, and toilet usage.

In some embodiments, a method may comprise receiving, via at least one local processor, from at least one sensor associated with the distributed water infrastructure, signals indicative of water usage in the distributed water infrastructure. The method may comprise generating, via at least one local processor, from the signals indicative of water usage, at least one water usage signature, and comparing, via at least one local processor, the at least one water usage signature with at least one of the unique water usage signatures stored in memory to determine a match. Based on the signature match, the method may include ascertaining, via at least one local processor, an identifier of a specific water appliance corresponding to the water usage signature, and transmitting, via at least one local processor, for processing by the at least one central processor, operational information about the specific water appliance.

Figure 12A:
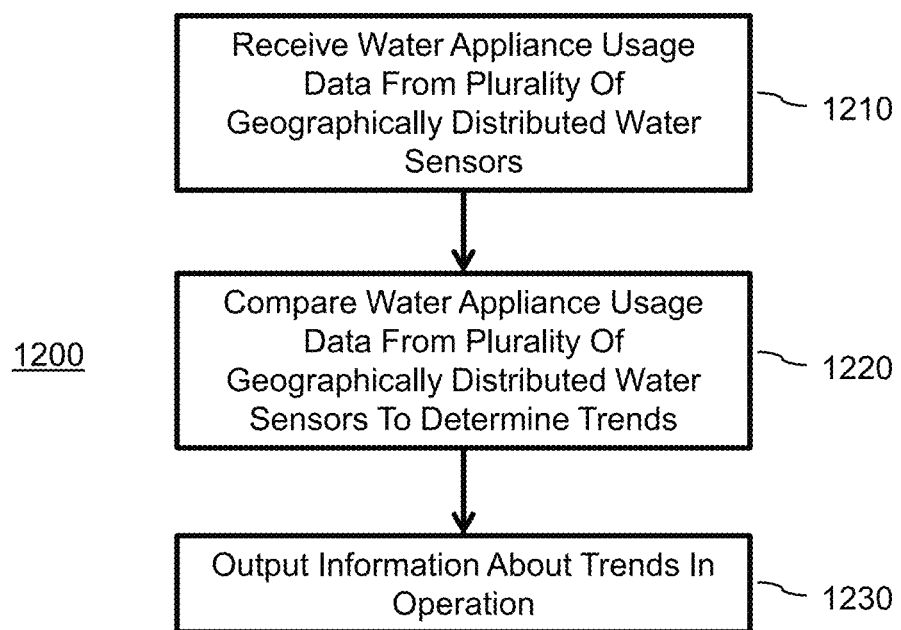
FIG. 12a illustrates an exemplary method for determining operational states of categories of water appliances using a plurality of geographically distributed water sensors.

FIG. 12a illustrates an exemplary method 1200 for determining operational states of specific categories of water appliances using a plurality of geographically distributed water sensors. The operations of method 1200 discussed herein are intended to be illustrative. In some embodiments, method 1200 may be implemented with one or more additional operations not described, and/or without one or more of the operations discussed. Additionally, the order in which the operations of method 1200 are illustrated in FIG. 12 and described herein is not intended to be limiting.

In some embodiments, at operation 1210, at least one processor may be configured to receive water appliance usage data from the plurality of geographically distributed water sensors, where each water sensor may be located upstream of a plurality of water appliances in an associated distributed water infrastructure. Each water sensor may be configured to collect data from an infrastructure inlet flow reflective on the operation of at least one specific category of water appliance downstream of the water sensor. At least one processor may be configured to collect data from an infrastructure inlet flow reflective of the operation of the at least one specific category of water usage.

In some embodiments, at operation 1220, at least one processor may be configured to compare the water appliance usage data from the plurality of geographically distributed water sensors to determine trends in operation of the at least one specific category of water appliance across a population. At operation 1230, at least one processor may be configured to output information about the trends in operation.

In some embodiments, method 1200 may be implemented in one or more processing devices. The one or more processing devices may include one or more devices executing some or all the operations of method 1200 in response to instructions stored electronically on an electronic storage medium. The one or more processing devices may include one or more devices configured through hardware, firmware, and/or software to be specifically designed for execution of one or more operations of method 1200.

Figure 12B:
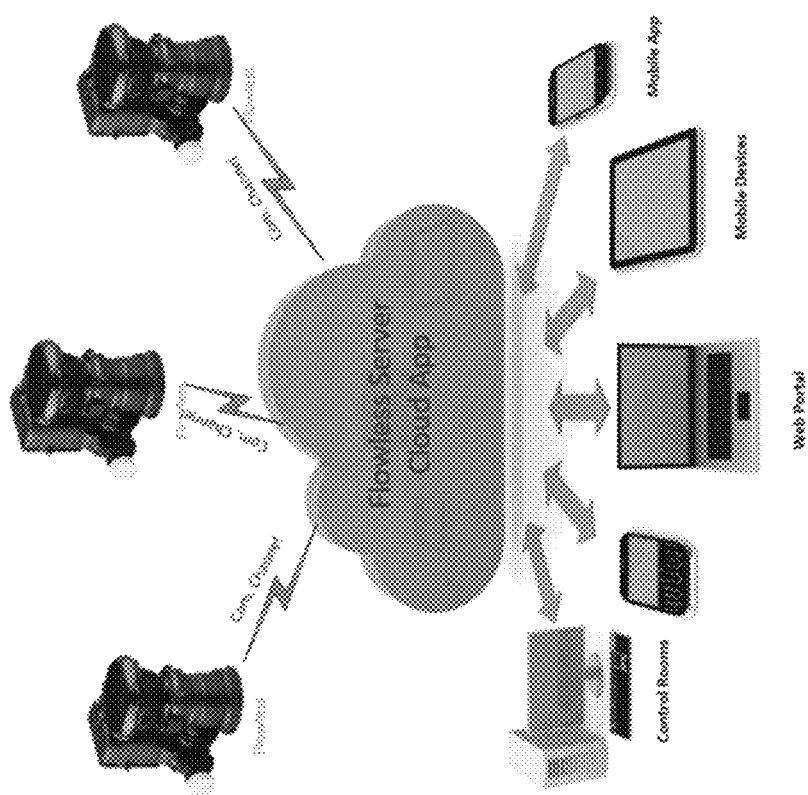
FIG. 12b illustrates an exemplary system for determining operational states of categories of water appliances using a plurality of geographically distributed water sensors.

FIG. 12b illustrates an exemplary system 1240 for determining operational states of specific categories of water appliances using a plurality of geographically distributed water sensors. In some embodiments, a sensor may be a "flowless" sensor configured as a flow sensor. FIG. 12b shows a plurality of sensors that communicate through a communication channel to a server. The plurality of sensors may be connected to the server with wired and/or wireless communication components. The server may be a server based in a cloud. The server may be accessed by a variety of devices including mobile devices and desktop computers.

In some embodiments, the measurement of water usage may be performed by any one of the systems described herein, and/or the measure of water usage may be performed by a third-party water measuring device. The measurement of water usage may be performed by separate devices distributed by distance, where the processing operations may be performed locally or at a central location. The processing operations may be performed in real time, and/or at a later time. The processing operations may also be provided by distributed parallel or cloud computing infrastructures with data and results transported to the cloud or parallel processor using wireless or wired networks.

In accordance with the present disclosure, some of the embodiments described herein provide examples of the novel benefits of event-based leak detection systems and methods. A measurement of the number of liters consumed as a function of time may be transformed into a water usage pattern that has a particular fingerprint or water usage pattern. A water usage pattern may be determined by any method consistent with identification herein, such as the non-limiting examples of: event-based threshold method, guided machine learning, or automatic machine learning. Determining water usage patterns may be assisted using a neural network, where a system may progressively improve performance to determine, identify, and compare water usage patterns by considering examples. A neural network may be used without task-specific programming.

In various alternative embodiments, determining operational states of specific categories of water appliances using a plurality of geographically distributed water sensors may be implemented using methods for receiving water information and employing event-based leak detection systems and methods to provide granularity of water usage to an end user.

Exemplary Embodiments of Water Profiles to Detect Malfunctioning Water Appliances An aspect of some embodiments may include a system for determining, from a location upstream of a plurality of water appliances, whether a specific water appliance may be malfunctioning. A location upstream may be any point in the distributed water infrastructure before the point where a water consumer is located. A location downstream may be any location in the distributed water infrastructure after the point where a sensing device is located. The information gathered from this location may be used in processes to determine the consumption of water passing through. The information gathered from this location may indicate that a specific water appliance is malfunctioning. A specific water appliance malfunction may an appliance that is broken and/or working outside of correct specifications. A specific water appliance malfunction may not necessarily mean that a water appliance shows a current problem, rather, it may mean a problem may be imminent.

In some embodiments, a system according to the present disclosure may include at least one processor. At least one processor may be configured to detect, from at least one sensor in a distributed water infrastructure upstream of the plurality of water appliances, a plurality of normal water usage profiles. Normal water usage profiles may be patterns that are gathered over time showing the normal usage of a water appliance. Normal water usage of an appliance may include any information that represents the proper working of the appliance. Information that represents a proper working of an appliance may be appliance specific and the information may include a normal water usage profile.

In some embodiments, at least one processor may be configured to associate at least one of the plurality of normal water usage profiles with each of the plurality of water appliances. The at least one processor may be configured to store each of the plurality of normal water usage profiles in a manner that associates each of the plurality of normal water usage profiles with its corresponding water appliance. At least one processor may be configured to detect at least one current water usage profile. The at least one processor may be configured to detect a profile by continually comparing measured current water usage profiles against a stored database of normal water usage profiles. Current water usage profiles may be generated in a like manner to normal water usage profiles except that they are temporary.

In some embodiments, at least one processor may be configured to compare the at least one current water usage profile with at least one of the stored normal water usage profiles to determine a corresponding identity of an associated water usage appliance and to determine if a substantial deviation exists between the stored normal water usage profile for the identified appliance and the at least one current water usage profile. The substantial deviation may be reflective of a potential malfunction in the associated water usage appliance.

Determining a corresponding identity refers to the process of matching a water appliance against a set of stored patterns and characteristics that identify a particular water appliance. An associated water usage appliance may be any similar water appliance stored in a data retrieval system that has a specific set of characteristics that can be used to help identify the matching water system. A substantial deviation may be any deviation from what an appliance with a specific water usage profile is expected to be and what the system may be seeing currently. Based upon a magnitude of this difference (deviation), the difference might mean that the water appliance is not working properly.

In some embodiments, at least one processor may be configured to initiate remedial action if the substantial deviation, reflective of a potential malfunction, is determined. Initiating remedial action may be anything from a self-test to a service call or probe by other sensing systems. A service call may be an actual repair or preventative action. A recommendation to purchase a new appliance may include times when the system determines that based upon the deviation, the best and cheapest course of action would be to purchase a new appliance. If this is the case, the system may inform why this decision was made and may suggest appropriate models to buy. Such a recommendation may be based on the specific water appliance.

In some embodiments, the at least one processor may be configured to receive aggregate signals reflective of simultaneous operation of multiple water appliances and to extract from the aggregate signals normal water usage profiles for specific appliances. In one embodiment, this may be part of a system for determining, from a location upstream of a plurality of water appliances, whether a specific water appliance is malfunctioning. The system may comprise at least one processor configured to: detect, from the at least one sensor in a distributed water infrastructure upstream of the plurality of water appliances, a plurality of normal water usage profiles, associate each normal water usage profile with a specific water usage appliance, and store each normal water usage profile for each specific water usage appliance. The system may detect at least one current water usage profile, compare the at least one current water usage profile with at least one of the stored normal water usage profiles to determine a corresponding identity of an associated water usage appliance and to determine if a substantial deviation exists between the normal water usage profile for the identified appliance and the current water usage profile. The system may initiate remedial action if the substantial deviation exists.

In some embodiments, at least one processor may be configured to determine water usage spikes in the aggregate signals, and to identify an initiation of use of a water appliance based on a determined water usage spike. The identified appliance may include a water pump, where the substantial deviation is reflective of a pump malfunction. The at least one processor may be configured to detect a pump malfunction before a failure, where the remedial action may include transmitting a message indicating an expected failure. The identified appliance may be a toilet where the substantial deviation is reflective of a toilet valve leak.

In some embodiments, the at least one processor may be configured to receive from a user an indication of an appliance location in the distributed water infrastructure, and to store the location in a manner associating the location with the corresponding water appliance. A remedial action may be initiated if the at least one processor determines that the current water usage profile indicates a flow rate of greater than 50-100 ml in less than 0.18 seconds. The at least one processor may be configured to determine the corresponding identity of a water appliance based on at least one of initial rise in flow rate, average sustained flow rate, noise in a flow rate, and duration of water consumption.

In some embodiments, the identified appliance may be determined to be malfunctioning based on at least one characteristic not used to identify the water appliance. The at least one processor may be configured to identify a malfunction based on a change in acoustic noise in the at least one current water usage profile.

In some embodiments, a remedial action may include providing information about the malfunction for transmission to a manufacturer of an appliance determined to be malfunctioning. The remedial action may include sending a notification to initiate a service call. The at least one processor may be configured to provide an estimate of at least one of wasted water and cost for continuing to operate a faulty device. The at least one processor may be configured to output for display, analytics on the identified appliance, where the analytics may be based on historical data captured over time for the identified appliance. At least one processor may be configured to output to a display a visual comparison of current usage of an appliance and normal appliance usage. The remedial action may include providing a recommendation to purchase a new appliance.

In some embodiments, determining if a substantial deviation exists may include accessing a database of profiles of malfunctions, and determining that a match exists between the current water usage profile and one or more profiles of malfunctions.

An aspect of some embodiments may include systems for determining, from a location upstream of a plurality of water appliances, whether a specific water appliance is malfunctioning. The system may comprise memory for storing at least one preloaded characteristic associated with normal operation of the specific water appliance. The system may comprise at least one processor, which may be configured to detect at least one current water usage profile associated with the specific water appliance. At least one processor may be configured to compare the at least one current water usage profile with at least one preloaded characteristic to determine if the at least one current water usage profile is reflective of a malfunction. At least one processor may be configured to initiate remedial action if the at least one current water usage profile is reflective of a malfunction.

In some embodiments, the at least one current water usage profile may include a plurality of overlapping normal water usage profiles, and the at least one processor may be configured to segregate, from the plurality of overlapping normal water usage profiles, the at least one current water usage profile associated with the specific water appliance.

Figure 13:
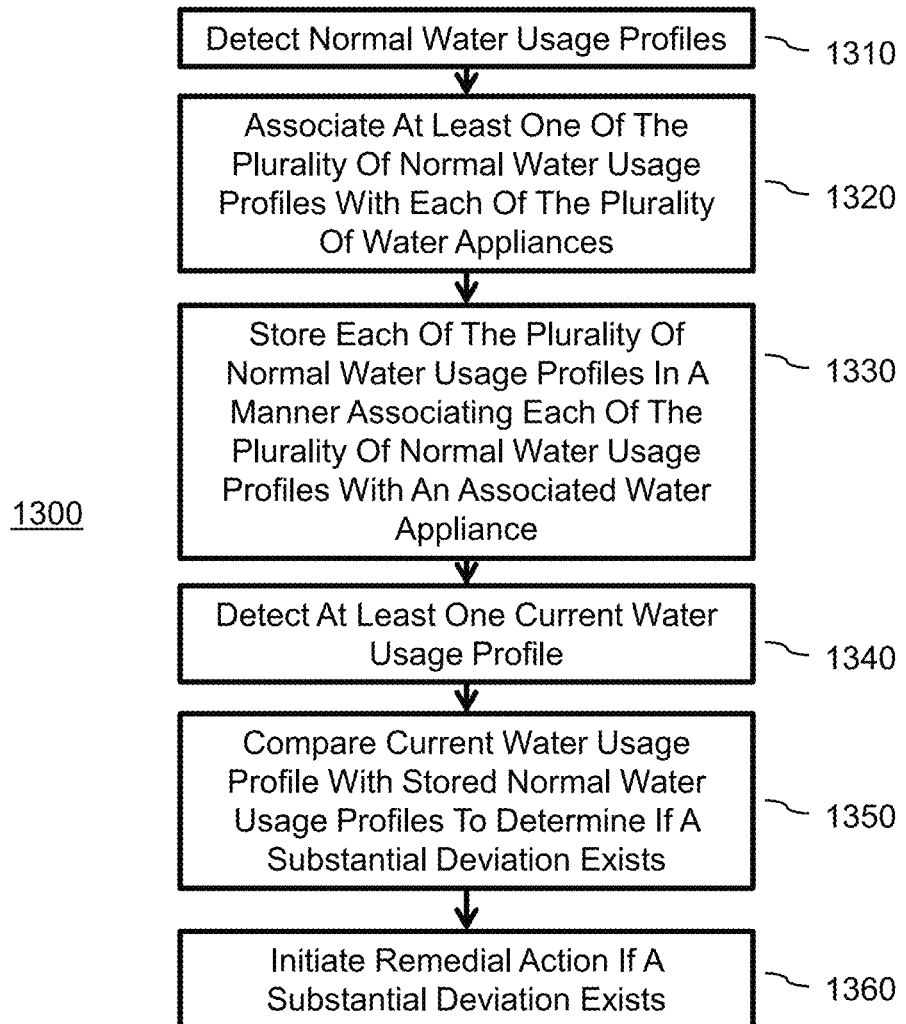
FIG. 13 illustrates an exemplary method for determining, from a location upstream of a plurality of water appliances, whether a specific water appliance may be malfunctioning.

FIG. 13 illustrates an exemplary method 1300 for determining, from a location upstream of a plurality of water appliances, whether a specific water appliance may be malfunctioning. The operations of method 1300 discussed herein are intended to be illustrative. In some embodiments, method 1300 may be implemented with one or more additional operations not described, and/or without one or more of the operations discussed. Additionally, the order in which the operations of method 1300 are illustrated in FIG. 13 and described herein is not intended to be limiting.

In some embodiments, method 1300 may be implemented in one or more processing devices. The one or more processing devices may include one or more devices executing some or all the operations of method 1300 in response to instructions stored electronically on an electronic storage medium. The one or more processing devices may include one or more devices configured through hardware, firmware, and/or software specifically designed for execution of one or more of the operations of method 1300.

In some embodiments, at operation 1310, at least one processor may be configured to detect, from at least one sensor in a distributed water infrastructure upstream of the plurality of water appliances, a plurality of normal water usage profiles. At operation 1320, at least one processor may be configured to associate at least one of the plurality of normal water usage profiles with each of the plurality of water appliances. At operation 1330, at least one processor may be configured to store each of the plurality of normal water usage profiles in a manner associating each of the plurality of normal water usage profiles with an associated water appliance. At operation 1340, at least one processor may be configured to detect at least one current water usage profile.

In some embodiments, at operation 1350, at least one processor may be configured to compare the at least one current water usage profile with at least one of the stored normal water usage profiles to determine a corresponding identity of an associated water usage appliance and to determine if a substantial deviation exists between the stored normal water usage profile for the identified appliance and the at least one current water usage profile, where the substantial deviation may be reflective of a potential malfunction in the associated water usage appliance. At least one processor may be configured to determine the corresponding identity of a water appliance based on at least one of initial rise in flow rate, average sustained flow rate, noise in a flow rate, and a duration of water consumption In some embodiments, determining may refer to a process of matching a water appliance against a set of stored patterns and characteristics that identify the particular water appliance. In some embodiments, matching may be performed by a machine learning algorithm. The matching may be performed automatically, after the at least one processor has been provided a training set. At operation 1360, at least one processor may be configured to initiate remedial action if the substantial deviation, reflective of a potential malfunction, is determined.

In some embodiments, the measurement of water usage may be performed by any one of the systems described herein, and/or the measure of water usage may be performed by a third-party water measuring device. The measurement of water usage may be performed by separate devices distributed by distance, where the processing operations may be performed locally or at a central location. The processing operations may be performed in real time, and/or at a later time. The processing operations may also be provided by distributed parallel or cloud computing infrastructures with data and results transported to the cloud or parallel processor using wireless or wired networks.

In accordance with the present disclosure, some of the embodiments described herein provide examples of the novel benefits of event-based leak detection systems and methods. A measurement of the number of liters consumed as a function of time may be transformed into a water usage pattern that has a particular fingerprint or water usage pattern. A water usage pattern may be determined by any method consistent with identification herein, such as the non-limiting examples of: event-based threshold method, guided machine learning, or automatic machine learning.

Water usage pattern determination may be assisted by a neural network, where a system may progressively improve performance to determine, identify, and compare water usage patterns by considering examples. A neural network may be used without task-specific programming.

In various alternative methods, determining, from a location upstream of a plurality of water appliances, whether a specific water appliance may be malfunctioning may be implemented by alternative processes for receiving water information, and employing event-based leak detection systems and methods to provide granularity of water usage to an end user.

Exemplary Embodiments of Graphical Interfaces Enabling Category Comparison of Water Usage Over Time An aspect of some embodiments may provide for a graphical user interface (GUI) for enabling category comparison of water usage over time. While water users are able to compare their water bills from month to month to track overall water usage, a potential benefit of some embodiments may be that systems and methods of the present disclosure may compare water usage across time periods on a category basis (e.g., irrigation, cooling tower, water appliances, etc.). Such a benefit can provide greater granular detail on how consumers are using their water, and provide insight on how to reduce consumption. A potential benefit of some embodiments of the present disclosure may include transforming signals into a display output in a readily readable way.

An aspect of some embodiments may include a system for tracking, in a distributed water infrastructure, water usage by category. Tracking a distributed water system may include the process of identifying the characteristic consumption of all of the water consumed in a distributed water infrastructure in real-time or in near-real-time. Characteristic consumption may include a particular water-consuming appliance or device working automatically, being used in a standard way by an individual, or being used to perform a particular task by an individual in a way that may be unique to that individual. The tracking process may also include monitoring volume, flow rate, duration, and other quantitative features of water consumption based on these, to provide a detailed view of the nature of the water consumption.

In some embodiments, the system may comprise at least one processor. At least one processor may be configured to receive from at least one sensor associated with the distributed water infrastructure signals indicative of water usage in the distributed water infrastructure.

In some embodiments, at least one processor may be configured to receive, from at least one sensor associated with the distributed water infrastructure, signals indicative of water usage in the distributed water infrastructure. The processor may be configured to construct, based on the signals indicative of water usage, a plurality of profiles. Constructing a plurality of profiles may include the process of segmenting the signals indicative of water usage into groups of signals, each of which represents a particular use of a particular water-consuming device or appliance that may be connected to the distributed water infrastructure, where each of these groups of signals may be a water event profile. These profiles may be extracted by means of an automatic, semi-automatic, or manual segmentation algorithm.

In some embodiments, at least one processor may be configured to assign each profile to one of a plurality of water usage categories. At least one processor may be configured to collect from the at least one sensor, signals indicative of water usage for substantially all water delivered through the distributed water infrastructure in a time period. At least one processor may be configured to construct a plurality of water usage profiles, in the aggregate encompassing substantially all water delivered through the distributed water infrastructure in the time period. Substantially all water delivered refers to the sensor being able to sense a sufficient amount of water consumption in some distributed water infrastructure so that the water consumption tracking may be performed to substantial completion on all of the water passing through the distributed water infrastructure.

In some embodiments, at least one processor may be configured to assign each constructed water usage profile to one of the plurality of water usage categories. Assigning may include the process of mapping each of the water event profiles extracted from the water consumption signal to one or only one of the categories of water usage that has been identified for the distributed water infrastructure. The mapping process may be automatic, semi-automatic, or manual. An automatic or semi-automatic mapping process may include using a mathematical model based on a supervised or semi-supervised machine learning algorithm that is applied to the extracted profiles to categorize them.

In some embodiments, at least one processor may be configured to output, for display, water usage for the time period, for each of the plurality of water usage categories. The at least one processor may be configured to display to an administrator, in graphical form, comparative information over time for a specific category. Graphical forms may include using appropriate graphs to present the extracted data for each category of water consumption so that it is clear and informative. This may include collective graphical presentation of all the time-based signals for each profile for a category of water consumption. Comparative information may include the graphical presentation of each of the categories of water consumption in such a way that it illustrates the changes in water usage for that particular water consumption category over some period of time and allows the user to compare the consumption for that category from different time periods.

In some embodiments, the plurality of water usage categories may include at least one of toilets, sinks, urinals, showers, washing machines, dishwashers, ice makers, irrigation, subcategories of processing machines, and uncategorized water usage. The plurality of water usage categories each may include an identity of an individual. The signals indicative of water usage may be sufficiently granular so as to capture water usage patterns that tend to be unique to particular individuals, where each water usage pattern associated with a particular individual may be assigned to separate categories for the particular individual.

In some embodiments, the at least one processor may be configured to output, for display to an administrator in graphical form, comparative water usage information between categories. The at least one processor may be configured to identify consumption by a particular type of water-consuming appliance in a distributed water infrastructure in real-time, and to assign to separate types of categories water usage information associated with the particular type of water-consuming appliance. The at least one processor may be configured to track at least one of the volume, flow rate, and duration of water consumption, by category. The plurality of water usage profiles may be extracted from the signals indicative of water usage using a segmentation algorithm. The at least one sensor may include a flow meter having a resolution of at least 0.2 liters per hour.

In some embodiments, the processor may be configured to receive a request for a report of water usage for at least one category during a sub-time period less than the duration of the time period, where the at least one processor may be configured to output water usage information for the sub-time period.

An aspect of some embodiments may include computer-implemented methods for monitoring water usage in a distributed water infrastructure. In some embodiments, the method may comprise tracking historical water usage information using at least one sensor upstream of a plurality of water appliances in the distributed water infrastructure. The method may comprise determining from the historical water usage information received by the at least one sensor, a plurality of normal water profiles for each of the plurality of water appliances in the distributed water infrastructure. The method may comprise categorizing the plurality of normal water profiles into at least one of two categories, including water appliance type and individual users, and outputting, for display by category, water usage information In some embodiments, the method may comprise outputting information displaying an amount of water usage for at least one category of water usage. Outputting may include providing graphical information for displaying an amount of water usage over time. Outputting by at least one category may include providing aggregated information about all water used by a particular individual within a time period. Outputting by at least one category may include providing aggregated information about all water used by a particular category of water appliance within a time period.

In some embodiments, a method may further comprise the steps of receiving current water usage information from the at least one sensor, determining a current water profile, categorizing the current water profile into at least one category of water usage, and outputting data for generating a categorized report of a current total amount of water consumed. The method may further comprise the step of displaying a trend in water usage for at least one water usage category.

In some embodiments, the method may further comprise the step of providing an estimate for water usage for at least one water usage category. The plurality of water usage categories may include at least one of toilets, sinks, urinals, showers, washing machines, dishwashers, ice makers, irrigation, subcategories of processing machines, and uncategorized water usage. The plurality of water usage categories may each include an identity of an individual.

Figure 14:
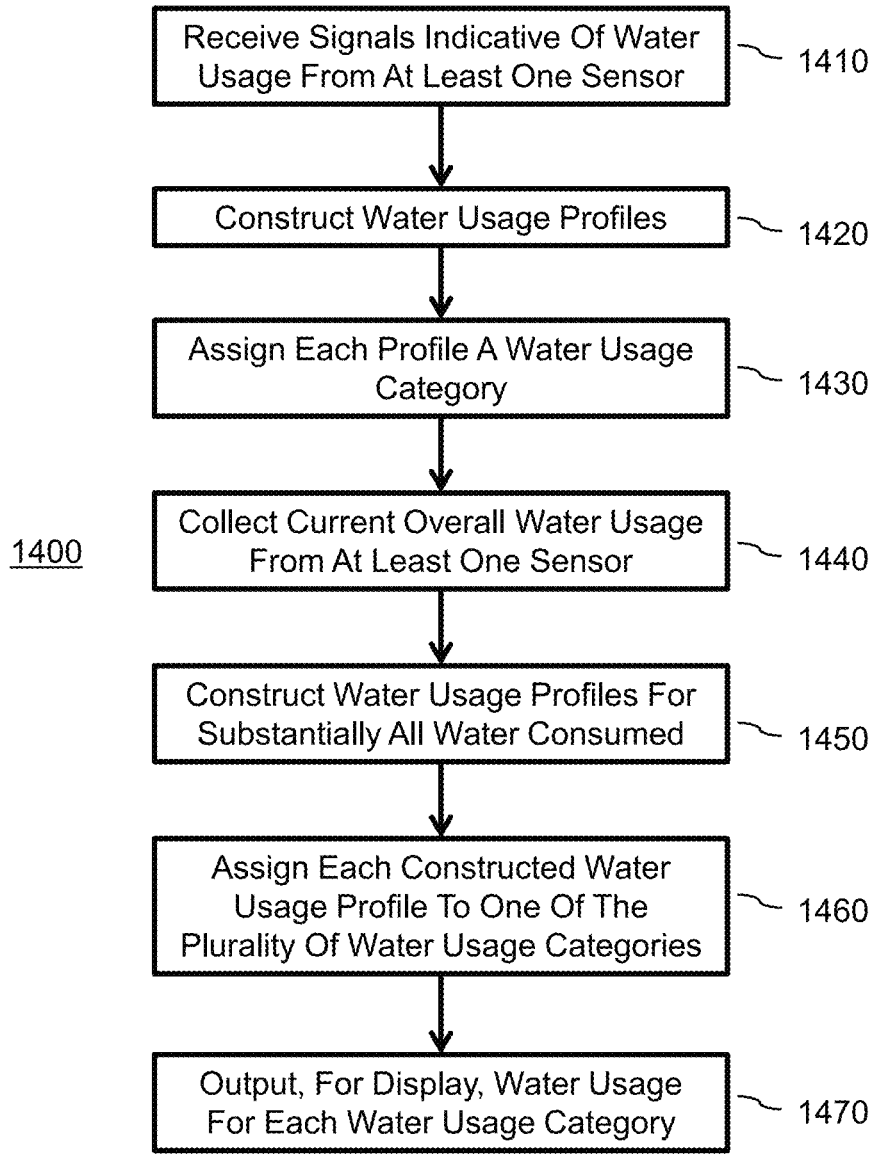
FIG. 14 illustrates an exemplary method for tracking, in a distributed water infrastructure, water usage by category.

FIG. 14 illustrates an exemplary method 1400 for tracking, in a distributed water infrastructure, water usage by category. The operations of method 1400 discussed herein are intended to be illustrative. In some embodiments, method 1400 may be implemented with one or more additional operations not described, and/or without one or more of the operations discussed. Additionally, the order in which the operations of method 1400 are illustrated in FIG. 14 and described herein is not intended to be limiting.

In some embodiments, method 1400 may be implemented in one or more processing devices. The one or more processing devices may include one or more devices executing some or all the operations of method 1400 in response to instructions stored electronically on an electronic storage medium. The one or more processing devices may include one or more devices configured through hardware, firmware, and/or software to be specifically designed for execution of one or more of the operations of method 1400.

In some embodiments, at operation 1410, at least one processor may be configured to receive, from at least one sensor associated with the distributed water infrastructure, signals indicative of water usage in the distributed water infrastructure. At operation 1420, at least one processor may be configured to, based on the signals indicative of water usage, construct a plurality of profiles. At operation 1430, at least one processor may be configured to assign each profile to one of a plurality of water usage categories. At operation 1440, at least one processor may be configured to collect, from the at least one sensor, signals indicative of water usage for substantially all water delivered through the distributed water infrastructure in a time period. At operation 1450, at least one processor may be configured to construct a plurality of water usage profiles, which may in the aggregate encompass substantially all water delivered through the distributed water infrastructure in the time period. At operation 1460, at least one processor may be configured to assign each constructed water usage profile to one of the plurality of water usage categories.

In some embodiments, at operation 1470, at least one processor may be configured to output, for display, water usage for the time period, for each of the plurality of water usage categories. The measurement of water usage may be performed by any one of the systems described herein, and/or the measure of water usage may be performed by a third-party water measuring device. The measurement of water usage may be performed by separate devices distributed by distance, where the processing operations may be performed locally or at a central location. The processing operations may be performed in real time, and/or at a later time. The processing operations may also be provided by distributed parallel or cloud computing infrastructures with data and results transported to the cloud or parallel processor using wireless or wired networks.

In accordance with the present disclosure, some of the embodiments described herein provide examples of the novel benefits of event-based leak detection systems and methods. In some embodiments, measurement of the number of liters consumed as a function of time may be transformed into a water usage pattern that has a particular fingerprint or water usage pattern. A water usage pattern may be determined by any method consistent with identification herein, such as the non-limiting examples of: event-based threshold method, guided machine learning, or automatic machine learning. Water usage pattern determination may be assisted by a neural network, where a system may progressively improve performance to determine, identify, and compare water usage patterns by considering examples. A neural network may be used without task-specific programming.

In various alternative methods, tracking water usage by category may be implemented by alternative methods of receiving water information, and employing event-based leak detection systems and methods to provide granularity of water usage to an end user.

Exemplary Embodiments of Differentiating between Individuals

An aspect of some embodiments may include developing systems and methods to differentiate between particular water appliances being used. Aspects of the present disclosure may also enable differentiation between users of the appliances, based on specific water usage behavior of the users. This, for example, may allow the system to identify who in a home takes the longest showers or leaves the bathroom sink running the longest.

An aspect of some embodiments may include systems for differentiating between water usage of multiple water consumers using a common distributed water infrastructure. In some embodiments, the system may comprise at least one processor. The at least one processor may be configured to receive, from a water sensor in the distributed water infrastructure upstream of a plurality of appliances, signals indicative of water usage.

In some embodiments, at least one processor may be configured to construct from the signals indicative of water usage a plurality of water event profile signatures. At least one processor may be configured to, based on differences between similar water event profiles, associate at least one water event profile signature with a first water consumer and associate a second water event profile signature with a second water consumer. Differences between similar water event profiles may refer to a delta that can be discerned between similar water events. These differences may be analyzed and stored. The process of learning these differences may use algorithms that learn from and make predictions based on the data available (e.g., genetic algorithms and random decision forest algorithms).

In some embodiments, at least one processor may be configured to store the water event profile signatures for the first water consumer and the second water consumer. The process of constructing ongoing water event profiles may refer to when a system according to an embodiment of the present invention creates baseline water event profiles and analyzes a water event. A water event profile may be refined successively over time and with more data.

In some embodiments, at least one processor may be configured to construct current water event profiles reflecting subsequent water usage in the distributed water infrastructure. At least one processor may be configured to compare the current water event profiles with water event profile signatures stored in memory. At least one processor may be configured to, based on the comparison, attribute a first current water event profile to the first water consumer and attribute a second current water event profile to the second water consumer.

At least one processor may output data for generating at least one report of water usage by the first water consumer. A report may be any information that is transmitted, regardless of means of transmission, to another party or parties informing them of a water event and/or water usage. A report may also include detailed water event profile information.

In some embodiments, at least one processor may be further configured to associate at least one water event profile with at least one appliance, where the output data segregates water usage of the at least one appliance by the first water consumer. The at least one processor may be configured to update the water event profile signatures using the current water event profiles. Each water event profile signature may have a form substantially similar to a form of a water event profile. Each water event profile signature may reflect characteristics of a corresponding water event profile.

In some embodiments, the at least one processor may be configured to receive an input on the identity of the first water consumer, and to store in memory, in association with a first water event profile signature, the identity of the first water consumer. The at least one processor may be configured to recognize the first water consumer from the second water consumer based on distinct usage patterns within an associated current water event profile. Each water usage profile signature may take into account at least one of duration of water usage, time of water usage, volume of water usage, and rate of water usage.

In some embodiments, each water usage profile signature may take into account at least two of a duration of water usage, a time of water usage, a volume of water usage, and a rate of water usage. In some embodiments, a system may further comprise associating a first group of the plurality of water event profile signatures with the first water consumer and associating a second group of the plurality of water event profile signatures with the second water consumer, where at least some of the first group of the plurality of water event profile signatures may be each associated with differing water appliances.

In some embodiments, the differing water appliances may include at least one faucet, where the at least one processor may be configured to use the water event profile signatures to distinguish between usage of the at least one faucet by the first water consumer and the second water consumer. The at least one processor may be configured to permit a water event profile signature to be assigned to an individual through a user input. The at least one processor may be configured to permit a water event profile to be assigned to an individual through a learning algorithm. The at least one processor may be configured to receive training data on a typical consumer to improve identification of a first water consumer.

At least one report of water usage may include an amount of water a specific individual consumed using specific appliances. The at least one processor may be configured to send a notification to an end user requesting user input on water consumption not associated with particular water consumers. The at least one processor may be configured to estimate when particular water consumers may be away for a period of time, by comparing current water usage profiles with water usage profile signatures, and noting that, during the period of time, current water usage profiles do not correspond to any water usage profile signatures.

In some embodiments, the at least one processor may be configured to initiate a remedial action if a current water event profile associated with the first water consumer substantially deviates from an associated water event profile signature for the first water consumer. The liquid consumer may be a specific individual. The liquid consumer may be a specific appliance. In some embodiments, the water consumer may be a type of appliance.

The at least one processor may be configured to permit a water event profile to be assigned to an individual through a user input. The at least one processor may be configured to permit a water event profile to be assigned to an unidentified individual through a learning algorithm.

An aspect of some embodiments may include methods for differentiating between water usage of multiple water consumers using a common distributed water infrastructure. The method may comprise receiving from a water sensor, associated with the distributed water infrastructure and upstream of a plurality of appliances, signals indicative of water usage.

In some embodiments, the method may comprise constructing from the signals indicative of water usage a plurality of water event profile signatures. The method may comprise associating at least one water event profile signature with a first water consumer and associating a second water event profile signature with a second water consumer. The method may comprise storing the water event profile signatures for the first water consumer and the second water consumer. The method may comprise constructing current water event profiles reflecting subsequent water usage in the distributed water infrastructure, and comparing the current water event profiles with water event profile signatures stored in memory. The method may comprise, based on the comparison, attributing a first current water event profile with the first water consumer and attributing a second current water event profile to the second water consumer.

In some embodiments, the method may comprise outputting data for generating at least one report of water usage by the first water consumer. The method may further comprise updating the water event profile signatures using the current water event profiles.

Figure 15:
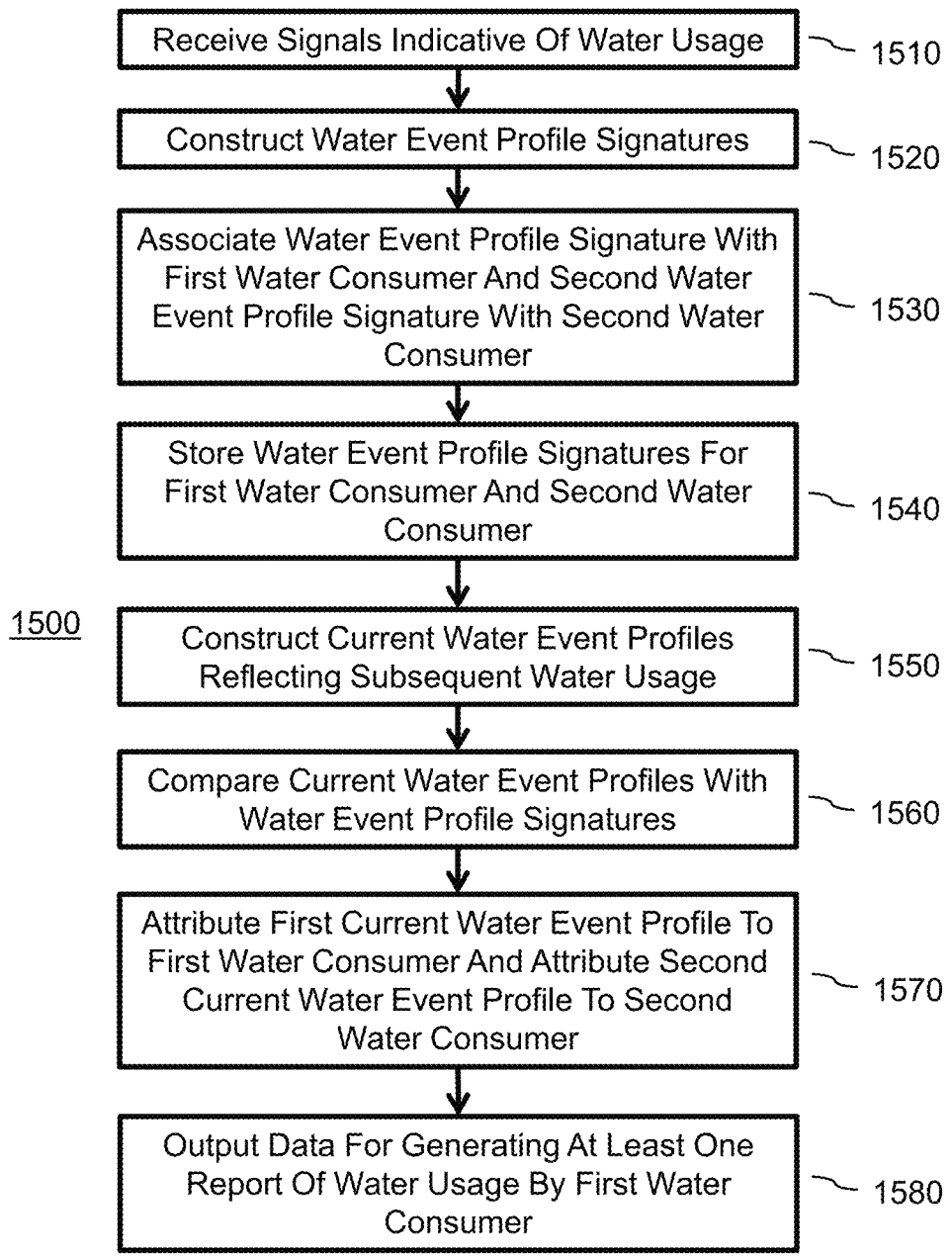
FIG. 15 illustrates an exemplary method for differentiating between water usage of multiple water consumers using a common distributed water infrastructure.

FIG. 15 illustrates an exemplary method 1500 for differentiating between water usage of multiple water consumers using a common distributed water infrastructure. The operations of method 1500 discussed herein are intended to be illustrative. In some embodiments, method 1500 may be implemented with one or more additional operations not described, and/or without one or more of the operations discussed. Additionally, the order in which the operations of method 1500 are illustrated in FIG. 15 and described herein is not intended to be limiting.

In some embodiments, method 1500 may be implemented in one or more processing devices. The one or more processing devices may include one or more devices executing some or all the operations of method 1500 in response to instructions stored electronically on an electronic storage medium. The one or more processing devices may include one or more devices configured through hardware, firmware, and/or software to be specifically designed for execution of one or more of the operations of method 1500.

In some embodiments, at operation 1510, at least one processor may be configured to receive, from a water sensor in the distributed water infrastructure upstream of a plurality of appliances, signals indicative of water usage. At operation 1520, at least one processor may be configured to construct, from the signals indicative of water usage, a plurality of water event profile signatures. At operation 1530, at least one processor may be configured to, based on differences between similar water event profiles, associate at least one water event profile signature with a first water consumer and associate a second water event profile signature with a second water consumer. At operation 1540, at least one processor may be configured to store the water event profile signatures for the first water consumer and the second water consumer. At operation 1550, at least one processor may be configured to construct current water event profiles reflecting subsequent water usage in the distributed water infrastructure. At operation 1560, at least one processor may be configured to compare the current water event profiles with water event profile signatures stored in memory. At operation 1570, at least one processor may be configured to, based on the comparison, attribute a first current water event profile to the first water consumer and attribute a second current water event profile to the second water consumer. At operation 1580, at least one processor may be configured to output data for generating at least one report of water usage by the first water consumer.

In some embodiments, the measurement of water usage may be performed by any one of the systems described herein, and/or the measure of water usage may be performed by a third-party water measuring device. The measurement of water usage may be performed by separate devices distributed by distance, where the processing operations may be performed locally or at a central location. The processing operations may be performed in real time, and/or at a later time. The processing operations may also be provided by distributed parallel or cloud computing infrastructures with data and results transported to the cloud or parallel processor using wireless or wired networks.

In accordance with the present disclosure, some of the embodiments described herein provide examples of the novel benefits of event-based leak detection systems and methods. A measurement of the number of liters consumed as a function of time may be transformed into a water usage pattern that has a particular fingerprint or water usage pattern. A water usage pattern may be determined by any method consistent with identification herein, such as the non-limiting examples of: event-based threshold method, guided machine learning, or automatic machine learning. Water usage pattern determination may be assisted by a neural network, where a system may progressively improve performance to determine, identify, and compare water usage patterns by considering examples. A neural network may be used without task-specific programming.

In various alternative methods, differentiating between water usage of multiple water consumers using a common distributed water infrastructure may be implemented by alternative methods of receiving water information, and employing event-based leak detection systems and methods to provide granularity of water usage to an end user.

Exemplary Embodiments of a Time-Based System for Detecting Water Usage Abnormalities Aspects of some embodiments may provide for time-based schemes for detecting water usage abnormalities. In some embodiments, remedial actions may vary depending on time of day or day of week. That is, since water usage profiles may vary depending on time and day, normal activity may necessarily vary over time. By taking these variations into account, a potential benefit of some embodiments may be greater accuracy.

An aspect of some embodiments may include a system for detecting abnormal liquid usage over time in a distributed liquid infrastructure, the system comprising at least one processor. At least one processor may be configured to receive, from at least one sensor associated with the distributed liquid infrastructure, signals indicative of water usage. At least one processor may be configured to determine from the signals a plurality of baseline time-based water usage profiles, such that the time-based water usages profiles vary from each other depending on time. At least one processor may be configured to receive from the at least one sensor signals indicative of current water usage. At least one processor may be configured to, determine from the current signals a current water usage profile associated with at least one of a particular day of week and a particular time of day of the current signals. At least one processor may be configured to compare the current water usage profile with at least some of the baseline water usage profiles corresponding to at least one of the particular day of week and time of day.

In some embodiments, at least one processor may be configured to determine a likely water usage abnormality based on the comparison. The at least one processor may be configured to initiate remedial action if an abnormality is determined.

In some embodiments, the water usage profiles may vary from each other based on a schedule. The water usage profiles may vary from each other based on at least one of day of week and time of day. The at least one processor may be configured to permit an administrator to set at least one of the baseline water usage profiles for a future administrator-selected time period, where the at least one processor may be configured to automatically set a baseline water usage profile based on at least one of time and day.

In some embodiments, remedial action may include automatically closing a valve. The remedial action may include sending a warning. The remedial action may include a user alert configured to only be sent during scheduled hours.

Exemplary Embodiments of Varying Water Usage Costs Based on Appliance

A potential benefit of some embodiments may be that systems and methods of the present disclosure may provide infrastructure and/or methods for charging different rates per appliances. For example, by using a single meter and/or sensor a service provider may charge differently for a consumer's home and garden usage. Applying variable prices may include applying incremental water prices.

Historically, water prices usually have been proportional to the volume of water consumed by the end user. In some embodiments, each unit of volume may cost a certain amount of money (e.g., $4 per 1000 liter, $1 per 1000 gallons, $350 k per 1 acre-foot, etc.). Prices for the first fixed volume of water and another price for other different fixed volumes are shown by way of non-limiting example in TABLE 1 below:

TABLE 1

| From (liters) | To (liters) | Price ($) per liter |
|---|---|---|
| 1 | 500 | 4 |
| 501 | 1200 | 6 |
| 1201 | N/A | 11 |

In some embodiments, different prices may also be associated to the type of customer, such as the following non-limiting examples: residential, commercial, and senior citizens. A potential benefit of some embodiments may providing different prices according to the types of consumption, so specific usage may have a different price although the water may be the same water. This way a regulator may set a low price for essential consumption, such as drinking, and higher prices for luxury usage, such as irrigating a garden or filling up a swimming pool.

An aspect of some embodiments may include an electronic sensing and allocation system for a distributed water infrastructure containing a plurality of differing appliances. The system may comprise at least one processor. The at least one processor may be configured to receive, from at least one sensor upstream of the plurality of differing appliances, a plurality of signals indicative of water usage within the distributed water infrastructure. The at least one processor may be configured to extract, from the plurality of signals, first information identifying a volume of water usage of at least a first appliance. The at least one processor may be configured to attribute a first volume of water to a first category. At least one processor may be configured to extract, from the plurality of signals, second information identifying a volume of water usage of at least a second appliance. The at least one processor may be configured to attribute a second volume of water to a second category, where a first rate schedule may be applicable to the first category, and a second rate schedule, other than the first rate schedule, may be applicable to the second category, In some embodiments, at least one processor may be configured to output a first indication of the first volume of water together with an indicator attributing the first volume of water to the first rate schedule. The at least one processor may be configured to output a second indication of the second volume of water together with an indicator attributing the second volume of water to the second rate schedule. This may enable billing the first and second volumes of water to a consumer at differing rates based on differing uses.

An aspect of the disclosure may be directed to a system for applying variable prices in a distributed water infrastructure based water usage by a plurality of differing appliances, the system comprising at least one processor. The at least one processor may be configured to receive, from a meter upstream of the plurality differing appliances, a signal indicative of water usage. The at least one processor may differentiate between water usage of a first appliance and a second appliance, attribute a first volume of water usage to the first appliance, attribute a second volume of water usage to the second appliance, bill at a first rate water usage attributed to the first appliance, and bill at a second rate water usage attributed to the second appliance.

In some embodiments, the first indication of the first volume of water may include a category indication. The output indicator of at least the first volume of water further may include an indication of a time period in which the first volume of water was consumed. The output indicator of at least the first volume of water may contain at least one appliance indicator that attributes the first volume of water to at least one appliance that consumed the first volume of water. The category indication may reflect at least one of outdoor irrigation use and indoor use.

In some embodiments, the at least one processor may be configured to distinguish between water used for personal hygiene and water used by water-consuming machines, and to attribute water usage to a corresponding category.

In some embodiments, the at least a first appliance may include water appliances used in an irrigation system, where the first volume of water may be output for billing according to an irrigation rate schedule. At least one of a first rate schedule and a second rate schedule may take into account a time period of water usage, where volumes of water may be output together with a time period indicator to enable billing, at least in part, on the time period of water usage. The time period indicator may be reflective of water usage during a drought condition, to enable application of a drought billing rate. The at least one processor may be configured to output a suggestion to a user to alter water usage practice in order to obtain lower water rates.

In some embodiments, a method may further comprise a transmitter, where the at least one processor may be configured to transmit, via the transmitter, the indicator attributing the first volume of water to the first rate schedule and the second indicator attributing the second volume of water to the second rate schedule to a central billing server. The at least one processor may be configured to incrementally time stamp continuing water usage to enable variable billing rates based on time-based consumption. The at least one processor may be configured to identify a plurality of differing appliances of a same type, and to attribute the plurality of differing appliances to a common category. The first appliance may be at least one of a toilet, faucet, and shower.

The at least one processor may be configured to initiate a remedial action when a total cost of water consumption reaches a preset threshold value. The remedial action may include causing an alert message to be sent, sending a signal to a valve to stop water flow, and providing a notification regarding consumer compliance with a water restriction.

In some embodiments, at least one sensor may be a flow sensor. The at least one sensor may be a smart meter configured to record consumption of water in intervals of an hour or less and to communicate consumption of water to a water utility company.

Figure 16:
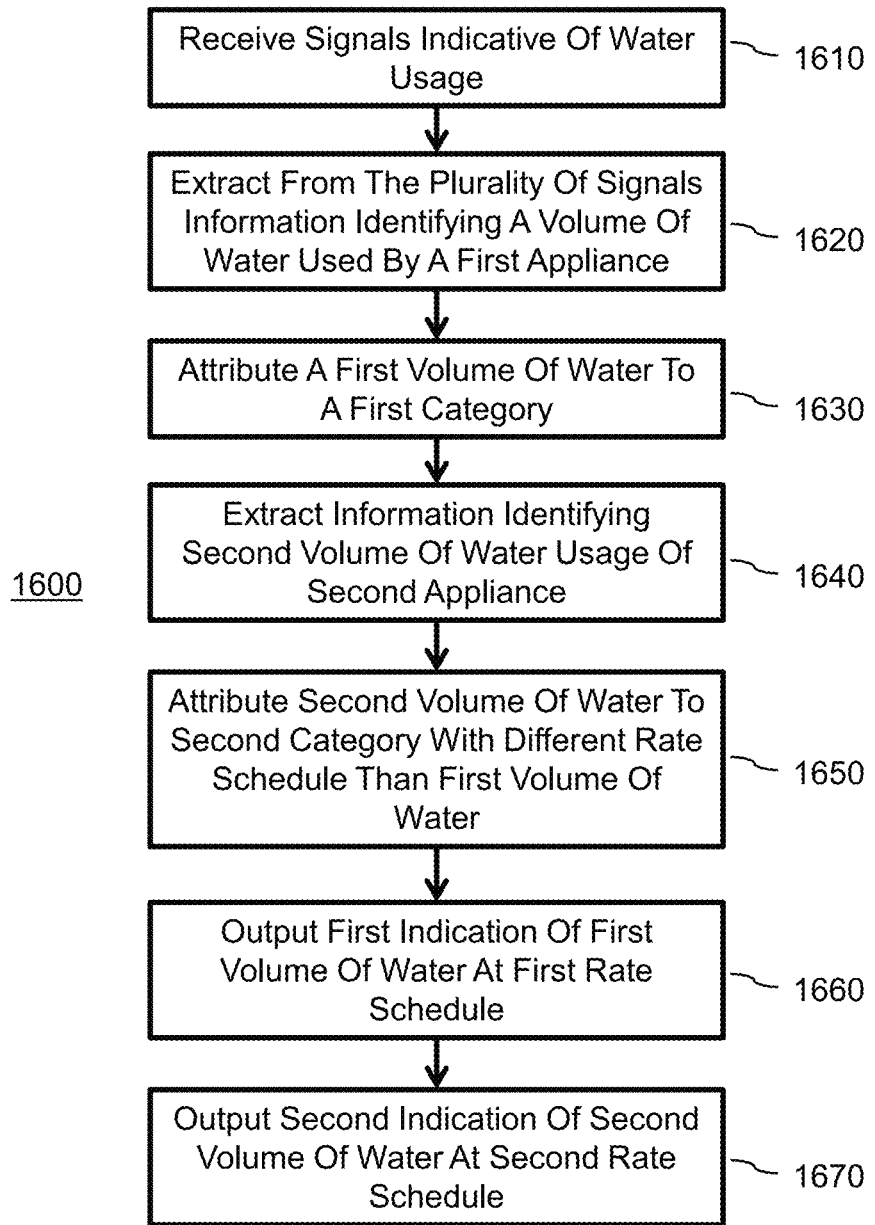
FIG. 16 illustrates an exemplary method of electronic sensing and allocation for a distributed water infrastructure containing a plurality of differing appliances.

FIG. 16 illustrates an exemplary method 1600 for electronic sensing and allocation for a distributed water infrastructure containing a plurality of differing appliances. The operations of method 1600 discussed herein are intended to be illustrative. In some embodiments, method 1600 may be implemented with one or more additional operations not described, and/or without one or more of the operations discussed. Additionally, the order in which the operations of method 1600 are illustrated in FIG. 16 and described herein is not intended to be limiting.

In some embodiments, method 1600 may be implemented in one or more processing devices. The one or more processing devices may include one or more devices executing some or all the operations of method 1600 in response to instructions stored electronically on an electronic storage medium. The one or more processing devices may include one or more devices configured through hardware, firmware, and/or software to be specifically designed for execution of one or more of the operations of method 1600.

In some embodiments, at operation 1610, at least one processor may be configured to receive, from at least one sensor upstream of the plurality of differing appliances, a plurality of signals indicative of water usage within the distributed water infrastructure. At operation 1620, at least one processor may be configured to extract, from the plurality of signals, first information identifying a volume of water usage of at least a first appliance. At operation 1630, at least one processor may be configured to attribute a first volume of water to a first category. At operation 1640, at least one processor may be configured to extract, from the plurality of signals, second information identifying a volume of water usage of at least a second appliance. At operation 1650, at least one processor may be configured to attribute a second volume of water to a second category, where a first rate schedule may be applicable to the first category and a second rate schedule, other than the first rate schedule, may be applicable to the second category. At operation 1660, at least one processor may be configured to output a first indication of the first volume of water together with an indicator attributing the first volume of water to the first rate schedule. At operation 1670, at least one processor may be configured to output a second indication of the second volume of water together with an indicator attributing the second volume of water to the second rate schedule. This may enable billing of the first and second volumes of water to a consumer at differing rates based on differing uses.

In some embodiments, the measurement of water usage may be performed by any one of the systems described herein, and/or the measure of water usage may be performed by a third-party water measuring device. The measurement of water usage may be performed by separate devices distributed by distance, where the processing operations may be performed locally or at a central location. The processing operations may be performed in real time, and/or at a later time. The processing operations may also be provided by distributed parallel or cloud computing infrastructures with data and results transported to the cloud or parallel processor using wireless or wired networks.

In accordance with the present disclosure, some of the embodiments described herein provide novel benefits in event-based leak detection systems and methods. A measurement of the number of liters consumed as a function of time may be transformed into a water usage pattern that has a particular fingerprint or water usage pattern. A water usage pattern may be determined by any method consistent with identification herein, such as the non-limiting examples of: event-based threshold method, guided machine learning, or automatic machine learning. Water usage pattern determination may be assisted by a neural network, where a system may progressively improve performance to determine, identify, and compare water usage patterns by considering examples. A neural network may be used without task-specific programming.

In various alternative methods, electronic sensing and allocation for a distributed water infrastructure containing a plurality of differing appliances may be implemented by alternative methods of receiving water information, and employing event-based leak detection systems and methods to provide granularity of water usage to an end user.

Exemplary Embodiments of a White List for Abnormal Water Events

A dictionary of profiles may be used to identify an abnormal water usage. When detecting such profiles, the system may identify the water flow as an abnormal consumption or a faulty appliance. Additionally, the system may store water profiles that would otherwise be classified as abnormal water events, except that they are whitelisted. For example, a system may attempt to characterize an event from prior characteristics, and if it cannot find a prior characteristic the system may prompt the user to do either add the water event to a whitelist or to a list of known abnormal water events.

In some embodiments, the system may comprise at least one processor. The system may comprise memory for storing a plurality of abnormal water usage profiles. The at least one processor may be configured to receive from a water meter in a distributed water infrastructure successive indications of water usage. At least one processor may be configured to compare the successive indications of water usage with the stored abnormal water usage profiles. At least one processor may be configured to determine, based on the comparison, a correlation between at least one indication and at least one abnormal water usage profile. At least one processor may be configured to initiate remedial action when a correlation is determined.

An aspect of some embodiments may include a system for detecting abnormal water consumption, the system may comprise memory for storing a plurality of abnormal water usage profiles and at least one processor configured to receive from a water meter in a distributed water infrastructure successive indications of water usage. The system may compare the successive indications of water usage with the stored abnormal water usage profiles, and based on the comparison, determine a correlation between at least one indication and at least one abnormal water usage profile. When a correlation is determined, the system may initiate remedial action.

Exemplary Embodiments of a Learning Algorithm and Learning Period

An aspect of some embodiments may include a system for recognizing liquid usage patterns in a distributed liquid infrastructure. In some embodiments, the system may be configured to classify normal or abnormal water (or fluid) usage and may take action based on a comparison with a classification database. The system may comprise at least one processor. At least one processor may be configured to receive, from at least one sensor, information about liquid usage in the distributed liquid infrastructure. At least one processor may be configured to determine over time expected patterns of liquid usage and classify the expected patterns as normal usage patterns. At least one processor may be configured to detect a usage pattern that does not correspond to a classified normal usage pattern and initiate remedial action when the usage pattern does not correspond to a classified normal usage pattern.

In some embodiments, at least one processor may be configured to measure water usage patterns during a learning period and execute a learning algorithm. A learning algorithm may include steps for a length of time, or the number of events required, before the learning algorithm completes. A learning algorithm may include steps for prompting an end user to classify a water usage, prompting an end user to initiate a water usage, and classifying the water usage.

In some embodiments, the learning algorithm may determine classifications for the water usage patterns automatically. The learning algorithm may learn to identify events without knowing what the event is. For example, the learning algorithm may identify a normal water usage that occurs every morning, and classify the event as normal even if the learning algorithm does not identify the event as a shower.

An aspect of the disclosure may be directed to a system for recognizing liquid usage patterns in a distributed liquid infrastructure, the system comprising at least one processor. The processor may be configured to receive from at least one sensor, information about liquid usage in the distributed liquid infrastructure. The processor may determine over time expected patterns of liquid usage, classifying the expected patterns as normal usage patterns. The processor may detect a usage pattern that does not correspond to a classified normal usage pattern, and initiate remedial action when a usage pattern is detected that does not correspond to a classified normal usage pattern.

Exemplary Embodiments of Cloud-Based Water Analytics

An aspect of some embodiments may include a system for monitoring water usage of a plurality of appliances in a plurality of distributed locations remote from one another. A system may comprise many distributed water meters (from any vendor) connected to the cloud. The system may learn normal water profiles, transfer data to a water data-analytics system in the cloud that processes the data, and provide useful information. The system may monitor distributed water devices and sensors that can be located at various locations. Even though these devices are not necessarily in close proximity, such devices may send data to a central location, and may interact with each other via the system.

In some embodiments, the system may comprise at least one processor. The system may comprise at least one central processor. A central processor may be a processor that is configured to receive information and perform processing steps from several disparate locations.

In some embodiments, at least one processor may be configured to receive water usage data from the plurality of distributed locations. At least one processor may be configured to determine, from the water usage data received from the plurality of distributed locations, a common appliance used in each of the plurality of distributed locations. A common appliance may include an appliance, or class of appliances, that at least two different distributed water infrastructures share in common. A common appliance might not be an identical appliance, but rather a type or model of appliance that makes it possible to compare appliances in different distributed water infrastructures.

In some embodiments, at least one processor may be configured to analyze a subset of the water usage data attributable to the common appliance to determine usage patterns associated with the common appliance across the plurality of distributed locations. Aggregating may include to aggregating all the relevant water data from the devices into one central database for comparison and analytics. Information about usage of the common appliance may include to information gathered and aggregated to provide insight into the proper working of other common appliances located in other locations.

In some embodiments, at least one processor may be configured to output usage pattern analytics associated with the common appliance. The at least one central processor may be configured to receive water usage data from a plurality of local processors at the plurality of distributed locations, where the plurality of local processors may be configured to analyze local patterns of water usage, match a local pattern of water usage with a pattern associated with the common appliance, and transmit to the at least one central processor water usage data associated with the common appliance.

In some embodiments, the at least one central processor may be configured to transmit, to a plurality of local processors at each of the plurality of distributed locations, at least one water usage pattern signature to facilitate detection of the common appliance by the plurality of local processors. The at least one central processor may be configured to determine, from the water usage data, whether a common appliance may be malfunctioning at one of the plurality of distributed locations.

In some embodiments, the at least one central processor may be configured to store an address associated with an administrator of each of the plurality of distributed locations and to send an alert to the administrator of a malfunctioning appliance. The at least one central processor may be configured to determine, using the water usage data, at least one analytic relating to at least one of frequency of use of an appliance and duration of use of an appliance. The at least one central processor may output the at least one analytic for presentation to a manufacturer of the appliance. The at least one central processor may be configured to aggregate, in memory, historical water consumption information about the common appliance, gleaned from water usage data collected over a plurality of days. The historical consumption information may include at least one of a water flow profile, water flow rate, water pressure, and total water consumed for a cycle or period.

In some embodiments, the at least one central processor may be configured to receive water usage data from the plurality of local processors on at least a daily basis. The at least one central processor may be configured to identify a malfunction by comparing current water usage data at a first location with water usage data for an appliance known to have malfunctioned at a second location. The at least one central processor may be configured to output, for each of the plurality of distributed locations, a comparison of local water usage with aggregated communal water consumption. The at least one central processor may be configured to output, for each of the plurality of distributed locations, usage pattern analytics categorizing local water usage by appliance.

In some embodiments, each local processor may be associated with at least one local flow sensor upstream of a plurality of appliances and configured to collected data relating to simultaneous operation of at least some of the plurality of appliances. The at least one central processor may be configured to receive water usage information derived from the data relating to simultaneous operation of at least some of the plurality of appliances. The at least one local flow sensor may have a resolution of at least 0.2 liters per hour.

An aspect of the disclosure may be directed to a system for monitoring water usage of a plurality of appliances in a plurality of distributed locations remote from one another, the system comprising at least one processor. The at least one processor may be configured to receive water usage data from the plurality of distributed locations, and analyze the water usage data to determine usage patterns in the usage data from each of the plurality of locations. The at least one processor may determine, in each of the usage patterns, a common appliance used in each of the plurality of distributed locations, and aggregate, from the water usage data, information about usage of the common appliance from the plurality of locations.

Figure 17:
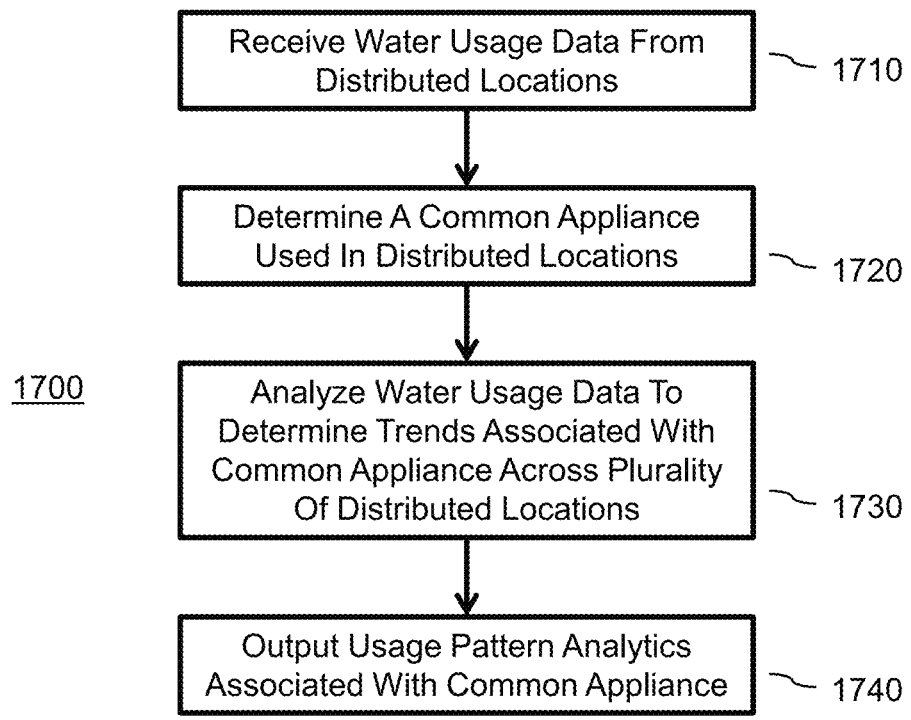
FIG. 17 illustrates an exemplary method for monitoring water usage of a plurality of appliances in a plurality of distributed locations remote from one another.

FIG. 17 illustrates an exemplary method 1700 for monitoring water usage of a plurality of appliances in a plurality of distributed locations remote from one another. The operations of method 1700 discussed herein are intended to be illustrative. In some embodiments, method 1700 may be implemented with one or more additional operations not described, and/or without one or more of the operations discussed. Additionally, the order in which the operations of method 1700 are illustrated in FIG. 17 and described herein is not intended to be limiting.

In some embodiments, method 1700 may be implemented in one or more processing devices. The one or more processing devices may include one or more devices executing some or all the operations of method 1700 in response to instructions stored electronically on an electronic storage medium. The one or more processing devices may include one or more devices configured through hardware, firmware, and/or software to be specifically designed for execution of one or more of the operations of method 1700.

In some embodiments, at operation 1710, at least one processor may be configured to receive water usage data from a plurality of distributed locations. At operation 1720, at least one processor may be configured to determine from the water usage data received, from the plurality of distributed locations, a common appliance used in each of the plurality of distributed locations.

In some embodiments, at operation 1730, at least one processor may be configured to analyze a subset of the water usage data attributable to the common appliance to determine usage patterns associated with the common appliance across the plurality of distributed locations. At operation 1740, at least one processor may be configured to output usage pattern analytics associated with the common appliance.

In some embodiments, the measurement of water usage may be performed by any one of the systems described herein, and/or the measure of water usage may be performed by a third-party water measuring device. The measurement of water usage may be performed by separate devices distributed by distance, where the processing operations may be performed locally or at a central location. The processing operations may be performed in real time, and/or at a later time. The processing operations may also be provided by distributed parallel or cloud computing infrastructures with data and results transported to the cloud or parallel processor using wireless or wired networks.

In accordance with the present disclosure, some of the embodiments described herein provide examples of the novel benefits of event-based leak detection systems and methods. A measurement of the number of liters consumed as a function of time may be transformed into a water usage pattern that has a particular fingerprint or water usage pattern. A water usage pattern may be determined by any method consistent with identification herein, such as the non-limiting examples of: event-based threshold method, guided machine learning, or automatic machine learning. Water usage pattern determination may be assisted by a neural network, where a system may progressively improve performance to determine, identify, and compare water usage patterns by considering examples. A neural network may be used without task-specific programming.

In various alternative methods, monitoring water usage of a plurality of appliances in a plurality of distributed locations may be implemented by alternative methods of receiving water information, and employing event-based leak detection systems and methods to provide granularity of water usage to an end user.

Exemplary Embodiments of Increasing the 'Zero' Threshold

The minimum flow rate for consumption may be increased to the level of a reported abnormal water flow having a certain flow rate, when the administrator chooses to ignore the abnormality. This may avoid reporting the same flow as an abnormal consumption more than once.

An aspect of the disclosure may be directed to a system for detecting abnormal water consumption. The system may comprise at least one processor. The at least one processor may be configured to receive from at least one sensor a water usage indicator, determine an existence of a likely abnormality from the received indicator, report the likely abnormality to an administrator, receive from the administrator a message to ignore the likely abnormality, adjust a threshold to prevent further reporting to the administrator when the water usage indicator corresponding to the likely abnormality is later detected again. In order to prevent customer harassment and over-messaging, the system may have a mechanism to adjust a threshold to reduce further reporting to the administrator.

An aspect of some embodiments may include a system for detecting abnormal water consumption, the system comprising at least one processor. The at least one processor may be configured to receive from at least one sensor a water usage indicator, determine an existence of a likely abnormality from the received indicator, report the likely abnormality to an administrator, receive from the administrator a message to ignore the likely abnormality, adjust a threshold to prevent further reporting to the administrator when the water usage indicator corresponding to the likely abnormality may be later detected again.

Figure 18:
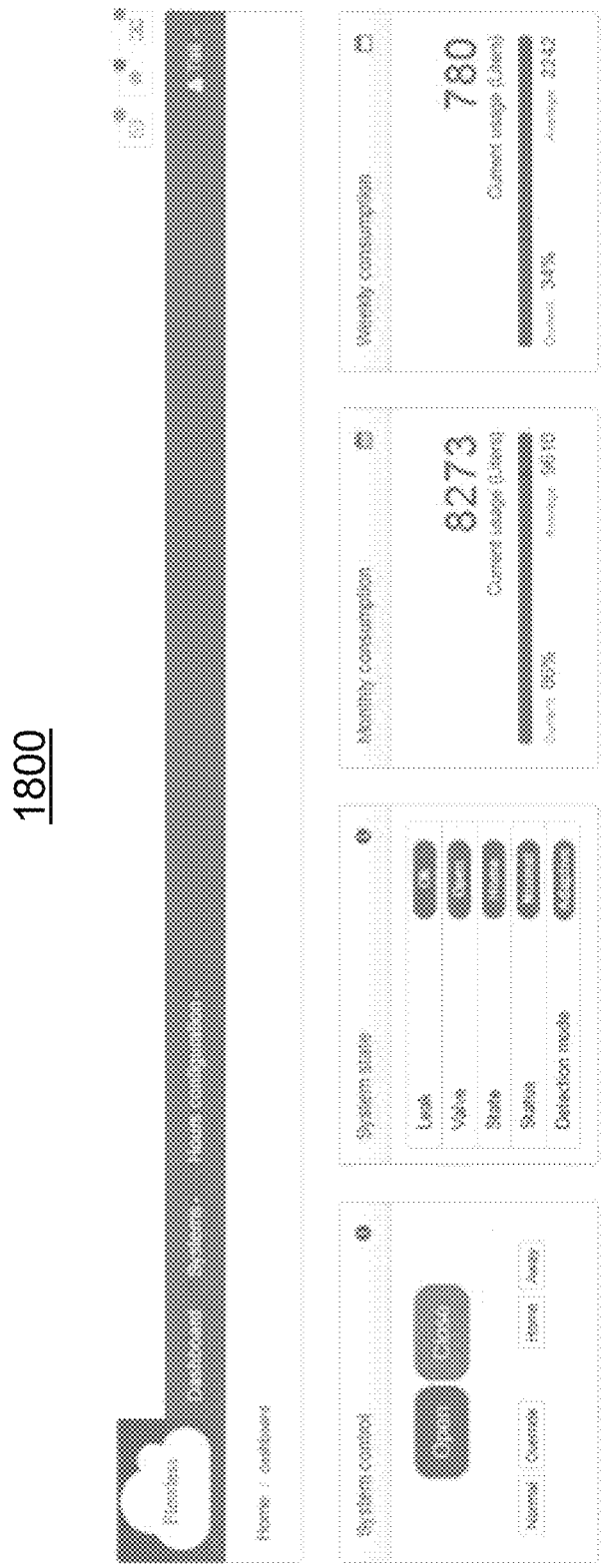
FIG. 18 illustrates an exemplary graphical user interface for a system that may remotely control a valve and track water usage.

FIG. 18 illustrates an exemplary graphical user interface 1800 for a system that may remotely control a valve and track water usage. The graphical user interface may provide system controls to a user, indicate whether a valve status is open or closed, and provide options to open or close the valve. The graphical user interface may show a system state, and may indicate whether there is a leak detected in the system, whether a specific valve is opened or closed, a vacation status of an end user, a status of the monitoring system (e.g., normal or threshold), and a detection mode status (e.g., adaptive or manual). The graphical user interface may also provide information on monthly consumption and weekly consumption.

Figure 19A:
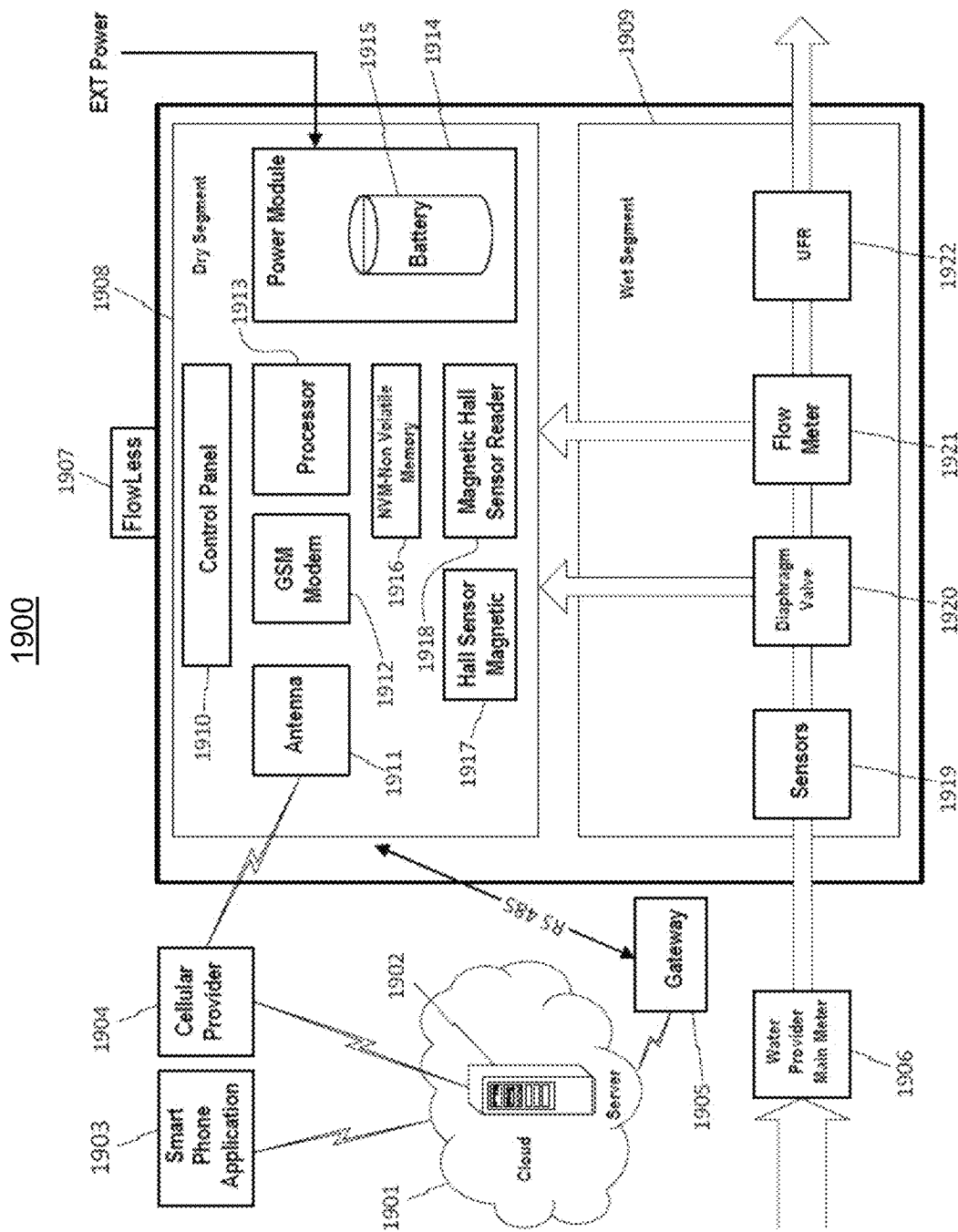
FIG. 19a illustrates an exemplary system for detecting consumption of liquids.

FIG. 19a illustrates an exemplary system 1900 for detecting consumption of liquids and/or water quality. System 1900 may include a server 1902 and clients, such as client 1907. Client 1907 may communicate with server 1902 on a cloud 1901. Communication between a server and a particular client 1907 may take place through a cellular provider 1904, or through a gateway 1905. Communication with an end user may take place through a smart phone application 1903. Client 1907 may be installed with a distributed water infrastructure 100, downstream of a water provider main meter 1906. Client 1907 may be part of a system comprising a dry segment 1908 and a wet segment 1909. Client 1907 may comprise a control panel 1910, antenna 1911, GSM modem 1912, processor 1913, power module 1914, battery 1915, NVM-nonvolatile memory 1916, magnetic hall sensor 1917, magnetic hall sensor reader 1918, sensors 1919, diaphragm valve 1920, flow meter 1921, and unmeasured flow reducer (UFR) 1922.

Figure 19B:
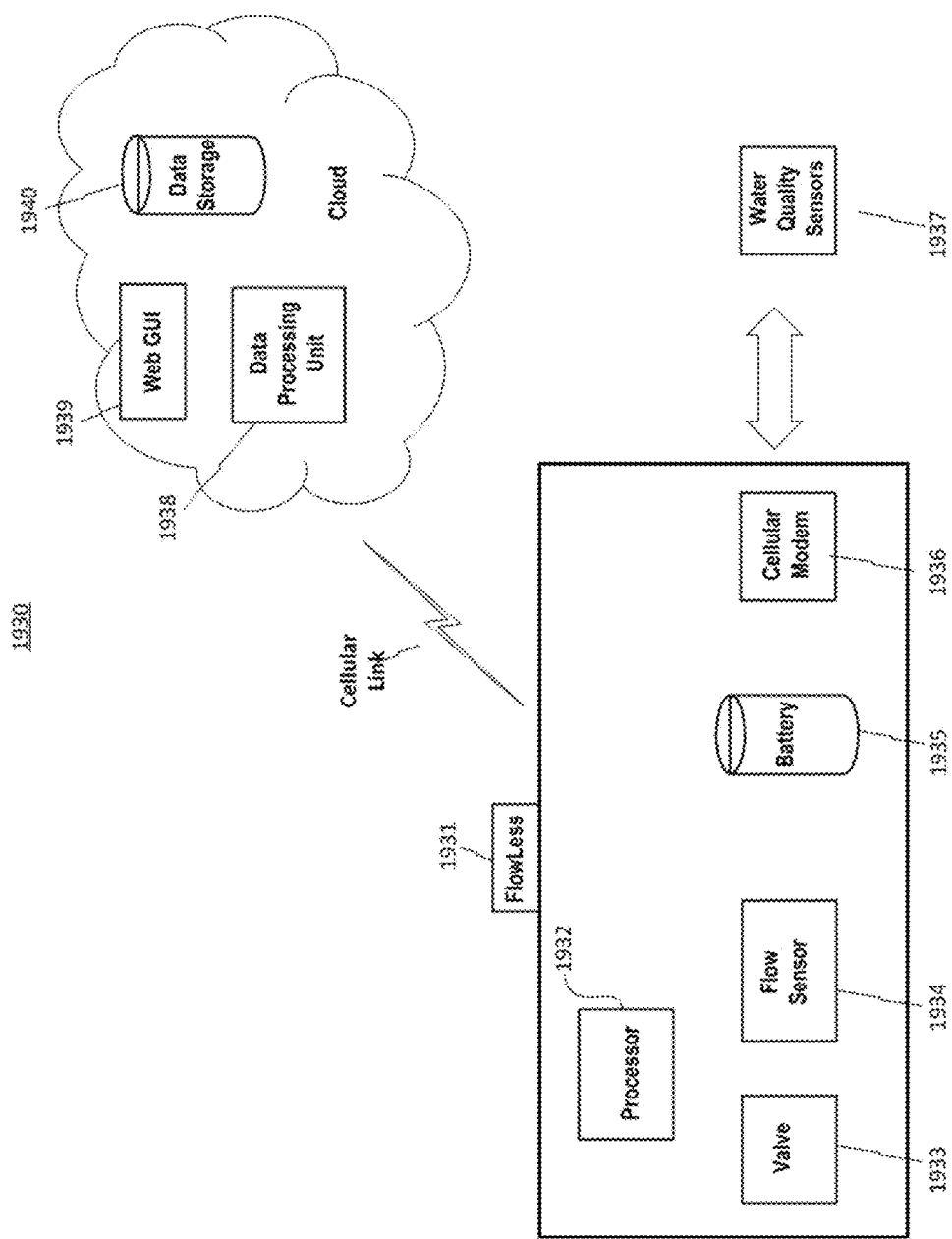
FIG. 19b illustrates an exemplary system for detecting consumption of liquids where data processing and data storage occur in the cloud.

FIG. 19b illustrates an exemplary system 1930 for detecting consumption of liquids and/or water quality. In some embodiments, a system may be configured to perform data processing and storage operations in the cloud. System 1930 may include a system 1931 that may comprise a processor 1932. Processor 1932 may be a CPU configured to transfer raw or unprocessed data to the cloud. System 1930 may include a valve 1933, a flow sensor 1934, and a battery 1935. In some embodiments, system 1930 may comprise water quality sensors 1937. Processor 1932 may be configured to transfer data to the cloud via a cellular modem 1936 that may establish a cellular link to the cloud. The cloud may comprise a distributed network of servers, with at least one data processing unit 1938 and with at least one component for data storage 1940. Data stored in the cloud may be accessed from remote locations through a Web GUI 1939.

Figure 19C:
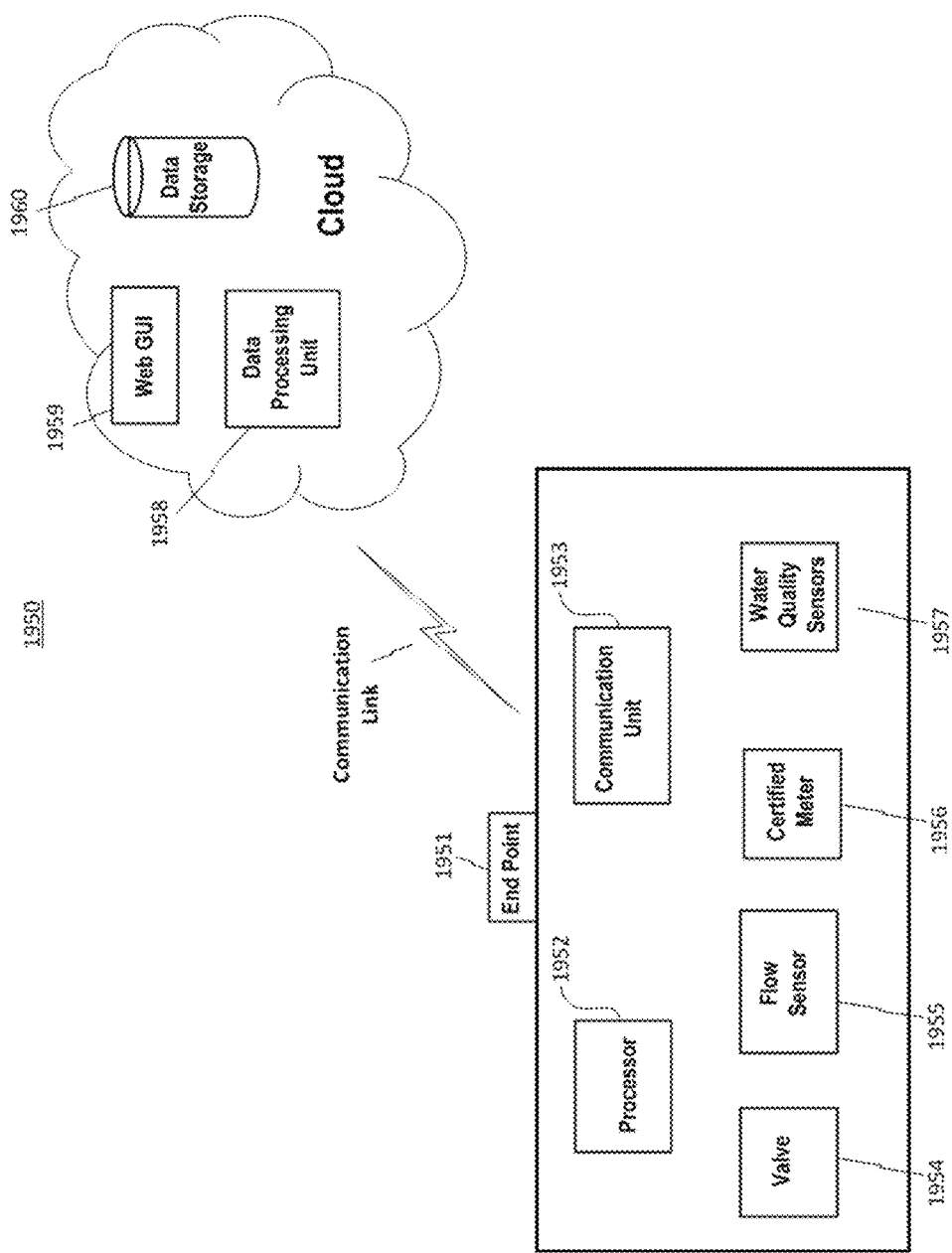
FIG. 19c illustrates an exemplary system for detecting consumption of liquids where an end device performs data collection and transmission, and data processing and data storage occur in the cloud.

FIG. 19c illustrates an exemplary system 1950 for detecting consumption of liquids and/or water quality. In some embodiments, a system may be configured such that an end device provides data collection and data communication. Such a system may be configured to perform additional data processing steps and data storage in the cloud. System 1950 may include an end point device 1951 that may comprise a processor 1952. Processor 1952 may be a CPU configured to transfer raw or unprocessed data to the cloud through a communication link. System 1950 may include a valve 1954, a flow sensor 1955, a certified meter 1956, and water quality sensors 1957. Processor 1952 may be configured to transfer data to the cloud via a communication unit 1953, which may establish a cellular link to the cloud. The cloud may comprise a distributed network of servers, with at least one data processing unit 1958 and at least one component for data storage 1960. Data stored in the cloud may be accessed from remote locations through a web GUI 1959.

The foregoing concepts though described in connection with water are not limited to water, and can be used with any fluid, such as chemicals, petroleum products, waste products, gaseous/liquid substances, or any other material used in a commercial or non-commercial application. In addition, while the preceding concepts are expressed for exemplary purposes in a single form, it may be envisioned that each concept could be expressed in terms of either a system, method, or computer readable medium. In such instances, the claim elements are expressible as steps, instructions, or hardware. Although the invention has been described in a variety of embodiments, this description is not meant to be construed in a limiting manner. Inventive concepts may include systems that feature combinations of elements and/or processing steps from each disclosed embodiment. Various modifications of the disclosed embodiments as well as alternative embodiments of the inventions are expressly envisioned by this disclosure.

For example, in one exemplary embodiment, systems consistent with the present invention may comprise an electronically controllable valve, a remote communication transmitter, a remote communication receiver, at least one consumption sensor for measuring water flow information associated with the distributed water infrastructure, and at least one processor. The system may comprise at least one central processor. The system may further comprise any of the components from exemplary systems 200, 201, 400, 401, 1800, and 1900, and user interface 1240.

The system may be configured to detect a leak, and inform water consumers about their water consumption. The system may comprise specific elements to measure the status of water, process this information, communicate to an end user, and take an automatic remedial action. The system may receive from at least one sensor associated with the distributed water infrastructure signals indicative of water usage in the distributed water infrastructure, and aggregate groups of signals to construct a plurality of time-based water event profiles, each water event profile containing a distribution of water usage indicators over time. The system may store a subset of the plurality of water event profiles in memory as normal water event profiles, and receive, from the at least one sensor, signals indicative of current water usage in the distributed water infrastructure. The system may construct, from the signals indicative of current water usage, at least one current water event profile, and compare the at least one current water event profile with normal water event profiles stored in the memory. The system may initiate remedial action if the at least one current water event profile does not substantially correspond to normal water event profiles stored in the memory.

The system may further determine, from the water flow information obtained from the at least one consumption sensor, a potential abnormal consumption associated with the distributed water infrastructure. The system may automatically close a valve, without human intervention, when the potential abnormal consumption is determined. The system may transmit, via the remote communication transmitter to a remote administrator, alert information about the potential abnormal consumption to enable an administrator to decide based on the transmitted information whether to reopen the valve. The system may receive, from the administrator via the remote communication receiver a control signal to reopen the valve despite the information about the potential abnormal consumption, and reopen the valve.

The system may further receive from at least one sensor associated with the distributed water infrastructure indications of regular water usage. The system may determine, from a plurality of indications received over a time period, a plurality of baseline water usage profiles. The system may receive from the at least one sensor a current water usage profile. The system may compare the current water usage profile with the plurality of baseline water usage profiles. The system may determine an water abnormal consumption based on the comparison between the current water usage profile and the plurality of baseline water usage profiles. The system may generate an abnormal water consumption signal when abnormal water consumption is determined. The system may receive, from at least one sensor associated with the distributed water infrastructure, signals indicative of water usage in the distributed water infrastructure. The system may determine, from the signals indicative of water usage, a current water usage pattern.

The system may access a database of a plurality of stored water usage patterns, where each at least one stored water usage pattern is associated with at least one human health or lifestyle state. The system may compare at least one current water usage pattern with at least some of the stored water usage patterns. The system may, based on the comparison, identify a human health or lifestyle condition reflected by the current water usage pattern. The system may institute a remedial action corresponding to the identified human health or lifestyle state.

In some embodiments, the system may receive, from a location in the distributed water infrastructure upstream of the plurality of water appliances, historical water usage measurements. The system may determine from the historical water usage measurements at least one unique water usage signature associated with each of the plurality of water appliances. The system may store in memory each at least one unique water usage signature for each of the plurality of appliances. The system may receive, from the location in the distributed water infrastructure upstream of the plurality of water appliances, current water usage measurements. The system may determine from the current water usage measurements at least one current water usage signature. The system may compare the current water usage signature with at least one of the unique water usage signatures stored in memory to determine a match. The system may, based on the signature match, ascertain an identifier of a water appliance in current use.

The system may receive water appliance usage data from the plurality of geographically distributed water sensors, where each water sensor is located upstream of a plurality of water appliances in an associated distributed water infrastructure, and where each water sensor is configured to collect data from an infrastructure inlet flow reflective of operation of at least one specific category of water appliance downstream of the water sensor. The system may compare the water appliance usage data from the plurality of geographically distributed water sensors to determine trends in operation of the at least one specific category of water appliance across a population. The system may output information about the trends in operation. The system may detect, from at least one sensor in a distributed water infrastructure upstream of the plurality of water appliances, a plurality of normal water usage profiles. The system may associate at least one of the plurality of normal water usage profiles with each of the plurality of water appliances. The system may store each of the plurality of normal water usage profiles in a manner associating each of the plurality of normal water usage profiles with an associated water appliance.

The system may detect at least one current water usage profile. The system may compare the at least one current water usage profile with at least one of the stored normal water usage profiles to determine a corresponding identity of an associated water usage appliance and to determine if a substantial deviation exists between the stored normal water usage profile for the identified appliance and the at least one current water usage profile, where the substantial deviation is reflective of a potential malfunction in the associated water usage appliance. The system may initiate remedial action if the substantial deviation, reflective of a potential malfunction, is determined.

The system may construct from signals indicative of water usage a plurality of water event profile signatures. The system may, based on differences between similar water event profiles, associate at least one water event profile signature with a first water consumer and associate a second water event profile signature with a second water consumer. The system may store the water event profile signatures for the first water consumer and the second water consumer. The system may construct current water event profiles reflecting subsequent water usage in the distributed water infrastructure. The system may compare the current water event profiles with water event profile signatures stored in memory. The system may, based on the comparison, attribute a first current water event profile to the first water consumer and attribute a second current water event profile to the second water consumer. The system may output data for generating at least one report of water usage by the first water consumer.

Accordingly, inventive concepts in the present disclosure may include systems that feature combinations of elements and/or processing steps from any and each disclosed embodiment, separately or in combination. Such modifications and combinations of the disclosed embodiments as well as alternative embodiments of the inventions are expressly included in this disclosure.

What is claimed is:

1. A system for detecting abnormal consumption in a distributed water infrastructure, the system comprising:
at least one processor configured to:
receive from at least one sensor associated with the distributed water infrastructure indications of regular water usage, wherein the distributed water infrastructure includes a plurality of water appliances;
determine from the indications received over a time period, at least one recurring time period of expected diminished water usage;
determine for the at least one recurring time period of expected diminished water usage at least one expected diminished water usage profile;
receive from the at least one sensor during a current time period of expected diminished water usage, indications of current water usage, constituting a current water usage profile;
compare the current water usage profile during the expected period of diminished water usage with the at least one expected diminished water usage profile;
based on the comparison, determine that water usage in the current water usage profile materially exceeds water usage in the at least one expected diminished water usage profile; and
execute a remedial action when, based on the comparison, the current water usage profile materially exceeds the at least one expected diminished water usage profile.

2. The system of claim 1, wherein the at least one sensor has a resolution of less than 50 cubic centimeters.

3. The system of claim 1, wherein the at least one expected diminished water usage profile includes a plurality of profiles each associated with different recurring time periods of expected diminished water usage, and wherein during comparing, the current water usage profile is compared with one of the plurality of expected diminished water usage profiles corresponding to the current time period of expected diminished water usage.

4. The system of claim 3, wherein at least one of the plurality of expected diminished water usage profiles corresponds to a night time period when substantially no normal water usage is expected in the distributed water infrastructure.

5. The system of claim 4, wherein the at least one expected diminished water usage corresponding to the night time period takes into account automated consumption of water from appliances and periodically occurring irregular uses.

6. The system of claim 1, wherein the at least one processor is further configured to compare the current water usage profile with at least one preset water usage profile that corresponds to a leak.

7. The system of claim 6, wherein the at least one preset water usage profile corresponds to a leak of at least 1 liters per hour.

8. The system of claim 1, wherein the remedial action includes generating an abnormal consumption alert.

9. The system of claim 1, wherein the at least one processor is further configured to compare the current water usage profile with at least one preset water usage profile that corresponds to one of the plurality of water appliances, and wherein the remedial action includes generating an abnormal consumption alert associated with the water appliance.

10. The system of claim 1, wherein the current water usage profile materially exceeds the at least one expected diminished water usage profile when a quantitative measure of similarity or dissimilarity exceeds a threshold.

11. The system of claim 10, wherein the threshold comprises a standard deviation or a variance.

12. A system for detecting abnormal consumption in a distributed water infrastructure, the system comprising:
at least one processor configured to:
receive from at least one water sensor upstream of a plurality of water appliances in the distributed water infrastructure, overall water consumption measurements;
determine periods when the distributed water infrastructure is in an inactive state of substantial non-use of the plurality of water appliances;
track the overall water consumption measurements during a plurality of times when the distributed water infrastructure is in an inactive state;
detect an upward trend in the tracked water consumption measurements over the plurality of times; and
initiate remedial action when the upward trend is detected.

13. The system of claim 12, wherein the at least one sensor has a resolution of less than 50 cubic centimeters.

14. The system of claim 12, wherein the remedial action includes generating an abnormal consumption alert.

15. The system of claim 12, wherein the at least one processor is configured to automatically determine periods when the distributed water infrastructure is in the inactive state of substantial non-use of water appliances.

16. The system of claim 12, wherein the at least one processor is configured to determine periods when the distributed water infrastructure is in the inactive state by accessing a timetable stored in memory, and wherein the timetable includes times of inactivity supplied by an administrator.

17. The system of claim 12, wherein periods when the distributed water infrastructure is in the inactive state of substantial non-use of water appliances comprise a non-zero continuous baseline of water usage.

18. The system of claim 12, wherein the at least one processor is configured to construct an expected water event profile for consumption of water during the inactive state.

19. The system of claim 18, wherein the at least one processor is configured to compare current overall water consumption measurements with the expected water event profile for the consumption of water during the inactive state.

20. The system of claim 12, wherein the at least one processor is configured to store indications of a plurality of expected periods of substantial water inactivity and to initiate the remedial action when a decrease is detected in an overall number of actual periods of substantial water inactivity.

* * * * *